us006627735B2

(12) United States Patent
Kindsvogel et al.

(10) Patent No.: US 6,627,735 B2
(45) Date of Patent: Sep. 30, 2003

(54) ISLET CELL ANTIGEN 1851

(75) Inventors: Wayne Kindsvogel, Seattle, WA (US); Laura J. Jelinek, Seattle, WA (US); Paul O. Sheppard, Redmond, WA (US); William A. Hagopian, Seattle, WA (US); James M. LaGasse, Seattle, WA (US)

(73) Assignee: ZymoGenetics, Inc., Seattle, WA (US)

( * ) Notice: Subject to any disclaimer, the term of this patent is extended or adjusted under 35 U.S.C. 154(b) by 0 days.

(21) Appl. No.: 09/876,527

(22) Filed: Jun. 7, 2001

(65) Prior Publication Data

US 2002/0102616 A1 Aug. 1, 2002

Related U.S. Application Data

(62) Division of application No. 08/811,481, filed on Mar. 5, 1997, now Pat. No. 6,300,093.
(60) Provisional application No. 60/012,927, filed on Mar. 6, 1996, and provisional application No. 60/027,540, filed on Oct. 15, 1996.

(51) Int. Cl.⁷ .................................................. C07K 1/00
(52) U.S. Cl. ..................................... 530/350; 424/185.1
(58) Field of Search ........................ 530/350; 424/185.1

(56) References Cited

U.S. PATENT DOCUMENTS

| 5,200,318 A | 4/1993 | Rabin et al. ................ 435/7.21 |
| 5,989,551 A | 11/1999 | Maclareen et al. ....... 424/185.1 |

FOREIGN PATENT DOCUMENTS

| EP | 0 383 129 B1 | 5/1995 |

OTHER PUBLICATIONS

Martino et al., *J. Neuroimmunol.* 69: 129–134, 1996.
Wasmeier et al., *Diabetologia* 38(1): A69,1995.
Hawkes et al., *Diabetes* 45: 1187–1192, 1996.
Ongagna et al., *Diabetologia* 38: 370–375, 1995.
Kawasaki et al., *Diabetes* 45: 1344–1349, 1996.
Kawasaki et al., *Biochem. Biophys. Res. Comm.* 227: 440–447, 1996.
Bingley et al., *Diabetes* 43: 1304–1310, 1994.
Rabin et al., *Diabetes* 41: 183–186, 1992.
Wasmeier et al., *J. Biol. Chem.* 271(30): 18161–18170, 1996.
Lu et al., *Proc. Natl. Acad. Sci. U.S.A.* 93: 2307–2311, 1996.
Christie et al., *Diabetes* 43: 1254–1259, 1994.
Lu et al., *Biochem. Biophys, Res. Comm.* 204(2): 930–936, 1994.
Rabin et al., *J. Immunol.* 152(6):3183–3188, 1994.
Lan et al., *DNA and Cell Biology* 13(5): 505–514, 1994.
Payton et al., *J. Clin. Invest.* 96:1506–1511, 1995.
Christie et al., *J. Clin. Invest.* 92: 240–248, 1993.
Passini et al., *Proc. Natl. Acad. Sci. U.S.A..* 92: 9412–9416, 1995.
Arden et al., *J. Clin. Invest.* 97(2): 551–561, 1996.

*Primary Examiner*—Patricia A. Duffy
(74) *Attorney, Agent, or Firm*—Susan E. Lingenfelter; Michelle L. Johnson

(57) ABSTRACT

A mammalian islet cell antigen polypeptide involved in the development of insulin-dependent diabetes mellitus (IDDM) is disclosed. This islet cell antigen polypeptide, 1851, was found to contain regions of homology to the protein tyrosine phosphatase family. Methods for diagnosis and treatment, including use in immunoprecipitation assays and the induction of immune tolerance using the recombinant mammalian polypeptides and antibodies specific to mammalian islet cell antigen 1851 polypeptides are presented.

3 Claims, No Drawings

ISLET CELL ANTIGEN 1851

This application is a divisional application of U.S. Ser. No. 08/811,481 (filed Mar. 5, 1997), which issued as U.S. Pat. No. 6,300,093 (Oct. 9, 2001), and claims the benefit of U.S. Provisional application No. 60/012,927 (filed Mar. 6, 1996), and U.S. Provisional application No. 60/027,540 (filed Oct. 15, 1996), the contents of which are incorporated by reference.

BACKGROUND OF THE INVENTION

Detection of specific autoantigens in prediabetic individuals has been used as a predictive marker to identify, before clinical onset and significant β-cell loss has occurred, those at greater risk of developing IDDM (Gorsuch et al., *Lancet* 2: 1363–65, 1981; Baekkeskov et al., *J. Clin. Invest.* 79: 926–34, 1987; Johnstone et al., *Diabetologia* 32: 382–86, 1989; Ziegler et al., *Diabetes* 38: 1320–25, 1989; Baekkeskov et al., *Nature* (Lond) 347: 151–56, 1990; Bonifacio et al., *Lancet* 335: 147–49, 1990; and Bingley et al. *Diabetes* 43: 1304–10, 1994).

Antibodies to the 40 kD, and more particularly the 37 kD, ICA fragments are detected when clinical onset of IDDM is imminent and are found to be closely associated with IDDM development (Christie et al., *Diabetes* 41: 782–87, 1992). Diabetic sera containing antibodies specific to the 40 kD fragment were recently found to bind to the intracellular domain of the protein tyrosine phosphatase, IA-2/ICA512 (Lu et al., *Biochem. Biophys. Res. Comm.* 204: 930–36, 1994; Lan et al., *DNA Cell Biol.* 13: 505–14, 1994; Rabin et al., *J. Immunol.* 152: 3183–88, 1994; Payton et al., *J. Clinc. Invest.* 96: 1506–11, 1995; and Passini et al., *Proc. Natl. Acad. Sci. USA* 92: 9412–16, 1995). Antibodies specific to the 37 kD fragment are thought to bind either to a post-translational in vivo modification of IA-2/ICA512 or a different, but probably related, protein precursor (Passini et al., ibid.).

ICA 512 was initially isolated as an autoantigen from an islet cell cDNA library, and was subsequently shown to be related to the receptor-linked protein tyrosine phosphatase family (Rabin et al., ibid.). ICA 512 was later found to be identical to a mouse and human protein tyrosine phosphatase, IA-2, isolated from brain and insulinoma cDNA libraries (Lu et al., ibid.; and Lan et al., ibid.).

Detection of diabetes-associated autoantigens, especially combinations of autoantigens, genotypes, such as HLA DR and HLA DQ, and loci, such as the polymorphic region in the 5' flanking region of the insulin gene; in prediabetic individuals have been shown to be useful predictive markers of IDDM, see for example, Bell et al., (*Diabetes* 33:176–83, 1984); Sheehy et al., (*J. Clin. Invest.* 83:830–35, 1989); and Bingley et al., (*Diabetes* 43: 1304–10, 1994). There is therefore a need in the art for autoantigens that would serve to improve detection and diagnosis of IDDM. The present invention fulfills this need by providing novel autoantigens as well as related compositions and methods. The autoantigens of the present invention represent a new β-cell antigen. The present invention also provides other, related advantages.

SUMMARY OF THE INVENTION

The present invention provides an isolated polynucleotide which forms an immune complex with an autoantibody from a patient at risk of or predisposed to develop IDDM, comprising a DNA segment encoding a mammalian islet cell antigen polypeptide of SEQ ID NO:16 from Leu, amino acid residue 636 to Gln, amino acid residue 1012. The invention also provides a mammalian islet cell antigen polypeptide of SEQ ID NO:22 from Leu, amino acid residue 442 to Gln, amino acid residue 818. The invention also provides allelic variants of these polypeptides. Within one aspect of the invention, the isolated polynucleotide encodes a mammalian islet cell antigen polypeptide of SEQ ID NO:22 from Phe, amino acid residue 418, to Gln, amino acid residue 818. Within another aspect of the invention, the isolated polynucleotide encodes a mammalian islet cell antigen polypeptide of SEQ ID NO:16 from Phe, amino acid residue 612, to Gln, amino acid residue 1012. The invention further provides allelic variants of these polypeptides. Within another aspect, the isolated polynucleotide encoding a polypeptide of SEQ ID NO:16 from Ala, amino acid residue 1, to Gln, amino acid residue 1012. Within another aspect, the isolated polynucleotide encoding a polypeptide of SEQ ID NO:22 from His, amino acid residue 1, to Gln, amino acid residue 818. The invention further provides allelic variants of these polypeptides. Within another aspect, the isolated polynucleotide is a DNA molecule comprising a coding sequence corresponding to SEQ ID NO:21 from nucleotide 1325 to nucleotide 2455. In still another aspect, the DNA molecule comprises a coding sequence corresponding to SEQ ID NO:15 from nucleotide 1909 to nucleotide 3039. The invention also provides allelic variants of these molecules. The invention further provides complements of polynucleotide molecules which specifically hybridize to these molecules. In yet another aspect, the isolated polynucleotide is a DNA molecule comprising a coding sequence corresponding to SEQ ID NO:21 from nucleotide 1254 to nucleotide 2455. Within another aspect, the isolated polynucleotide is a DNA molecule comprising a coding sequence corresponding to SEQ ID NO:15 from nucleotide 1837 to nucleotide 3039. The invention also provides allelic variants of these molecules. The invention further provides complements of polynucleotide molecules which specifically hybridize to these molecules. In still another aspect, the DNA molecule comprises a coding sequence corresponding to SEQ ID NO:15 from nucleotide 4 to nucleotide 3039. In still another aspect, the DNA molecule comprises a coding sequence corresponding to SEQ ID NO:21 from nucleotide 2 to nucleotide 2455. The invention also provides allelic variants of these molecules. The invention further provides complements of polynucleotide molecules which specifically hybridize to these molecules. The invention also provides an isolated polynucleotide molecule which encodes a complete coding sequence of a mammalian islet cell antigen polypeptide comprising the sequence of SEQ ID NO:22 from Leu, amino acid residue 442 to Arg, amino acid residue 738. The invention also provides mammalian islet cell antigens that are primate islet cell antigens.

The invention also provides DNA constructs comprising a first DNA segment encoding a human islet cell antigen polypeptide operably linked to additional DNA segments required for the expression of the first DNA segment. The invention further provides a first DNA segment that is an isolated polynucleotide molecule encoding a human islet cell antigen polypeptide comprising the amino acid sequence of SEQ ID NO:22 from Leu, amino acid residue 442 to Gln, amino acid residue 818. The invention also provides a first DNA segment that is an isolated polynucleotide molecule encoding a human islet cell antigen polypeptide comprising the amino acid sequence of SEQ ID NO:22 from Leu, amino acid residue 442 to Gln, amino acid residue 818. Within another aspect, the invention provides a first DNA segment that is an isolated polynucleotide molecule encoding a human islet cell antigen polypeptide comprising the amino acid sequence of SEQ ID NO:22 from His, amino acid residue 1, to Gln, amino acid residue 818. The invention further provides host cells containing such DNA constructs, as well as methods for producing human islet cell antigen polypeptides comprising the steps of culturing such host cell and isolating the human islet cell antigen polypeptide.

The invention further provides isolated mammalian islet cell antigen polypeptides, wherein said isolated mammalian islet cell antigen polypeptide forms an immune complex with an autoantibody from a patient at risk of or predisposed to develop IDDM comprising the amino acid sequence of SEQ ID NO:22 from Leu, amino acid residue 442 to Gln, amino acid residue 818. The invention further provides isolated mammalian islet cell antigen polypeptides comprising the amino acid sequence of SEQ ID NO:16 from Leu, amino acid residue 636 to Gln, amino acid residue 1012.

The invention also provides isolated polypeptides of SEQ ID NO:16 from Phe, amino acid residue 612 to Gln, amino acid residue 1012. The invention also provides isolated polypeptides of SEQ ID NO:22 from Phe, amino acid residue 418, to Gln, amino acid residue 818. The invention further provides isolated polypeptides of SEQ ID NO:16 from Ala, amino acid residue 1 to Gln, amino acid residue 1012. The invention also provides isolated polypeptides of SEQ ID NO:22 from His, amino acid residue 1, to Gln, amino acid residue 818. The invention further provides allelic variants of these polypeptides. The invention still further provides an isolated polypeptide which is a full length mammalian islet cell antigen protein comprising the sequence of SEQ ID NO:22 from Leu, amino acid residue 442 to Arg, amino acid residue 738. The invention also provides mammalian islet cell antigens that are primate islet cell antigens.

Within yet another aspect of the invention is provided a method for determining the presence of an autoantibody to a human islet cell antigen polypeptide in a biological sample, comprising the steps of contacting the biological sample with the human islet cell antigen polypeptide, which comprises an amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gln, amino acid residue 818, a polypeptide of SEQ ID NO:22 from His, amino acid residue 1 to Gln, amino acid residue 818, and allelic variants thereof, under conditions conducive to immune complex formation, and detecting the presence of immune complex formation between the human islet cell antigen polypeptide and the autoantibody to a human islet cell antigen, thereby determining the presence of autoantibodies to the human islet cell antigen in the biological sample. The invention further provides human islet cell antigen polypeptides that are detectably labeled.

Within a further embodiment the invention provides a method for predicting the clinical course of diabetes in a patient, comprising testing a biological sample from a patient for the presence of human islet cell antigen polypeptides comprising the amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gln, amino acid residue 818, a polypeptide of SEQ ID NO:22 from His, amino acid residue 1 to Gln, amino acid residue 818, and allelic variants thereof, wherein the polypeptide forms an immune complex with an autoantibody from a patient at risk of or predisposed to develop IDDM, and classifying the patient for clinical course of diabetes based on the presence or absence of human islet cell antigens in the sample. The invention further provides a method of predicting the clinical course of IDDM by testing one or more additional predictive markers associated with risk of or protection from IDDM. The invention provides methods of predicting the clinical course where the predictive marker is an autoantibody to an antigen selected from the group consisting of GAD65, IA-2/ICA512 or insulin. The invention also provides methods wherein the predictive marker is a genotype selected from the group consisting of HLA DR and HLA DQ. The invention also provides methods wherein the predictive marker is a polymorphic region in the 5' flanking region of a human insulin gene.

The invention also provides a method for treating a patient to prevent an autoimmune response to a human islet cell antigen polypeptide comprising inducing immunological tolerance in the patient by administering a mammalian islet cell antigen polypeptide comprising the amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gin, amino acid residue 818, a polypeptide of SEQ ID NO:22 from His, amino acid residue 1 to Gln, amino acid residue 818, and allelic variants thereof, that specifically binds a human islet cell antigen receptor on immature or mature T or B lymphocytes.

The invention also provides oligonucleotide probes of at least about 16 nucleotides, wherein which the oligonucleotide is at least 85% homologous to a sequence of the mammalian islet cell antigen DNA sequence of SEQ ID Nos:15 or 21.

The invention further provides isolated antibodies which specifically bind to human islet cell antigen polypeptides which comprise the amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gln, amino acid residue 818, a polypeptide of SEQ ID NO:22 from His, amino acid residue 1 to Gln, amino acid residue 818, and allelic variants thereof. Within another aspect, the invention provides monoclonal antibodies. Within yet another aspect, the invention provides a hybridoma which produces the monoclonal antibody.

The invention also provides a diagnostic kit for use in detecting autoantibodies to pancreatic β-islet cells, comprising a container containing an islet cell antigen polypeptide comprising an amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gln, amino acid residue 818, a polypeptide of SEQ ID NO:22 from His, amino acid residue 1 to Gln, amino acid residue 818, and allelic variants thereof, wherein the polypeptide forms an immune complex with autoantibodies from a patient at risk of or predisposed to develop IDDM, and one or more containers containing additional reagents.

Within another embodiment of the invention is provided a pharmaceutical composition comprising an islet cell antigen comprising an amino acid sequence selected from the group consisting of a polypeptide of SEQ ID NO:22 from Leu, amino acid residue 442 to Gln, amino acid residue 81, a polypeptide of SEQ ID NO:22 from Phe, amino acid residue 418 to Gln, amino acid residue 818, a polypeptide of SEQ ID NO:22 from His, amino acid residue 1 to Gln, amino acid residue 818, and allelic variants thereof, in combination with a pharmceutically acceptable carrier or vehicle.

Within a further embodiment of the invention is provided a method for monitoring the disease state in a patient comprising testing a biological sample from a patient for the presence of human islet cell antigen post-translationally modified polypeptides, determining the concentration of the peptides and correlating the peptide levels in the sample with the disease state in the patient. The invention provides that the human islet cell antigen post-translationally modified polypeptide comprises the sequence of SEQ ID NO:22 from His, amino acid residue 1 to Glu, amino acid residue 227. The invention further provides that the biological sample is plasma or serum.

Within yet a further embodiment, the invention provides a method for monitoring the disease state in a patient comprising exposing T cells to islet cell antigen 1851 peptides, detecting T and correlating T cell reactivity with disease state. The invention provides that the T cells are from peripheral blood mononuclear cells from a prediabetic patient. The invention further provides that the disease state is conversion from prediabetes to diabetes.

DETAILED DESCRIPTION OF THE INVENTION

Prior to setting forth the invention, it may be helpful to an understanding thereof to set forth definitions of certain terms to be used hereinafter:

Allelic variant—Any of two or more alternative forms of a gene occupying the same chromosomal locus. Allelic variation arises naturally through mutation, and may result in phenotypic polymorphism within populations. Gene mutations can be silent (no change in the encoded polypeptide) or may encode polypeptides having altered amino acid sequence. The term allelic variant is also used herein to denote a protein encoded by an allelic variant of a gene.

Biological sample—A sample that is derived from or contains cells, cell components or cell products, including, but not limited to, cell culture supernatants, cell lysates, cleared cell lysates, cell extracts, tissue extracts, blood plasma, serum, and fractions thereof, from a patient.

Complements of polynucleotide molecules—

Polynucleotide molecules having a complementary base sequence and reverse orientation as compared to a reference sequence. For example, the sequence 5' ATGCACGGG 3' is complementary to 5' CCCGTGCAT 3'.

Immune Complex Formation—A noncovalently bound molecule formed between an antigen and an antibody specific for that antigen, resulting in an extensively cross-linked mass. Conditions conducive to complex formation are known in the art and easily adaptable by those skilled in art, for example, the degree of complex formation is in proportion to the relative amounts of available antigen and antibody. Such complexes can be used, for example, to identify and/or quantify the presence of either antigen or antibody in a biological sample, identify and characterize particular antibodies in tissues and cells, or to stimulate an immune response.

Isolated—When applied to a protein the term "isolated" indicates that the protein is found in a condition other than its native environment, such as apart from blood and animal tissue. In a preferred form, the isolated protein is substantially free of other proteins, particularly other proteins of animal origin. It is preferred to provide the proteins in a highly purified form, i.e. greater than 95% pure, more preferably greater than 99% pure. When applied to a polynucleotide molecule the term "isolated" indicates that the molecule is removed from its natural genetic milieu and is thus free of other extraneous or unwanted coding sequences, and is in a form suitable for use within genetically engineered protein production systems. Such isolated molecules are those that are separated from their natural environment and include cDNA and genomic clones. Isolated DNA molecules of the present invention are free of other genes with which they are ordinarily associated and may include naturally occurring 5' and 3' untranslated regions such as promoters and terminators, the identification of such will be evident to one of ordinary skill in the art (see for example, Dynan and Tijan, *Nature* 316: 774–78, 1985).

Operably linked—Indicates that the segments are arranged so that they function in concert for their intended purposes, e.g., transcription initiates in the promoter and proceeds through the coding segment to the terminator.

The DNA sequences encoding the polypeptides of the present invention were unexpectedly identified during screening of a primate islet cell cDNA library, and human insulinoma cDNA, for autoantigens toward human diabetic sera. Analysis of the macaque cDNA clones revealed a unique, previously unknown islet cell antigen which contained regions of homology to the protein tyrosine phosphatase family, especially the protein tyrosine phosphatase IA2/ICA512. This novel islet cell antigen has been designated 1851 or ICA512β.

The present invention provides islet cell antigen polypeptides which are β-cell autoantigens. These autoantigens were reactive with human prediabetic and diabetic sera. The invention also provides methods for using the islet cell antigen polypeptides for the detection, diagnosis, and treatment of IDDM.

Representative islet cell antigen polypeptides of the present invention comprise the amino acid sequences in SEQ ID NOs:4, 16 or 22 and/or are encoded by polynucleotide sequences comprising the sequences of SEQ ID NOs:3, 15 and 21 and form an immune complex with autoantibodies from a patient at risk of or predisposed to develop IDDM. The islet cell antigen polypeptides of the present invention are preferably from mammals, especially primates including humans. Preferred polypeptides of the present invention include isolated polypeptides selected from the group consisting of a polypeptide of SEQ ID NO:2 from Leu, amino acid residue 265, to Gln amino acid residue 641. The invention also provides polypeptides of SEQ ID NO:2 from Glu, amino acid residue 1, to Gln, amino acid residue 641. The invention further provides macaque polypeptides of SEQ ID NO:16 from Ala, amino acid residue 1 to Gln, amino acid residue 1012 and human polypeptides of SEQ ID NO:22 from Leu, amino acid residue 442 to Gln, amino acid residue 818 and SEQ ID NO:22 from His, amino acid residue 1 to Gln, amino acid residue 818. The invention further provides allelic variants and isolated sequences that are substantially identical to the representative polypeptide sequences of SEQ ID NOs:2, 16 and 22 and their species homologs. The term "substantially identical" is used herein to denote proteins having 50%, preferably 60%, more preferably 70%, and most preferably at least 80%, sequence identity to the representative sequences shown in SEQ ID NO:2, 16 or 22 or its species homologs. Within preferred embodiments, such proteins will be at least 90% identical, and most preferably 95% or more identical, to SEQ ID NO:2, 16 or 22 or their species homologs.

Percent sequence identity is determined by conventional methods. See, for example, Altschul et al., *Bull. Math. Bio.* 48: 603–616, 1986; Pearson and Lipman, *Proc. Natl. Acad. Sci. USA* 85:2444–2448, 1988; and Henikoff and Henikoff, *Proc. Natl. Acad. Sci. USA* 89:10915–10919, 1992. Briefly, two amino acid sequences are aligned to optimize the alignment scores using a gap opening penalty of 10, a gap extension penalty of 1, and the "blosum 62" scoring matrix of Henikoff and Henikoff (ibid.) as shown in Table 1 (amino acids are indicated by the standard one-letter codes). The percent identity of the optimum alignment is then calculated as:

TABLE 1

|   | A | R | N | D | C | Q | E | G | H | I | L | K | M | F | P | S | T | W | Y | V |
|---|---|---|---|---|---|---|---|---|---|---|---|---|---|---|---|---|---|---|---|---|
| A | 4 | | | | | | | | | | | | | | | | | | | |
| R | -1 | 5 | | | | | | | | | | | | | | | | | | |
| N | -2 | 0 | 6 | | | | | | | | | | | | | | | | | |
| D | -2 | -2 | 1 | 6 | | | | | | | | | | | | | | | | |
| C | 0 | -3 | -3 | -3 | 9 | | | | | | | | | | | | | | | |
| Q | -1 | 1 | 0 | 0 | -3 | 5 | | | | | | | | | | | | | | |
| E | -1 | 0 | 0 | 2 | -4 | 2 | 5 | | | | | | | | | | | | | |
| G | 0 | -2 | 0 | -1 | -3 | -2 | -2 | 6 | | | | | | | | | | | | |
| H | -2 | 0 | 1 | -1 | -3 | 0 | 0 | -2 | 8 | | | | | | | | | | | |
| I | -1 | -3 | -3 | -3 | -1 | -3 | -3 | -4 | -3 | 4 | | | | | | | | | | |
| L | -1 | -2 | -3 | -4 | -1 | -2 | -3 | -4 | -3 | 2 | 4 | | | | | | | | | |
| K | -1 | 2 | 0 | -1 | -3 | 1 | 1 | -2 | -1 | -3 | -2 | 5 | | | | | | | | |
| M | -1 | -1 | -2 | -3 | -1 | 0 | -2 | -3 | -2 | 1 | 2 | -1 | 5 | | | | | | | |
| F | -2 | -3 | -3 | -3 | -2 | -3 | -3 | -3 | -1 | 0 | 0 | -3 | 0 | 6 | | | | | | |
| P | -1 | -2 | -2 | -1 | -3 | -1 | -1 | -2 | -2 | -3 | -3 | -1 | -2 | -4 | 7 | | | | | |
| S | 1 | -1 | 1 | 0 | -1 | 0 | 0 | 0 | -1 | -2 | -2 | 0 | -1 | -2 | -1 | 4 | | | | |
| T | 0 | -1 | 0 | -1 | -1 | -1 | -1 | -2 | -2 | -1 | -1 | -1 | -1 | -2 | -1 | 1 | 5 | | | |
| W | -3 | -3 | -4 | -4 | -2 | -2 | -3 | -2 | -2 | -3 | -2 | -3 | -1 | 1 | -4 | -3 | -2 | 11 | | |
| Y | -2 | -2 | -2 | -3 | -2 | -1 | -2 | -3 | 2 | -1 | -1 | -2 | -1 | 3 | -3 | -2 | -2 | 2 | 7 | |
| V | 0 | -3 | -3 | -3 | -1 | -2 | -2 | -3 | -3 | 3 | 1 | -2 | 1 | -1 | -2 | -2 | 0 | -3 | -1 | 4 |

$$\frac{\text{Total number of identical matches}}{[\text{length of the longer sequence plus the number of gaps introduced into the longer sequence in order to align the two sequences}]} \times 100$$

Substantially identical proteins are characterized as having one or more amino acid substitutions, deletions or additions. These changes are preferably of a minor nature, that is conservative amino acid substitutions (see Table 2) and other substitutions that do not significantly affect the folding or activity of the protein; small deletions, typically of one to about 30 amino acids; amidation of the amino- or carboxyl-terminal; and small amino- or carboxyl-terminal extensions, such as an amino-terminal methionine residue, a small linker peptide of up to about 20–25 residues, or a small extension that facilitates purification, such as a polyhistidine tract, an antigenic epitope or a binding domain. See, in general, Ford et al., *Protein Expression and Purification* 2: 95–107, 1991, which is incorporated herein by reference.

TABLE 2

Conservative amino acid substitutions

| | |
|---|---|
| Basic: | arginine |
| | lysine |
| | histidine |
| Acidic: | glutamic acid |
| | aspartic acid |
| Polar: | glutamine |
| | asparagine |
| Hydrophobic: | leucine |
| | isoleucine |
| | valine |
| Aromatic: | phenylalanine |
| | tryptophan |
| | tyrosine |
| Small: | glycine |
| | alanine |
| | serine |
| | threonine |
| | methionine |

Essential amino acids in the polypeptides of the present invention can be identified according to procedures known in the art, such as site-directed mutagenesis or alanine-scanning mutagenesis (Cunningham and Wells, *Science* 244, 1081–85, 1989). In the latter technique, single alanine mutations are introduced at every residue in the molecule, and the resultant mutant molecules are tested for biological activity (e.g. protein tyrosine phosphatase activity, Strueli et al., *EMBO J.* 9: 2399–407, 1990, or binding to autoantibodies in prediabetic or diabetic sera) to identify amino acid residues that are critical to the activity of the molecule. Sites of ligand-receptor interaction can also be determined by analysis of crystal structure as determined by such techniques as nuclear magnetic resonance, crystallography or photoaffinity labeling. See, for example, de Vos et al., *Science* 255:306–12, 1992; Smith et al., *J. Mol. Biol.* 224:899–904, 1992; Wlodaver et al., *FEBS Lett.* 309:59–64, 1992.

Multiple amino acid substitutions can be made and tested using known methods of mutagenesis and screening, such as those disclosed by Reidhaar-Olson and Sauer (*Science* 241:53–57, 1988) or Bowie and Sauer (*Proc. Natl. Acad. Sci. USA* 86:2152–156, 1989). Briefly, these authors disclose methods for simultaneously randomizing two or more positions in a protein, selecting for functional protein, and then sequencing the mutagenized proteins to determine the spectrum of allowable substitutions at each position. These methods allow the rapid determination of the importance of individual amino acid residues in a protein of interest, and can be applied to proteins of unknown structure.

The present invention further provides isolated polynucleotide molecules encoding islet cell antigen polypeptides which form immune complexes with autoantibodies from a patient at risk of or predisposed to develop IDDM. Useful polynucleotide molecules in this regard include mRNA, genomic DNA, cDNA and synthetic DNA. For production of recombinant islet cell antigen polypeptides, cDNA is preferred. The invention provides an isolated polynucleotide molecule wherein the molecule is a DNA molecule comprising a coding sequence corresponding to SEQ ID NO:1 from nucleotide 795 to nucleotide 1922. The invention also provides a DNA molecule comprising a coding sequence corresponding to SEQ ID NO:1 from nucleotide 1 to nucleotide 2168. The invention also provides a DNA molecule comprising a coding sequence corresponding to nucleotide 4 to nucleotide 3039 of SEQ ID NO: 15. The invention also provides DNA molecules from nucleotide 1325 to nucleotide 2455, from nucleotide 1254 to nucleotide 2455 and from nucleotide 2 to nucleotide 2544 of SEQ ID NO:21. The invention also provides allelic variants of the sequences shown in SEQ ID NOs:1, 15 or 21, and polynucleotide molecules that specifically hybridize to allelic variants. Such polynucleotide molecules will hybridize to the representative DNA sequences of SEQ ID NOs:1, 15, 21 or their allelic variants under stringent conditions (Sambrook et al., *Molecular Cloning: A Laboratory Manual, Second Edition*, Cold Spring Harbor, N.Y., 1989). As used herein, the term "stringent conditions" refers to hybridizing conditions that employ low ionic strength and high temperature for washing, for example, 0.015 M NaCl/0.0015 M sodium citrate/0.1% SDS at 50° C.; employ during hybridization a denaturing agent such as formamide, for example, 50% (vol/vol) formamide with 0.1% polyvinylpyrrolidone/50 mM sodium citrate at 42° C.; or employ 50% formamide, 5×SSC (0.75 M NaCl, 0.075M sodium pyrophosphate, 5×Denhardt's solution, sonicated salmon sperm DNA (50 g/ml), 0.1% SDS, and 10% dextran sulfate at 42° C., with washes at 42° C. in 0.2×SSC and 0.1% SDS. Such hybridizable polynucleotide molecules would include genetically engineered or synthetic variants of the representative islet cell antigen polynucleotide sequence, SEQ ID NO: 1, and polynucleotide molecules that encode one or more amino acid substitutions, deletions or additions, preferably of a minor nature, as discussed above. Genetically engineered variants may be obtained by using oligonucleotide-directed site-specific mutagenesis, by use of restriction endonuclease digestion and adapter ligation, polymerase chain reaction (PCR), or other methods well established in the literature (see for example, Sambrook et al., *Molecular Cloning: A Laboratory Manual, Second Edition*, Cold Spring Harbor, N.Y., 1989, and Smith et al., *Genetic Engineering: Principles and Methods*, Plenum Press, 1981; which are incorporated herein by reference). In addition, hybridizable polynucleotide molecules may encompass sequences containing degeneracies in the DNA code wherein host-preferred codons are substituted for the analogous codons in the representative sequences of SEQ ID NOs: 1, 15 and 21.

Analysis of the representative cDNA sequences of SEQ ID NO:1, 15 and 21 and their representative polypeptide sequences of SEQ ID NO:2, 16 and 22, show that they contain regions of homology to transmembrane protein tyrosine phosphatases. Comparison of the human protein tyrosine phosphatase IA-2/ICA512 cDNA and amino acid sequences with those of 1851 suggests that the coding region of macaque 1851 is missing amino-terminal sequence corresponding to approximately 1 amino acid and human 1851 is missing approximately 200 amino acid residues of the amino terminus. To recover the 5' region, cDNA libraries from different tissues can be screened to obtain a full length cDNA, which encodes a full length mammalian islet cell antigen polypeptides. Another option for obtaining the complete coding sequence comprises using 5' RACE (Rapid Amplification cDNA Ends) PCR. RACE is an art recognized PCR-based method for amplifying the 5' ends of incomplete cDNAs, a frequent occurrence in cDNA cloning. To obtain the 5' portion of a cDNA, PCR is carried out on specially prepared cDNA which contains unique anchor sequences, using anchor primers provided with the 5' RACE reagents available from, for example, Clontech, Palo Alto, Calif. and a 3' primer based on known sequence. The 5'-RACE-Ready cDNA can be purchased commercially (Clontech), or prepared according to known methods. A secondary PCR reaction can then be carried out using the anchor primer and a nested 3' primer, according to known methods. Once a full-length cDNA is obtained, it is expressed and analyzed for overall structural similarity to known protein tyrosine phosphatases, and examined for features such as a continuous open reading frame flanked by translation initiation and termination sites and a potential signal sequence.

Transmembrane, or receptor-linked, protein tyrosine phosphatases consist of a conserved cytoplasmic domain which may have one or two (tandemly duplicated) catalytic regions, a single transmembrane domain, a highly variable extracellular domain and a signal peptide. These structural features suggest that receptor-linked protein tyrosine phosphatases would be capable of binding ligand and transducing external signal, but no ligands as of yet have been identified. Based on the representative amino acid sequence of SEQ ID NOs:2 and 15, the macaque 1851 polypeptide has an approximately 611 amino acid extracellular domain, from Ala, amino acid residue 1 to Lys, amino acid residue 611 of SEQ ID NO:16, containing a post translational modification dibasic site, at amino acid residue 423–424, or a tribasic site at amino acid residues 422–424; a 24 amino acid transmembrane domain comprising amino acid residue 241 to amino acid residue 265 of SEQ ID NO:2 or Phe, amino acid residue 612 to Cys, amino acid residue 635 of SEQ ID NO:16 and an approximately 375 amino acid cytoplasmic domain comprising the amino acid residue 265 to amino acid residue 640 of SEQ ID NO:2 or Leu, amino acid residue 636 to Gln, amino acid residue 1012 of SEQ ID NO:16. The representative amino acid sequence of the human islet cell antigen 1851 (SEQ ID NO:22) has 417 amino acids of an extracellular domain, from His, amino acid residue 1 to Lys, amino acid residue 417 of SEQ ID NO:22; a 24 amino acid residue transmembrane domain, from Phe, amino acid residue 418 to Cys, amino acid residue 441, of SEQ ID NO:22; and a 376 amino acid cytoplasmic domain, from Leu, amino acid residue 442 to Gln, amino acid residue 818 of SEQ ID NO:22.

The cytoplasmic domain of 1851 contains many regions that are conserved between members of the protein tyrosine phosphatase family. Within the cytoplasmic domain of protein tyrosine phosphatases is a catalytic region of about 230 amino acids, which contains a highly conserved catalytic core segment of approximately 11 amino acid residues (VHCXAGXXRXG SEQ ID NO:13) where the first three X's are any amino acid, the fourth X is S or T, and the cysteine appears to be essential to the catalytic mechanism (Fischer et al., *Science* 253: 401–06). The catalytic core sequence of the representative macaque 1851 polypeptide sequences of SEQ ID Nos:2 and 16 and human 1851 polypeptide sequence represented by SEQ ID NO:22 differs from other members of the protein tyrosine phosphatase family in that alanine has been replaced by aspartic acid and the second variable amino acid (X) is alanine. 1851, like IA-2/ICA512, has a single catalytic region. Deletion of C-terminal amino acids from the intracellular domain of human islet cell antigen 1851 reduced reactivity with new onset IDDM sera, suggesting this region may play a role in defining an autoantibody epitope. Removal of the C-terminal 27 amino acids decreased reactivity from 19/53 sera (36%) to 10/53 sera (19%), a 47% decrease. Removal of the C-terminal 80 amino acids decreased reactivity further to 9/53 sera (17%), a 53% decrease, and removal of the C-terminal 160 amino acids abolished all recognition by all 53 new onset IDDM sera. This is similar to the reports of one of two described intracellular IA-2/ICA512 autoantibody epitopes (Bonifacio et al., *J. Immunol.* 155:5419–426, 1995). That human islet cell antigens 1851 and human IA-2/ICA512 are each precipitated by sera that do not precipitate the other suggests that each antigen has unique autoantibody epitopes, which is consistent with previous findings regarding the 37 kD and 40 kD tryptic fragments (Payton et al., *J. Clin. Invest.* 96:1506–11, 1995). A comparison between the overall human and macaque islet cell antigen 1851 nucleotide and amino acid sequences shows a 96.2% nucleotide identity and a 94.6% amino acid identity, in particular there was 97% identity within the nucleotide sequence and 98.9% identity within the amino acid sequence of the corresponding cytoplasmic domains, 100% identity within the transmembrane domain. There is 77% amino acid identity within the cytoplasmic domain between the claimed human (SEQ ID NO:22) and macaque (SEQ ID NO:16) islet cell antigen 1851 sequences and the reported human IA-2/ICA512 sequences (Lan et al., ibid.; and Rabin et al., ibid.). Between the full length macaque islet cell antigen 1851 sequence (as represented in SEQ ID Nos: 15 and 16) and rat phogrin sequences (Wasmeier and Hutton, *J. Biol. Chem.* 271:18161–70, 1996) there was less homology, 75.5% identity within the nucleotide sequence and 69.9% identity within the amino acid sequence.

In contrast, there is little homology in the extracellular regions of transmembrane protein tyrosine phosphatases. Some contain Ig-like and/or fibronectin type III repeats (Streuli et al.,*J. Exp. Med.* 168: 1523, 1988; Hariharan et al., *Proc. Natl. Acad. Aci. USA* 88: 11266, 1991); others have glycosylated segments (Sap et al., *Proc. Natl. Acad. Sci. USA* 87:6112, 1990; and Krueger et al., *EMBO J.* 9: 3241, 1990) and a conserved cysteine-rich region (Tonks et al., *J. Biol. Chem.* 265: 10674–80, 1990) (Lan et al. ibid.). There is 31% identity between macaque islet cell antigen 1851 (as represented by SEQ ID NO:15) and IA-2/ICA512 (Lan et al., ibid.; and Rabin et al., ibid.) within the extracellular domain.

The tissue distribution of human islet cell antigen 1851 is generally neuroendocrine. Northern analysis showed strong hybridization to human mRNA from brain and pancreas and weaker hybridization in spinal cord, thyroid, adrenal and GI tract. In situ hybridization using macaque tissues further localized pancreatic and adrenal expression to islets and adrenal medulla, respectively. Northern blot analysis of rat phogrin showed expression in brain, pancreas and α and β cell tumor lines (Wasmeier and Hutton, ibid.); mouse IA-2β in brain, pancreas, stomach and in insulinoma and glucagomoma cell lines (Lu et al., *Proc. Natl. Acad. Sci. USA* 93:2307–11, 1996); human IA-2 in brain, pituitary and pancreas, four insulinoma cell lines and a glioblastoma cell line (Lan et al., ibid.); and human ICA512, brain and pancreas (Rabin et al., ibid.).

Limited trypsinization of IA-2/ICA512 and human islet cell antigen 1851 yielded a 40 kD IA-2/ICA512 fragment and a 37 kD islet cell antigen 1851 fragment. These correspond to the 37 kD and 40 kD tryptic fragments described by Christie et al. (*J. Exp. Med.* 172:789–94, 1990), Payton et al. (*J. Clin. Invest.* 96:1506–11, 1995), Bonifacio et al. (*J. Immunol.* 155:5419–26, 1995), Lu et al. (*Proc. Natl. Acad. Sci. USA* 93:2307–11, 1996) and Wasmeier and Hutton (ibid.).

Members of the protein tyrosine phosphatase family have been shown to display alternative mRNA splicing (Moeller et al., WO 94/21800; Hall et al.,*J. Immunol.* 141: 2781–87, 1988; Johnson et al., *J. Biol. Chem.* 264: 6220–29, 1989; Streuli and Saito, *EMBO J.* 8: 787–96, 1989; Matthews et al., *Proc. Natl. Acad. Sci. USA* 87: 4444–48, 1990; Walton and Dixon, *Ann. Rev. Biochem.* 62: 101–20, 1993; and Pan et al., *J. Biol. Chem.* 268: 19284–91, 1993). Alternative splicing may be important in autoantibody recognition; "inappropriate" splicing could lead to autoimmunity by activating T cells, for example.

The invention provides isolated DNA molecules that are useful in producing recombinant islet cell antigens. As will be evident to one skilled in the art, each individual domain or combinations of the domains may be prepared synthetically or by recombinant DNA techniques for use in the present invention. Thus, the present invention provides the advantage that islet cell antigens are produced in high quantities that may be readily purified using methods known in the art (see generally; Scopes, *Protein Purification*, Springer-Verlag, N.Y., 1982). Alternatively, the proteins of the present invention may be synthesized following conventional synthesis methods, such as the solid-phase synthesis method of Barany and Merrifield (in *The Peptides. Analysis, Synthesis, Biology* Vol. 2, Gross and Meienhofer, eds, Academic Press, NY, pp. 1–284, 1980), by partial solid-phase techniques, by fragment condensation or by classical solution addition.

DNA molecules of the present invention can be isolated using standard cloning methods such as those described by Maniatis et al. (*Molecular Cloning: A Laboratory Manual*, Cold Spring Harbor, N.Y., 1982; which is incorporated herein by reference), Sambrook et al., (*Molecular Cloning: A Laboratory Manual, Second Edition*, Cold Spring Harbor, N.Y., 1989), or Mullis et al. (U.S. Pat. No. 4,683,195) which are incorporated herein by reference. Alternatively, the coding sequences of the present invention can be synthesized using standard techniques that are well known in the art, such as by synthesis on an automated DNA synthesizer.

The sequence of a polynucleotide molecule encoding a representative islet cell antigen polypeptide is shown in SEQ ID NOs: 1, 15 and 21 and the corresponding amino acid sequences are shown in SEQ ID NOs: 2, 16 and 22. Those skilled in the art will recognize that these sequences correspond to one allele of either the macaque or human gene, and that allelic variation is expected to exist. Allelic variants of the DNA sequence shown in SEQ ID NO: 1, 15 and 21 including those containing silent mutations and those in which mutations result in amino acid sequence changes, are within the scope of the present invention, as are proteins which are allelic variants of SEQ ID NO: 2, 16 and 22.

The macaque sequence disclosed herein is useful for isolating polynucleotide molecules encoding islet cell antigen polypeptides from other species ("species homologs"). In particular, the macaque cDNA was used to conduct a sequence search for a human homolog. A match was found as an expressed sequence tag (EST) from a human fetal brain library submitted to the Genbank database (GenBank ID: TO361, clone ID: HFBCV88). This 127 amino acid polypeptide, SEQ ID NO:5, had homology to a region of the cytoplasmic domain of M1.18.5.1 (SEQ ID NO:2) and was used to design PCR primers to clone a 1.1 kD cytoplasmic portion (SEQ ID NOs:6 and 7) of the human 1851 sequence, as described in the examples below. Other preferred species homologs include mammalian homologs such as bovine, canine, porcine, ovine, and equine proteins. Methods for using sequence information from a first species to clone a corresponding polynucleotide sequence from a second species are well known in the art. See, for example, Ausubel et al., eds., *Current Protocols in Molecular Biology*, John Wiley and Sons, Inc., NY, 1987.

DNA molecules of the present invention or portions thereof may be used as probes, for example, to directly detect 1851 sequences in cells or biological samples. Such DNA molecules are generally synthetic oligonucleotides, but may be generated from cloned cDNA or genomic sequences and will generally comprise at least about 16 nucleotides, more often from about 17 nucleotides to about 25 or more nucleotides, sometimes 40 to 60 nucleotides, and in some instances a substantial portion or even the entire 1851 gene or cDNA. The synthetic oligonucleotides of the present invention have at least 85% identity to a representative macaque or human 1851 DNA sequence (SEQ ID Nos:1, 15 and 21) or their complements. For use as probes, the molecules are labeled to provide a detectable signal, such as with an enzyme, biotin, a radionuclide, fluorophore, chemiluminescer, paramagnetic particle, etc., according to methods known in the art. Probes of the present invention may also be used in diagnostic methods to detect autoantibodies in diabetic and prediabetic sera.

DNA molecules used within the present invention may be labeled and used in a hybridization procedure similar to the Southern or dot blot. As will be understood by those skilled in the art, conditions that allow the DNA molecules of the present invention to hybridize to the representative DNA sequence of SEQ ID NO:1, 15 or 21 or their allelic variants may be determined by methods well known in the art (reviewed, for example, by Sambrook et al. *Molecular Cloning: A Laboratory Manual, Second Edition*, Cold Spring Harbor, N.Y., 1989; which is incorporated herein by reference). Those skilled in the art will be capable of varying hybridization conditions (i.e. stringency of hybridization) of the DNA molecules as appropriate for use in the various procedures by methods well known in the literature (see, for example, Sambrook et al., ibid., pages 11.45–11.53). The higher the stringency of hybridization, the lower the number of mismatched sequences detected. Alternatively, lower stringency will allow related sequences to be identified.

Alternatively, allelic variants may be identified using DNA molecules of the present invention and, for example, the polymerase chain reaction (PCR) (disclosed by Saiki et al., *Science* 239: 487, 1987; Mullis et al., U.S. Pat. No. 4,686,195; and Mullis et al., U.S. Pat. No. 4,683,202) to amplify DNA sequences, which are subsequently detected by their characteristic size on agarose gels or which may be sequenced to detect sequence abnormalities.

DNA molecules encoding the islet cell antigen polypeptides of the present invention may be inserted into DNA constructs. As used within the context of the present invention a DNA construct is understood to refer to a DNA molecule, or a clone of such a molecule, either single- or double-stranded, which has been modified through human intervention to contain segments of DNA combined and juxtaposed in a manner that would not otherwise exist in nature. DNA constructs of the present invention comprise a first DNA segment encoding an islet cell antigen polypeptide operably linked to additional DNA segments required for the expression of the first DNA segment. Within the context of the present invention, additional DNA segments will generally include promoters and transcription terminators, and may further include enhancers and other elements. One or more selectable markers may also be included. DNA constructs useful for expressing cloned DNA segments in a variety of prokaryotic and eukaryotic host cells can be prepared from readily available components or purchase from commercial suppliers.

In general, a DNA sequence encoding a protein of the present invention is operably linked to a transcription promoter and terminator within a DNA construct. The construct will commonly contain one or more selectable markers and one or more origins of replication, although those skilled in the art will recognize that within certain systems selectable markers may be provided on separate vectors, and replication of the exogenous DNA may be provided by integration into the host cell genome. Selection of promoters, terminators, selectable markers, vectors and other elements is a matter of routine design within the level of ordinary skill in the art. Many such elements are described in the literature and are available through commercial suppliers.

In one embodiment the first DNA segment is an isolated polynucleotide molecule encoding a mammalian islet cell antigen polypeptide comprising the amino acid sequence of SEQ ID NO:4, wherein the polypeptide forms an immune complex with autoantibodies from a patient at risk of or predisposed to IDDM. In another embodiment, the first DNA segment is an isolated polynucleotide encoding a polypeptide of SEQ ID NO:2 from Leu, amino acid residue 265 to Gln, amino acid residue 641. In another embodiment, the first DNA segment is an isolated polynucleotide encoding a polypeptide of SEQ ID NO:2 from Ser, amino acid residue 1, to Gln, amino acid residue 641.

Within yet another embodiment, the first DNA segment is an isolated polynucleotide encoding a polypeptide of SEQ ID NO:22 from Leu, amino acid residue 442 to Gln, amino acid residue 818. In another embodiment, the first DNA segment is an isolated polynucleotide encoding a polypeptide of SEQ ID NO:16 from Ala, amino acid residue 1 to Gln, amino acid residue 1012.

The proteins of the present invention can be produced in genetically engineered host cells according to conventional techniques. Suitable host cells are those cell types that can be transformed or transfected with exogenous DNA and grown in culture, and include bacteria, fungal cells, and cultured higher eukaryotic cells. Techniques for manipulating cloned DNA molecules and introducing exogenous DNA into a variety of host cells are disclosed by Sambrook et al., *Molecular Cloning: A Laboratory Manual*, 2nd ed., Cold Spring Harbor Laboratory Press, Cold Spring Harbor, N.Y., 1989, and Ausubel et al., ibid., which are incorporated herein by reference.

To direct a protein of the present invention into the secretory pathway of the host cells, a secretory signal sequence (also known as a leader sequence, prepro sequence or pre sequence) is provided in the expression vector. The secretory signal sequence is joined to the DNA sequence encoding a protein of the present invention in the correct reading frame. Secretory signal sequences are commonly positioned 5' to the DNA sequence encoding the protein of interest, although certain signal sequences may be positioned elsewhere in the DNA sequence of interest (see, e.g., Welch et al., U.S. Pat. No. 5,037,743; Holland et al., U.S. Pat. No. 5,143,830). The secretory signal sequence may be that normally associated with a protein of the present invention, or may be from a gene encoding another secreted protein.

Cultured mammalian cells are also preferred hosts within the present invention. A preferred vector system for use in the present invention is the pZCEP vector system as disclosed by Jelineck et al., *Science*, 259: 1615–16, 1993. Methods for introducing exogenous DNA into mammalian host cells include calcium phosphate-mediated transfection (Wigler et al., *Cell* 14:725, 1978; Corsaro and Pearson, *Somatic Cell Genetics* 7:603, 1981: Graham and Van der Eb, *Virology* 52:456, 1973), electroporation (Neumann et al., *EMBO J.* 1:841–845, 1982), DEAE-dextran mediated transfection (Ausubel et al., eds., *Current Protocols in Molecular Biology*, John Wiley and Sons, Inc., NY, 1987), and cationic lipid transfection using commercially available reagents including the Boehringer Mannheim Transfection-Reagent (N-[1-(2,3-Dioleoyloxy)propyl]-N,N,N-trimethyl ammoniummethylsulfate; Boehringer Mannheim, Indianapolis, Ind.) or LIPOFECTIN~reagent (N-[1-(2,3-Dioleyloxy)propyl]-N, N,N-trimethylammonium chloride and dioeleoyl phosphatidylethanolamine; GIBCO-BRL, Gaithersburg, Md.) using the manufacturer-supplied directions, which are incorporated herein by reference. The production of recombinant proteins in cultured mammalian cells is disclosed, for example, by Levinson et al., U.S. Pat. No. 4,713,339; Hagen et al., U.S. Pat. No. 4,784,950; Palmiter et al., U.S. Pat. No. 4,579,821; and Ringold, U.S. Pat. No. 4,656,134, which are incorporated herein by reference. Preferred cultured mammalian cells include the COS-1 (ATCC No. CRL 1650), COS-7 (ATCC No. CRL 1651), BHK (ATCC No. CRL 1632), BHK 570 (ATCC No. CRL 10314), 293 (ATCC No. CRL 1573; Graham et al., *J. Gen. Virol.* 36:59–72, 1977) and Chinese hamster ovary (e.g. CHO-K1; ATCC No. CCL 61) cell lines. Additional suitable cell lines are known in the art and available from public depositories such as the American Type Culture Collection, Rockville, Md. In general, strong transcription promoters are preferred, such as promoters from SV-40 or cytomegalovirus.

Prokaryotic cells can also serve as host cells for use in carrying out the present invention. Particularly preferred are strains of the bacteria *Escherichia coli*, although Bacillus and other genera are also useful. Techniques for transforming these hosts and expressing foreign DNA sequences cloned therein are well known in the art (see, e.g., Sambrook et al., ibid.). When expressing the proteins in bacteria such as *E. coli*, the protein may be retained in the cytoplasm, typically as insoluble granules, or may be directed to the periplasmic space. In the former case, the cells are lysed, and the granules are recovered and denatured using, for example, guanidine isothiocyanate. The denatured protein is then refolded by diluting the denaturant. In the latter case, the protein can be recovered from the periplasmic space in a soluble form.

Fungal cells are also suitable as host cells. For example, Saccharomyces ssp., *Hansenula polymorpha, Schizosaccharomyces pombe, Kluyveromyces lactis, Kluyveromyces fragilis, Ustilago maydis, Pichia pastoris, Pichia guillermondii, Pichia methanolica*, and *Candida maltosa* transformation systems are known in the art. See, for example, Kawasaki, U.S. Pat. No. 4,599,311, Kawasaki et al., U.S. Pat. No. 4,931,373, Brake, U.S. Pat. No. 4,870,008; Welch et al., U.S. Pat. No. 5,037,743; and Murray et al., U.S. Pat. No. 4,845,075, Gleeson et al., *J. Gen. Microbiol.* 132:3459–3465, 1986 and Cregg, U.S. Pat. No. 4,882,279. Aspergillus cells may be utilized according to the methods of McKnight et al., U.S. Pat. No. 4,935,349, which is incorporated herein by reference. Methods for transforming *Acremonium chrysogenum* are disclosed by Sumino et al., U.S. Pat. No. 5,162,228, which is incorporated herein by reference.

Other higher eukaryotic cells can also be used as hosts, including insect cells, plant cells and avian cells. Transformation of insect cells and production of foreign proteins therein is disclosed by Guarino et al., U.S. Pat. No. 5,162,222 and Bang et al., U.S. Pat. No. 4,775,624, which are incorporated herein by reference. The use of *Agrobacterium rhizogenes* as a vector for expressing genes in plant cells has been reviewed by Sinkar et al., *J. Biosci. (Bangalore)* 11:47–58, 1987.

Drug selection is generally used to select for cultured mammalian cells into which foreign DNA has been inserted. Such cells are commonly referred to as "transfectants". Cells that have been cultured in the presence of the selective agent and are able to pass the gene of interest to their progeny are referred to as "stable transfectants." A preferred selectable marker is a gene encoding resistance to the antibiotic neomycin. Selection is carried out in the presence of a neomycin-type drug, such as G-418 or the like. Selection systems may also be used to increase the expression level of the gene of interest, a process referred to as "amplification." Amplification is carried out by culturing transfectants in the presence of a low level of the selective agent and then increasing the amount of selective agent to select for cells that produce high levels of the products of the introduced genes. A preferred amplifiable selectable marker is dihydrofolate reductase, which confers resistance to methotrexate.

Transformed or transfected host cells are cultured according to conventional procedures in a culture medium containing nutrients and other components required for the growth of the chosen host cells. A variety of suitable media, including defined media and complex media, are known in the art and generally include a carbon source, a nitrogen source, essential amino acids, vitamins and minerals. Media may also contain such components as growth factors or serum, as required. The growth medium will generally select for cells containing the exogenously added DNA by, for example, drug selection or deficiency in an essential nutrient which is complemented by the selectable marker carried on the expression vector or co-transfected into the host cell.

The recombinant islet cell antigen polypeptides expressed using the methods described herein are isolated and purified by conventional procedures, including separating the cells from the medium by centrifugation or filtration, precipitating the proteinaceous components of the supernatant or filtrate by means of a salt, e.g. ammonium sulfate, purification by a variety of chromatographic procedures, e.g. ion exchange chromatography or affinity chromatography, or the like. Methods of protein purification are known in the art (see generally, Scopes, R., *Protein Purification*, Springer-Verlag, N.Y. (1982), which is incorporated herein by reference) and may be applied to the purification of the recombinant proteins of the present invention. Substantially pure recombinant islet cell antigen polypeptides of at least about 50% is preferred, at least about 70–80% more preferred, and 95–99% or more homogeneity most preferred, particularly for pharmaceutical uses. Once purified, partially or to homogeneity, as desired, the recombinant islet cell antigen polypeptides may then be used diagnostically, therapeutically, etc. as further described below.

Recombinant 1851 polypeptides can also be produced by expressing islet cell antigen DNA fragments, such as fragments generated by digesting an islet cell antigen cDNA at convenient restriction sites. The isolated recombinant polypeptides or cell-conditioned media are then assayed for activity as described in the examples below. Alternatively, the proteins of the present invention may be synthesized following conventional synthesis methods such as the solid-phase synthesis using the method of Barany and Merrifield (in *The Peptides. Analysis, Synthesis, Biology* Vol. 2, Gross and Meienhofer, eds, Academic Press, NY, pp. 1–284, 1980, which are incorporated herein by reference), by partial solid-phase techniques, by fragment condensation or by classical solution addition. Short polypeptide sequences, or libraries of overlapping peptides, usually from about 6 up to about 35 amino acids, which correspond to selected islet cell antigen polypeptide regions can be readily synthesized and then screened in screening assays designed to identify peptides having a desired activity, such as domains which are responsible for or contribute to binding activity, immunodominant epitopes (particularly those recognized by autoantibodies), and the like.

Although the use of recombinant 1851 polypeptides is preferred within the methods of the present invention, 1851 polypeptides may also be prepared from cells that naturally produce 1851 protein (such as islet cells). For example, 1851 polypeptides may be prepared from islet cells by isolation of a membrane fraction. This 1851-enriched fraction is then used to detect autoantibodies to 1851 in prediabetic and diabetic sera.

Islet cell antigen polypeptides produced according to the present invention can be used diagnostically, in the detection and quantitation of autoantibodies in a biological sample, that is, any sample derived from or containing cells, cell components or cell products, including, but not limited to, cell culture supernatants, cell lysates, cleared cell lysates, cell extracts, tissue extracts, blood plasma, serum, and fractions thereof. By means of having islet cell antigen polypeptides which specifically bind to autoantibodies in prediabetic and diabetic sera, the presence or absence of such autoantibodies can be determined, and the concentration of such autoantibodies in an individual can be measured. This information can then be used to monitor the progression or regression of the potentially harmful autoantibodies in individuals at risk of, or with a predisposition to develop IDDM, and would be useful for predicting the clinical course of the disease in a patient. The assay results can also find use in monitoring the effectiveness of therapeutic measures for treatment of IDDM or related diseases.

As will be recognized by those skilled in the art, numerous types of immunoassays are available for use in determining the presence of autoantibodies. For instance, direct and indirect binding assays, competitive assays, sandwich assays, and the like, as are generally described in, e.g., U.S. Pat. Nos. 4,642,285; 4,376,110; 4,016,043; 3,879,262; 3,852,157; 3,850,752; 3,839,153; 3,791,932; and Harlow and Lane, *Antibodies, A Laboratory Manual*, Cold Spring Harbor Publications, N.Y., 1988, each incorporated herein by reference. In one assay format, autoantibodies directed to the polypeptides of the present invention are quantified directly by measuring the binding of autoantibodies in a biological sample to recombinant or synthetic islet cell antigen polypeptides. The biological sample is contacted with at least one islet cell antigen polypeptide of the invention under conditions conducive to immune complex formation. The immune complexes formed between the islet cell antigen polypeptide and the antibodies are then detected, and the presence and quantity of autoantibodies can then be used to diagnose or direct treatment of IDDM. The immune complexes can be detected by means of antibodies that bind to the islet cell antigen of the present invention or by labeling the polypeptide as described below. Separation steps (e.g., washes) may be necessary in some cases to distinguish specific binding over background. In another format, the serum level of a patient's autoantibodies to the islet cell antigen polypeptides in serum can be measured by competitive binding with labeled or unlabeled antibodies to the islet cell antigen polypeptides of the present invention. Unlabeled 1851 polypeptides can be used in combination with labeled antibodies that bind to human antibodies or to islet cell antigens. Alternatively, the islet cell antigen polypeptide can be directly labeled. A wide variety of labels can be employed, such as radionuclides, particles (e.g., gold, ferritin, magnetic particles, red blood cells), fluors, enzymes, enzyme substrates, enzyme cofactors, enzyme inhibitors, ligands (particularly haptens), chemiluminescers, biotin and other compounds that provide for the detection of the labeled polypeptide or protein. For example, an 1851 polypeptide can be radiolabeled using conventional methods such as in vitro transcription and translation. Radiolabeled 1851 polypeptide is combined with patient serum under conditions suitable for immune complex formation. Immune complexes are then separated, such as by binding to protein A. Precipitated 1851 polypeptides are then quantitated by conventional methods, such as gel electrophoresis, fluorography, densitometry or by direct counting of immunoprecipitated, radiolabeled antigen. The amount of 1851 polypeptide precipitated by test sera can be statistically compared to mean counts precipitated by healthy control sera, each measured separately. In an alternative format, an 1851 polypeptide antigen, labeled with biotin, is combined with patient serum under conditions suitable for immune complex formation. The serum is then transferred to a protein A-coated container, such as a well of an assay plate, and the container is allowed to stand so that immune complexes can form. The container is then washed, and streptavidin, conjugated to a suitable enzyme (e.g. alkaline phosphatase), is added. A chromogenic substrate is then added, and the presence of 1851 polypeptide autoantibodies in the sample is indicated by a color change. Additional assay formats will be evident to those skilled in the art.

Thus, autoantibodies to islet cell antigen polypeptides can be identified and, if desired, extracted from a patient's serum by binding to 1851 polypeptides of the present invention. The islet cell antigen polypeptides may be attached, e.g., by adsorption, to an insoluble or solid support, such as ELISA microtiter well, microbead, filter membrane, insoluble or precipitable soluble polymer, etc. to function as an affinity resin. The captured autoantibodies can then be identified by several methods. For example, antisera or monoclonal antibodies to the antibodies can be used. These antisera or monoclonal antibodies are typically non-human in origin, such as rabbit, goat, mouse, etc. These anti-antibodies can be detected directly if attached to a label such as $^{125}$I, enzyme, biotin, etc., or can be detected indirectly by a labeled secondary antibody made to specifically detect the anti-antibody.

The diagnostic methods of the present invention can be used in conjunction with other known assays and diagnostic techniques (see for example, WO 95/07464, incorporated herein by reference in its entirety). Such other assays and techniques include measurement of body mass index (BMI), defined as the quotient of the patient's weight in kg divided by the square of height in meters; C-peptide level (Heding, *Diabetologia* 11: 541–548 (1975); Landin-Olsson et al., *Diabetologia* 33: 561–568 (1990)); or one or more additional diabetes-associated autoantibodies, genotypes or loci. A low BMI (i.e. less than about 25) in combination with other indicators is suggestive of type I diabetes. BMI is thus a useful indicator for distinguishing type I from type II diabetes. C-peptide level can be measured using standard methods, such as that of Heding (ibid.), in which insulin and proinsulin are removed from serum and C-peptide is measured in the resulting insulin-free fraction radioimmunologically.

The islet cell antigen polypeptides of the current invention can also be used to assess T cell reactivity, as a method for monitoring the disease state in a patient. Mammalian islet cell antigen 1851 peptides will generally comprise at least about 12 amino acids, and more often from about 15 amino acids to about 20 or more amino acids. In some instances, a substantial portion or domain or even the entire 1851 protein, can be used to assess T cell reactivity in peripheral blood mononuclear cells (PBMNCs) from prediabetics. Methods for detecting such in vitro activity are known in the art, including a proliferation assay measuring $^3$H-thymidine incorporation, analysis of activation markers, such as CD69, or measuring cytokine production, such as IL-2. Correlations can be drawn between T cell reactivity to islet cell antigen 1851 and conversion from prediabetes to diabetes. This correlation would be consistent with the appearance of autoantibodies to islet cell antigen peptides late in prediabetes (Christie et al., *Diabetes* 43:1254–59, 1994).

Mammalian cells, such as COS cells or L cells, may also be transfected with appropriate Class I or Class II alleles specific for the islet cell antigen of the present invention. Such MHC molecules may be soluble or membrane bound, and the 1851 antigenic polypeptide may be recombinantly tethered to the N-terminal region of the α or β chain using a flexible linker containing, for example, repeating glycine residues separated by a serine residue, such that the antigenic peptide binds to the MHC molecule and is properly presented to the T cell. Alternatively, the antigenic peptide may be exogenously loaded into the MHC peptide binding grove. The MHC-antigenic peptide complex can then be used to assess the reactivity of peripheral blood T cells derived from prediabetic or diabetic patients. This reactivity may be assessed by methods known in the art, such as $^3$H thymidine incorporation, cytokine production or cytolysis. Alternatively, islet cell antigen expressed in microorganisms can be "fed" to peripheral blood mononuclear cells (PBMN). The antigen-fed cells can then be used to stimulate peripheral blood T cells derived from diabetics or prediabetics.

The islet cell antigen polypeptides are also contemplated to be advantageous for use as immunotherapeutics to induce immunological tolerance or nonresponsiveness (anergy) to 1851 polypeptide autoantigens in patients predisposed or already mounting an immune response to 1851 polypeptide autoantigens of the islet β-cells. This therapy can take the form of autoantigenic 1851 peptides bound to an appropriate MHC Class I or Class II molecule as described above. The therapy can also be in the form of oral tolerance (Weiner et al., *Nature* 376: 177–80, 1995), or IV tolerance, for example. The use of polypeptide antigens in suppression of autoimmune disease is disclosed by Wraith, et al., (*Cell* 59: 247–55, 1989). Tolerance can be induced in patients, although conditions for inducing such tolerance will vary according to a variety of factors. In a neonate, tolerance can be induced by parenteral injection of an islet cell antigenic polypeptide, either with recombinant polypeptide or synthetic antigen, or more conveniently by oral administration in an appropriate formulation. The precise amount of administration, its mode and frequency of dosages will vary.

To induce immunological tolerance to the islet cell autoantigens in an adult susceptible to or already suffering from a islet cell antigen related disease such as IDDM, the precise amounts and frequency of administration will also vary, for adults about 1 to 1,000 mg/kg can be administered by a variety of routes, such as parenterally, orally, by aerosols, intradermal injection, etc. For neonates the doses will generally be higher than those administered to adults; e.g. 100 to 1,000 mg/kg.

The islet cell antigen 1851 polypeptides will typically be more tolerogenic when administered in a soluble form rather than an aggregrated or particulate form. Persistence of an islet cell antigen polypeptide of the invention is generally needed to maintain tolerance in an adult, and thus may require more frequent administration of the antigen, or its administration in a form which extends the half-life of the islet cell antigen. See for example, Sun et al. (*Proc. Natl. Acad. Sci. USA* 91: 10795–99, 1994).

The islet cell antigen polypeptides described herein are also contemplated to be advantageous for use as immunotherapeutics in treating longer term IDDM patients that have been identified by autoantibody testing at the time of clinical non-insulin dependent diabetes mellitus (NIDDM) diagnosis. Intervention in these patients may be especially effective, perhaps due to the slowly progressive nature of their β cell destruction. Since the numbers of such patients is nearly the same as those with classical childhood IDDM, there is a need for such therapeutic intervention (Hagopian et al., *J. Clin. Invest.* 91:368–74; 1993; Harris and Robbins, *Diabetes Care* 17:1337–40, 1994; and Kobayashi et al., *Diabetes* 45:622–26, 1996).

The N-terminal domain of islet cell antigen 1851 is expected to be inside the insulin secretory granule. The islet cell antigen polypeptides of the current invention contain post translational modification sites within the N-terminal domain. A dibasic site or tribasic site at amino acid residues 228–230 (Arg-Lys-Lys) in SEQ ID NO:22 and amino acid residues 422–424 (Arg-Lys-Lys) in SEQ ID NO:16 could result in cleavage of a 420 amino acid post-translationally modified mammalian islet cell antigen polypeptide from the islet cell antigen 1851 polypeptide. All or part of this cleaved polypeptide may be released from the β cell via either the constitutive secretory pathway for granule halo components, or via the regulated pathway involved in insulin release. Detection and quantitation of post translationally modified polypeptides in a biological sample (that is, any sample derived from or containing cells, cell components or cell products, including, but not limited to, cell culture supernatants, cell lysates, cleared cell lysates, cell extracts, tissue extracts, blood plasma, serum, and fractions thereof) can be used diagnostically to monitor disease state in a patient. The presence or absence of such polypeptides in prediabetic and diabetic sera can be determined, for example by radioimmunoassay, and the concentration of such polypeptides in such an individual serum sample can be measured. This information can then be used, for example, to monitor insulin secretory activity, such as β cell insulin secretory rates; or to indicate altered β cell physiology associated with cellular stress as in an immune attack. Peptide levels could be an indicator of β cell distress or β cell death, and would be useful for predicting the disease state in a patient. Alternatively, the peptides herein function serve in paracrine or endocrine signaling to other islet cells or remote cells in other organs. The assay results can also find use in monitoring the effectiveness of therapeutic measures for treatment of IDDM or related diseases. In a preferred embodiment, a post-translationally modified mammalian islet cell antigen polypeptide comprises the sequence of SEQ ID NO:22 from His, amino acid residue 1 to Glu, amino acid residue 227. In another preferred embodiment the biological sample is blood.

The present invention also relates to a pharmaceutical composition comprising an islet cell antigen polypeptide of the present invention, together with a pharmaceutically acceptable carrier or vehicle, such as saline, buffered saline, water or the like. Formulations may further include one or more excipients, preservatives, solubilizers, etc. Methods of formulation are well known in the art and are disclosed, for example, in *Remington's Pharmaceutical Sciences*, Gennaro, ed., Mack Publishing Co., Easton Pa., 1990, which is incorporated herein by reference. Therapeutic doses will generally be in the range of 0.1 to 100 μg/kg of patient weight, with the exact dose determined by the clinician according to accepted standards, taking into account the nature and severity of the condition to be treated, patient traits, etc. Determination of dose is within the level of ordinary skill in the art. In general, a therapeutically effective amount of an islet cell antigen polypeptide of the present invention is an amount sufficient to produce a clinically significant reduction in β-cell loss or a delay of clinical onset of IDDM.

In a related aspect, the present invention provides diagnostic kits for use with the recombinant or synthetic islet cell antigen polypeptides of the present invention, in detecting autoantibodies to pancreatic β-islet cells. Thus, 1851 polypeptides may be provided, usually in lyophilized form, in a container, either alone or in conjunction with additional reagents, such as 1851-specific antibodies, labels, and/or anti-human antibodies and the like. The 1851 polypeptides and antibodies, which may be conjugated to a label or unconjugated, are included in the kits with buffers, such as Tris phosphate, carbonate, etc., stabilizers, biocides, inert proteins, e.g., serum albumin, and the like. Frequently it will be desirable to include an inert extender or excipient to dilute the active ingredients, where the excipient may be present in from about 1 to 99% of the total composition. Where an antibody capable of binding to the islet cell antigen polypeptide autoantibody or to the recombinant or synthetic 1851 polypeptide is employed in an assay, this will typically be present in a separate vial.

Within one aspect of the present invention, islet cell antigen polypeptides, including derivatives thereof, as well as portions or fragments of these polypeptides, are utilized to prepare antibodies for diagnostic or therapeutic uses which specifically bind to islet cell antigen polypeptides. As used herein, the term "antibodies" includes polyclonal antibodies, monoclonal antibodies, antigen-binding fragments thereof such as F(ab')$_2$ and Fab fragments, as well as recombinantly produced binding partners. These binding partners incorporate the variable regions from a gene which encodes a specifically binding monoclonal antibody. Antibodies are defined to be specifically binding if they bind to the islet cell antigen polypeptides with a $K_a$ of greater than or equal to $10^7$/M. The affinity of a monoclonal antibody or binding partner may be readily determined by one of ordinary skill in the art (see, Scatchard, Ann. NY Acad. Sci. 51: 660–72, 1949).

Methods for preparing polyclonal and monoclonal antibodies have been well described in the literature (see for example, Sambrook et al., *Molecular Cloning: A Laboratory Manual, Second Edition,* Cold Spring Harbor, N.Y., 1989; and Hurrell, J. G. R., Ed., *Monoclonal Hybridoma Antibodies: Techniques and Applications,* CRC Press, Inc., Boca Raton, Fla., 1982, which is incorporated herein by reference). As would be evident to one of ordinary skill in the art, polyclonal antibodies may be generated from a variety of warm-blooded animals such as horses, cows, goats, sheep, dogs, chickens, rabbits, mice, or rats, for example. The immunogenicity of the islet cell antigen polypeptide may be increased through the use of an adjuvant such as Freund's complete or incomplete adjuvant. A variety of assays known to those skilled in the art may be utilized to detect antibodies which specifically bind to an islet cell antigen. Exemplary assays are described in detail in *Antibodies: A Laboratory Manual,* Harlow and Lane (Eds.), Cold Spring Harbor Laboratory Press, 1988. Representative examples of such assays include: concurrent immunoelectrophoresis, radio-immunoassays, radio-immunoprecipitations, enzyme-linked immuno-sorbent assays, dot blot assays, inhibition or competition assays, and sandwich assays.

Additional techniques for the preparation of monoclonal antibodies may be utilized to construct and express recombinant monoclonal antibodies. Briefly, mRNA is isolated from a β cell population and used to create heavy and light chain immunoglobulin cDNA expression libraries in a suitable vector such as the λIMMUNOZAP(H) and λIMMUNOZAP(L) vectors, which may be obtained from Stratogene Cloning Systems (La Jolla, Calif.). These vectors are then screened individually or are co-expressed to form Fab fragments or antibodies (Huse et al., *Science* 246: 1275–81, 1989; Sastry et al., *Proc. Natl. Acad. Sci. USA* 86: 5728–32, 1989). Positive plaques are subsequently converted to a non-lytic plasmid which allows high level expression of monoclonal antibody fragments in *E. coli.*

Binding partners such as those described above may also be constructed utilizing recombinant DNA techniques to incorporate the variable regions of a gene which encodes a specifically binding antibody. The construction of these proteins may be readily accomplished by one of ordinary skill in the art (see for example, Larrick et al., *Biotechnology* 7: 934–38, 1989; Reichmann et al., *Nature* 322: 323–27, 1988 and Roberts et al. *Nature* 328: 731–34, 1987). Once suitable antibodies or binding partners have been obtained, they may be isolated or purified by many techniques well described in the literature (see for example, *Antibodies: A Laboratory Manual,* ibid.). Suitable techniques include protein or peptide affinity columns, HPLC or RP-HPLC, purification on protein A or protein G columns or any combination of these techniques. Within the context of the present invention, the term "isolated" as used to define antibodies or binding partners means "substantially free of other blood components."

Antibodies of the present invention may be produced by immunizing an animal, a wide variety of warm-blooded animals such as horses, cows, goats, sheep, dogs, chickens, rabbits, mice, and rats can be used, with a recombinant or synthetic islet cell antigen polypeptide or a selected portion thereof (e.g., a peptide). For example, by selected screening one can identify a region of the islet cell antigen polypeptide such as that predominantly responsible for recognition by anti-islet cell antigen polypeptide antibodies, or a portion which comprises an epitope of a islet cell antigen polypeptide variable region, which may thus serve as a islet cell antigen polypeptide-specific marker. Antibody producing cells obtained from the immunized animals are immortalized and screened, or screened first for, e.g., the production of antibody which inhibits the interaction of the anti-islet cell antigen polypeptide autoantibody with the islet cell antigen polypeptide and then immortalized. As the generation of human monoclonal antibodies to a human antigen, such as an 1851 polypeptide, may be difficult with conventional immortalization techniques, it may be desirable to first make non-human antibodies and then transfer via recombinant DNA techniques the antigen binding regions of the non-human antibodies, e.g. the F(ab')2 or hypervariable regions, to human constant regions (Fc) or framework regions to produce substantially human molecules. Such methods are generally known in the art and are described in, for example, U.S. Pat. No. 4,816,397, and EP publications 173,494 and 239,400, which are incorporated herein by reference.

Alternatively, one may isolate DNA sequences which encode a human monoclonal antibody or portions thereof that specifically bind to islet cell antigen polypeptides by screening a DNA library from human B cells according to the general protocol outlined by Huse et al., *Science* 246:

1275–81, 1989, incorporated herein by reference, and then cloning and amplifying the sequences which encode the antibody (or binding fragment) of the desired specificity.

In another aspect of the invention, the mammalian islet cell antigen polypeptides can be used to clone T cells which have specific receptors for the islet cell antigen polypeptide. Once the islet cell antigen polypeptide specific T cells are isolated and cloned using techniques generally available to the skilled artisan, the T cells or membrane preparations thereof can be used to immunize animals to produce antibodies to the islet cell antigen polypeptide receptors on T cells. The antibodies can be polyclonal or monoclonal. If polyclonal, the antibodies can be murine, lagomorph, equine, ovine, or from a variety of other mammals. Monoclonal antibodies will typically be murine in origin, produced according to known techniques, or human, as described above, or combinations thereof, as in chimeric or humanized antibodies. The anti-islet cell antigen polypeptide receptor antibodies thus obtained can then be administered to patients to reduce or eliminate T cell subpopulations which recognize and participate in the immunological destruction of islet cell antigen polypeptide bearing cells in an individual predisposed to or already suffering from a disease, such as IDDM. Further, the islet cell antigen polypeptide T cell receptors can thus be identified, cloned and sequenced, and receptor polypeptides synthesized which bind to the islet cell antigen polypeptides and block recognition of the islet cell antigen polypeptide-bearing cells, thereby impeding the autoimmune response against host islet cells. Howell et al. (*Science* 246: 668–70, 1989) have demonstrated that T cell receptor peptides can block the formation of the tri-molecular complex between T cells, autoantigen and major histocompatibilty complex in an autoimmune disease model.

Antibodies and binding partners of the present invention may be used in a variety of ways. The tissue distribution of the islet cell antigen, for example, may be determined by incubating tissue slices with a labeled monoclonal antibody which specifically binds to the islet cell antigen polypeptides, followed by detection of the presence of the bound antibody. Labels suitable for use within the present invention are well known in the art and include, among others, fluorescein, isothiocyanate, phycoerythrin, horseradish peroxidase, and colloidal gold. The antibodies of the present invention may also be used for the purification of the islet cell antigen polypeptides of the present invention. The coupling of antibodies to solid supports and their use in purification of proteins is well known in the literature (see for example, *Methods in Molecular Biology*, Vol. 1, Walker (Ed.), Humana Press, New Jersey, 1984, which is incorporated by reference herein in its entirety) Antibodies of the present invention may be used as a marker reagent to detect the presence of islet cell antigen polypeptides on cells or in solution. Such antibodies are also useful for western analysis or immunoblotting, particularly of purified cell secreted material. Polyclonal, affinity purified polyclonal, monoclonal and single chain antibodies are suitable for use in this regard. In addition, proteolytic and recombinant fragments and epitope binding domains can be used herein. Chimeric, humanized, veneered, CDR-replaced, reshaped or other recombinant whole or partial antibodies are also suitable.

The following examples are offered by way of illustration, not by way of limitation.

EXAMPLES

Example 1

Synthesis of Macaque Islet Cell cDNA and Preparation of a Macaque Islet Cell cDNA Library Islets of Langerhans (~100,000) were isolated by collagenase digestion and Ficoll density gradient centrifugation from pancreas of *Macaca nemestrina* (obtained from the University of Washington Primate Center, Seattle, Wash.). These cells were then flash frozen in liquid nitrogen and stored at −80° C. until use. Total RNA from the islets was isolated according to the method of Chirgwin et al., *Biochemistry* 18: 52–94, 1994, incorporated herein by reference, using polytron homogenization in guanidinium thiocynate and LiCl centrifugation. Poly(A)+RNA was isolated using oligo. d(T) cellulose chromatography (Aviv and Leder, *Proc. Natl. Acad. Sci. USA* 69: 1408–12, 1972).

First strand cDNA was synthesized from two-time poly d(T)-selected liver poly(A)+RNA. Ten microliters of a solution containing 10 μg of liver poly(A)+RNA was mixed with 2 μl of 20 pmole/μl first strand primer ZC3747 (SEQ ID NO:8) and 4 μl of diethylpyrocarbonate-treated water. The mixture was heated at 65° C. for 4 minutes and cooled by chilling on ice.

The first strand cDNA synthesis was initiated by the addition of 8 μl of 5×SUPERSCRIPT buffer (GIBCO BRL, Gaithersburg, Md.), 4 μl of 100 mM dithiothreitol, and 2.0 μl of a deoxynucleotide triphosphatate solution containing 10 mM each of DATP, dGTP, dTTP and 5-methyl-dCTP (Pharmacia LKB Biotechnology Inc., Piscataway, N.J.) to the RNA-primer mixture. The reaction mixture was incubated at 45° C. for 4 minutes. After incubation, 10.0 μl of 200 U/μl SUPERSCRIPT reverse transcriptase (GIBCO BRL) was added. The efficiency of the first strand synthesis was analyzed in a parallel reaction by the addition of 10 μCi of $^{32}$P-αdCTP to a 5 μl aliquot of the reaction mixture to label the reaction products. The first strand synthesis reaction mixtures were incubated at 45° C. for 45 minutes followed by a 15 minute incubation at 50° C. Unincorporated nucleotides were removed from each reaction by precipitating the cDNA in the presence of 8 μg of glycogen carrier, 2.5 M ammonium acetate and 2.5 volume ethanol. The unlabeled cDNA was resuspended in 50 μl water and used for the second strand synthesis. The length of first strand cDNA was assessed by resuspending the labeled cDNA in 20 μl water and determining the cDNA size by agarose gel electrophoresis.

Second strand synthesis was performed on the RNA-DNA hybrid from the first strand synthesis reaction under conditions that promoted first strand priming of second strand synthesis resulting in DNA hairpin formation. A reaction mixture was prepared containing 20.0 μl of 5×polymerase I buffer (100 mM Tris, pH 7.4, 500 mM KCl, 25 mM MgCl$_2$, 50 mM (NH$_4$)$_2$SO$_4$), 1.0 μl of 100 mM dithiothreitol, 2.0 μl of a solution containing 10 mM of each deoxynucleotide triphosphate, 3.0 μl 5 mM β-NAD, 1.0 μl of 3 U/μl *E. coli* DNA ligase (New England Biolabs, Inc., Beverly, Mass.), 5.0 μl of 10 U/μl *E. coli* DNA polymerase (Gibco BRL) and 50.0 μl of the unlabeled first strand DNA. A parallel reaction in which a 10 μl aliquot of the second strand synthesis was labeled by the addition of 10 μCi of $^{32}$P-αdCTP was used to monitor the efficiency of second strand synthesis. The reaction mixtures were incubated at room temperature for 5 minutes followed by the addition of 1.5 μl of 2 U/μl RNase H (Gibco BRL) to each reaction mixture. The reactions were incubated at 15° C. for 2 hours and 15 minutes, followed by a 15 minute incubation at room temperature. The reactions were each terminated by serial phenol/chloroform and chloroform/isoamylalcohol extractions. The DNA from each reaction was precipitated in the presence of ethanol and 2.5 M ammonium acetate. The DNA from the unlabeled reaction was resuspended in 100 μl water. The labeled DNA was resuspended and electrophoresed as described above.

The single-stranded DNA in the hairpin structure was cleaved using mung bean nuclease. The reaction mixture contained 20 µl of 10×Mung Bean Nuclease Buffer (Stratagene Cloning Systems, La Jolla, Calif.), 16 µl of 100 mM dithiothreitol, 54 µl water, 100 µl of the second strand cDNA, and 10 µl of a 1:10 dilution of Mung Bean Nuclease, final concentration 10.5 U/µl (Promega Corp., Madison, Wis.) in Stratagene MB dilution Buffer (Stratagene Cloning Systems). The reaction was incubated at 37° C. for 15 minutes, and the reaction was terminated by the addition of 20 µl of Tris-HCl, pH 8.0 followed by sequential extractions with phenol/chloroform and chloroform/isoamylalcohol. Following the extractions, the DNA was precipitated in ethanol and resuspended in water.

The resuspended cDNA was blunt-ended with T4 DNA polymerase. The cDNA, which was resuspended in a volume of 50 µl of water, was mixed with 50 µl of 5×T4 DNA polymerase buffer (250 mM Tris-HCl, pH 8.0, 250 mM KCl, 25 mM $MgCl_2$), 3 µl of 100 mM dithiothreitol, 3 µl of a solution containing 10 mM of each deoxynucleotide triphosphate, and 4 µl of 1.0 U/µl T4 DNA polymerase (Boehringer Mannheim, Indianapolis, Ind.). After an incubation at 10° C. for 60 minutes, the reaction was terminated by serial phenol/chloroform and chloroform/isoamylalcohol extractions. The cDNA fragments less than 400 bp in length were removed by chromatography on a Clontech TE400 spin column (Clontech, Palo Alto, Calif.). The DNA was ethanol precipitated and resuspended in 9 µl of water. Based on the incorporation of $^{32}$P-dCTP, the yield of cDNA was estimated to be 4 µg from a starting mRNA template of 10 µg.

Eco RI adapters (Pharmacia LKB Biotechnology Inc., Piscataway, N.J.) were added to the cDNA prepared above to facilitate the cloning of the cDNA into a mammalian expression vector. A 9 µl aliquot of the cDNA and 975 pmole of the adapter (15 µl) were mixed with 3 µl 10×ligase buffer (Promega Corp.), 1 µl 10 mM ATP, and 20 Units (2 µl), of T4 DNA ligase (Promega Corp.). The reaction was incubated for 16 hours at a temperature gradient of 4° C. to 15° C. The reaction was terminated by the addition of 185 µl water, 25 µl REACT 2 buffer (Gibco BRL) followed by an incubation at 65° C. for between 30 and 60 minutes. After incubation, the reaction was terminated by serial phenol/chloroform and chloroform/isoamylalcohol extractions and ethanol precipitation as described above. Following centrifugation, the DNA pellet was washed with 70% ethanol and was air dried. The pellet was resuspended in 89 µl of water.

To facilitate the directional insertion of the cDNA into a mammalian expression vector, the cDNA was digested with Xho I, resulting in a cDNA having a 5' Eco RI adhesive end and a 3' Xho I adhesive end. The Xho I restriction site at the 3' end of the cDNA was introduced through the ZC3747 primer (SEQ ID NO:8). The restriction digestion was terminated by serial phenol/chloroform and chloroform/isoamylalcohol extractions. The cDNA was ethanol precipitated, and the resulting pellet was washed with 70% ethanol and air-dried. The pellet was resuspended in 1×loading buffer (10 mM phosphate buffer, pH 8.8, 5% glycerol, 0.125% bromphenol blue).

The resuspended cDNA was heated to 65° C. for 10 minutes, cooled on ice and electrophoresed on a 0.8% low melt agarose gel (Seaplaque GTG Low Melt Agarose, FMC Corp., Rockland, Me.) using a 1 Kb ladder (Gibco BRL) as size markers. The contaminating adapters and by-product fragments below 600 bp in size were excised from the gel. The electrodes were reversed, and the cDNA was electrophoresed until concentrated near the lane origin. The area of the gel containing the concentrated DNA was excised, placed in a microfuge tube, and the approximate volume of the gel slice was determined. An aliquot of TE (10 mM Tris HCl pH 7.4, 1 mM disodium ethylenediaminetetraacetate.2 $H_2O$ (EDTA)) equivalent to half the volume of the gel slice was added to the tube, and the agarose was melted by heating to 65° C. for fifteen minutes. Following equilibration of the sample to 42° C., approximately 5 units of β-Agarase I (New England Biolabs, Inc.) was added. The sample was incubated for 2 hours to digest the agarose. After incubation, a 0.1×volume of 3M sodium acetate was added to the sample, and the mixture was incubated on ice for fifteen minutes. After incubation, the sample was centrifuged at 14,000×g for 10 minutes to remove the undigested agarose. The cDNA in the supernatant was ethanol precipitated. The cDNA pellet was washed with 70% ethanol, air dried and resuspended in 37 µl of water. The cDNA recovered from the agarose gel was phosphorylated using T4 polynucleotide kinase. The reaction consisted of 37 µl cDNA, 5 µl 10×Stratagene Ligase Buffer (Stratagene Cloning Systems). Following a 5 minute incubation at 65° C., the reaction was cooled to room temperature where 5 µl 10 mM ATP (Pharmacia) and 3 µl T4 DNA polymerase (10 U/µl, Stratagene) were added. The reaction was incubated at 37° C. for 45 minutes and at 65° C. for 10 minutes. The reaction was terminated by serial phenol/chloroform extractions. The samples were chromatographed through a Clontech TE400 spin column and were precipitated in the presence of 2.5 M ammonium acetate. The cDNA was resuspended in 15 µl of 2.5 mM Tris-HCl, pH 8.0, 0.25 mM EDTA.

The resulting Eco RI-Xho I cDNA library was cloned into the *E. coli* vector pZCEP (Jelinek et al., *Science* 259: 1614–16, 1993). Eco RI-Xho I linearized pZCEP was ligated with the Eco RI-Xho I cDNA library. The resulting plasmids were electroporated into the *E. coli* strain DH10B ELECTROMAX–(Gibco BRL). The library was plated to obtain >5×10⁵ independent colonies and aliquoted into 120 pools to give approximately 5,000 colonies per pool. An aliquot of the cells from each pool was removed for use in preparing plasmid DNA. The remaining cell mixtures were brought to a final concentration of 15% glycerol, aliquoted and frozen at −80° C. Plasmid DNA was prepared from each pool and the resulting plasmid DNA was digested with RNAse (Boehringer Mannheim) according to the manufacturer's instructions. The RNAse reaction was terminated by a phenol/chloroform/isoamylalcohol (24:24:1) extraction, and the DNA was ethanol precipitated. The pools were systematically screened as described in the examples below.

Example 2

Transfection of Macaque DNA into COS-7 Cells

Macaque DNA from each pool was transfected into COS-7 cells (African Green Monkey Kidney cells, ATCC CRL 1651) using the method essentially described by McMahan et al. (*EMBO J.* 10: 2821–32, 1991; which is incorporated by reference herein in its entirety). Briefly, one day prior to transfection approximately 2×10⁵ COS-7 cells in 2 ml growth medium containing 10% fetal bovine serum (Dulbecco's modified Eagle's medium (DMEM), 1% L-glutamine, 1% PNS antibiotic mix (Gibco BRL), 25 mM Hepes, and 1 mM NaPyruvate) were plated on sterile, single-chamber slides (Nunc AS, Roskilde, Denmark) that had been coated with 10 µg/ml of human fibronectin in PBS for 30 minutes at 37° C. and washed with phosphate buffered saline (PBS). For each pool to be tested, 1–2 µg of macaque islet cell library pooled DNA was added into 100 µl of serum free medium (SFM, F/DV medium, 10 mg/l transferrin, 2

μg/l selenium, 10 mg/l fetuin, 5 mg/l insulin, 1% L-glutamine, 25 mM Hepes, 1 mM NaPyruvate, and 0.1 mM NEAA). To each DNA sample was added 100 μl SFM containing 12 μl LipofectAMINE (Gibco BRL). The transfection solution was mixed by pipetting up and down and kept at room temperature for 15 to 45 minutes. To each mix was added 0.8 ml SFM which was then gently added to the COS-7 cells which had been washed once with SFM. The cells were incubated at 37° C., 5% $CO_2$ for 4–5 hours. One milliliter of growth medium containing 20% FBS was added to each slide. Slides were incubated overnight at 37° C., 5% $CO_2$. The spent medium was removed and replaced with 2 ml growth medium containing 10% FBS and the cells incubated for 24 to 48 hours, preferably 48 hours, at 37° C., 5% $CO_2$.

Example 3

Diabetic Sera

Sera from two prediabetic subjects, EmWi and JoGr, were selected for screening the islet cell cDNA library. Sera from both subjects were characterized for autoantibodies to known β-cell antigens using techniques known in the art. The sera were tested for GAD65 autoantibodies using an in vitro transcription/translation assay (Grubin et al., *Diabetologia* 37: 344–50, 1994) followed by immunoprecipitation using radiolabeled recombinant human GAD65 according to Hagopian et al., *J. Clin. Invest.* 91: 368–74, 1993.

Recombinant radiolabeled GAD was expressed in the presence of $^{35}S$ Methionine (Amersham Corp., Arlington Heights, Ill.) using the Sp6 bacteriophage promoter and the TNT reticulocyte lysate kit (Promega), according to manufacturer's direction. $^{35}S$ Methionine incorporation was determined by precipitation using trichloroacetic acid (TCA), and 25% or more incorporation was considered acceptable. Radiolabeled antigen was stored at −80° C. until use.

Radiolabeled antigen was diluted 1:10 in immunoprecipitation buffer (150 mM NaCl, 1% v/v Triton X-114 (Sigma Chemical Co., St. Louis, Mo.), 0.05% Bovine serum albumin (Sigma), 10 mM benzamidine (Sigma), and 10 mM HEPES pH 7.4). The antigen was incubated for preclearing for 4 hours at 4° C. with 50 μl normal human serum. Immunoglobulin was removed using 200 μl Protein A Sepharose beads (Pharmacia LKB Biotechnology Inc.) for 45 minutes. The cleared supernatant was diluted to 50,000 TCA-precipitable counts per minute (cpm) per 400 μl immunoprecipitation buffer. Four microliters of serum from diabetic or control patients was separately incubated in duplicate with 400 μl diluted antigen at 4° C. overnight with mixing by gentle rotation. Antigen-antibody complexes were precipitated by 16 μl Protein A Sepharose, and the pellet was washed 5 times in ice-cold wash buffer which consisted of 10 mM HEPES pH 7.4, 150 mM NaCl, 0.05% BSA, and 0.25% Triton X-114. Antigen was dissociated from the pellet by boiling in the presence of 2% SDS and 5% β-mercaptoethanol, and counted by scintillation counting in scintillation fluid. Counts per minute reflect the level of autoantibodies present in the sera to capture the antigen.

Autoantibodies to the protein tyrosine phosphatase IA-2/ICA512 were detected as above using a radiolabeled cytoplasmic domain of human IA-2/ICA512 (Lan et al., *DNA Cell Biology* 13: 505–14, 1994; and Hagopian et al., *Autoimmunity* 21: 61, 1995). The complete cytoplasmic domain of human IA-2 was isolated by RT-PCR from U87MG glioblastoma cells (ATCC M85). Briefly, total RNA was prepared from $5 \times 10^7$ glioblastoma cells which were homogenized in 3.5 ml guanidine/LiCl followed by CsCl centrifugation. First strand cDNA was synthesized using a Superscript~Preamplification System (GIBCO BRL) according to the manufacturer's directions. One and one half microliters of a solution containing 5 μg total U87MG RNA was mixed with 1 μl oligo dT solution and 11.5 μl diethylpyrocarbonate-treated water. The mixture was heated at 70° C. for 10 minutes and cooled by chilling on ice.

First strand cDNA synthesis was initiated by the addition of 2 μl Superscript~II buffer, 2 μl 0.1 M dithiothreitol, 1 μl deoxynucleotide triphosphate solution containing 10 mM each of DATP, dGTP, dTTP, and dCTP, and 1 μl of 200 U/μl Superscript~II reverse transcriptase to the RNA-primer mixture. The reaction was incubated at room temperature for 10 minutes followed by an incubation at 42° C. for 50 minutes, then 70° C. for 15 minutes, then cooled on ice. The reaction was terminated by addition of 1 μl RNase H which was incubated at 37° C. for 20 minutes, then cooled on ice.

A 100 μl PCR reaction mixture was then prepared containing 20 μl of first strand template, 8 μl 10×synthesis buffer, 3.3 μM ZC8802 (SEQ ID NO:9, contains 5' Xho I site and ATG), 5.4 μM ZC8803 (SEQ ID NO:10, contains Eco RI site following stop codon), 65 μl $dH_2O$ and 1 wax bead (AmpliWax~, Perkin-Elmer Cetus, Norwalk, Conn.). Following an initial cycle of 95° C. for 2 minutes, 4° C. for 10 minutes, 5 U Taq polymerase was added, and the reaction was amplified for 30 cycles of 1 minute at 95° C., 2 minutes at 55° C. and 3 minutes at 72° C. The reaction mixture was then stored at 4° C. The resulting 1.2 kb fragment (SEQ. ID. No.30) was digested with Eco RI-Xho I, treated with RNAse, then isolated by low melt agarose gel electrophoresis and ligated into Eco RI-Xho I linearized pZCEP. Sera were screened for IA-2/ICA512 autoantibodies as described above for GAD autoantibodies.

Both EmWi and JoGr sera showed reactivity to IA-2/ICA512. The sera were titered for IA-2/ICA512 reactivity on vector only transfected COS-7 cells using techniques known in the art, see for example, Greenbaum et al. (*Diabetes* 41: 1570–1574, 1992). The sera were separately adsorbed with porcine insulin (Hoechst, 10 mg/ml) and GAD (1 mg/ml) until reactivity was abolished in the respective antibody assays. These sera were then retitered for IA-2/ICA512 as above. JoGr had IA-2/ICA512 reactivity of 280 JDFU (Juvenile Diabetes Foundation Units) which persisted at >130 JDFU after adsorption. EmWi had IA-2/ICA512 reactivity of 140 JDFU which persisted at >130 JDFU after adsorption. EmWi had the lowest background staining and was therefore used for primary screening.

Twenty milliliters of EmWi was diluted 1:1 in 0.1 M $NaPO_4$ buffer, pH 8.0 and incubated with an equal volume of Protein A covalently linked to Sepharose beads (Zymed, South San Francisco, Calif.) for affinity purification. After gentle mixing for 45 minutes at 4° C., the slurry was loaded onto a column and washed with 10 column volumes of 0.1 M $NaPO_4$ buffer, pH 8.0 and one column volume of 0.01 M $NaPO_4$ buffer, pH 8.0, before elution of immunoglobulins with 0.05 M Na citrate buffer, pH 3.5. Eluted immunoglobulins were immediately neutralized to pH 7.0 with 2 M Tris, pH 8.0. Eluted fractions were evaluated by spectrophotometric absorption at 280 nM, and peak fractions were pooled, aliquoted and flash frozen for storage at −80° C. Typically the concentration was 4 mg/ml IgG. COS-7 cells were grown to confluence in 150 ml T-flasks, washed with PBS, fixed in 4% paraformaldehyde, and permeabilized by freeze/thaw. The pooled sera were diluted to 1 mg/ml in PBS and incubated with the permeabilized COS-7 cell lysate overnight at 4° C. Supernatant was cleared at 100,000×g and aliquotted for storage at −80° C. for use in the binding assay.

Example 4

Binding Assay

The macaque DNA transformed COS-7 cells on single chamber slides, from Example 2, were prepared for assay by removing spent medium from the slides and washing the cells 3 times in PBS at room temperature. The cells were fixed with 1 ml 50% ETOH/50% acetone for 5 minutes at room temperature followed by two washes in PBS and two washes in 1% bovine serum albumin (BSA) in PBS. The precleared serum (EmWi) was diluted to 0.2 mg/ml in a 5% BSA in PBS solution, and 500 µl was added to each of the slides which were then covered, wrapped in plastic wrap, and rocked gently on a rocker overnight at room temperature.

The slides were then washed three times in a 1% BSA/PBS solution, three minutes for each wash. Following the final wash, the slides were blocked for 10 minutes with 1 ml 5% BSA/4% normal goat serum (Sigma) in PBS at room temperature. The blocking buffer was removed, and 500 µl of 0.02 mg/ml biotinylated Protein A (Amersham Corp., Arlington Heights, Ill.) in 5% BSA/4% normal goat serum/PBS was added, followed by a 30 minute incubation at room temperature. The slides were washed three times with 1% BSA/PBS, three minutes for each wash, then 500 µl streptavidin-gold (Amersham) diluted 1:50 in 5% BSA/4% normal goat serum/PBS was added to each slide. Following a 60 minute incubation at room temperature the slides were washed three times in 1% BSA/PBS and one final time in PBS. The slides were then fixed by adding 0.5 ml of 9% formaldehyde/45% acetone in PBS for 30 seconds followed by three, 3 minute washes in $dH_2O$.

An equal volume of silver enhancement solution and initiator (IntenSE~M Silver Enhancement Kit, Amersham) were mixed in a 15 ml conical tube, and 0.5 ml was added to each slide. The slides were allowed to develop for 20 minutes or until the desired color intensity was achieved. The slides were then rinsed twice for five minutes in $dH_2O$ and air dried. A single positive pool (#18) containing approximately 5,000 clones was found out of approximately 50 pools screened using EmWi sera.

To isolate the positive clone(s) from pool #18, one 150 mm plate was plated to give approximately 10,000 colonies from the #18 pool. Filter lifts were prepared using the methods essentially described by Hanahan and Meselson (*Gene* 10: 63, 1980) and Maniatis et al. (*Molecular Cloning: A Laboratory Manual*, Cold Spring Harbor, N.Y., 1982), which are incorporated herein by reference in their entirety. The hybridization probe was obtained by PCR amplification of plasmid DNA from pool #18. Briefly, an aliquot of the plasmid DNA from pool #18 was subjected to PCR amplification using oligonucleotides ZC8802 and ZC8803 (SEQ ID NOS:9 and 10, respectively). A 50 µl reaction mixture was prepared containing 0.05 µg of the plasmid DNA from pool #18; 20 pmole of ZC 8802 and ZC 8803 (SEQ ID NOS:9 and 10, respectively); 10 nmoles of each deoxynucleotide triphosphate (Pharmacia); 4 µl 10×synthesis buffer (Boehringer Mannheim), and 2.5 U Taq polymerase (Boehringer Mannheim). The PCR reaction was run for 24 cycles (1 minute at 94° C., 1 minute at 56° C., and 1 minute at 72° C.). An approximately 1.1 Kb band was isolated on a low melt agarose gel electrophoresis and random primed using the MEGAPRIME~Kit (Amersham) according to the manufacturer's instructions.

The filter was hybridized in a solution containing 6×SSC, 0.1% SDS, 5×Denhardt's, 200 µg/ml denatured, sheared salmon sperm DNA, and $1×10^5$ cpm/ml of $^{32}P$-labeled PCR fragment. The filter was hybridized overnight at 65° C. The excess label was removed by two, 15 minute washes with 2×SSC, 0.1% SDS at 65° C. The filter was exposed to film overnight at −80° C. with two screens.

Eighteen positive colonies were detected. Six of these colonies were cultured and subjected to a second round of filter lifts as described above, and from this two positive clones were identified. Restriction endonuclease analysis showed that both contained an approximate 2 Kb insert. One clone, designated M1.18.5.1, was sequenced, revealing a 2,170 bp coding region which contained regions of homology to the protein tyrosine phosphatase family, especially IA-2/ICA512. Comparison of the full length human protein tyrosine phosphatase IA-2/ICA512 with M1.18.5.1 suggests that the coding region of M1.18.5.1 is missing amino terminal sequence corresponding to approximately 400 amino acids. The partial nucleic acid sequence and deduced amino acid sequence of M1.18.5.1 is shown in SEQ ID NO 1 and SEQ ID NO:2.

M1.18.5.1 was re-transfected into COS-7 cells and assayed as described above. In addition to the EmWi sera, the JoGr sera, which had a high titer to IA-2, was added to the screen and both detected M1.18.5.1.

Example 5

Isolation of Human Islet Cell Antigen 1851

The 2,170 nucleotide sequence from M1.18.5.1 (SEQ ID NO 1) was used to conduct a sequence search for a human homolog. A match was found in the GenBank database (GenBank ID: T0361, clone ID: HFBCV88) submitted by The Institute of Genomic Research, Gaithersburg, Md., as an expressed sequence tag (EST) from a human fetal brain library (Stratagene Cloning Systems). HFBCV88 (EST24415. seq), a i27 amino acid polypeptide, SEQ ID NO:5, had homology to a region of the cytoplasmic domain of M1.18.5.1. The closest human DNA sequence to HFBCV88 is HSICA512, islet cell antigen ICA-512.

An oligonucleotide primer (ZC10,011 SEQ ID NO:11) was made to a conserved region between 1851 and HFBCV88 which differed from the corresponding sequence of mouse and human IA-2/ICA512 in that an arginine was substituted for a methionine. Combined with a 128 fold degenerate primer (ZC10,019 SEQ ID NO:14, AARGCNACNGTNGAYAAY, wherein R is A or G, N is A, C, T, or G, and Y is C or T) which lies just upstream of the transmembrane domain, in the extracellular domain, a portion of the human homologue of M1.18.5.1 was identified in human insulinoma cDNA by PCR. Briefly, a PCR reaction was performed in a 100 µl final volume using 12.5 ng Marathon-ready human insulinoma cDNA prepared according to manufacturerrs instruction (Marathon~cDNA Amplification Kit, Clontech), 20 pmoles each of primers ZC 10,011 (SEQ ID NO:11) and ZC 10,019 (SEQ ID NO:14), and the reagents provided in the Marathon~PCR kit (Clontech) according to the manufacturer's instructions. The reaction was amplified for 30 cycles (1 minute at 94° C., 30 seconds at 60° C., 5 minutes at 68° C.) followed by a 10 minute extension at 72° C. An 800 bp (WK11111, SEQ ID NO:32) and a 1,200 bp (WK121315, SEQ ID NO:34) fragment were isolated by low melt agarose gel electrophoresis.

A 3'RACE Marathon PCR was also performed in a 50 µl final volume using 12.5 ng Marathon-ready human insulinoma cDNA, 10 pmoles each of primers ZC 10,177 (SEQ ID NO:12) the complement to ZC 10,011, and AP-1 (adaptor primer, supplied with kit), and the reagents provided in the 3'RACE Marathon-PCR kit (Clontech), according to the manufacturer's instructions. The reaction was amplified for 30 cycles (30 seconds at 94° C., 30 seconds at 68° C.). A 900 bp and a 2,000 bp (WK121111, SEQ ID NO:33) fragment were isolated by low melt agarose electrophoresis.

The 800 bp, (SEQ ID NO:32) 1,200 bp, (SEQ ID NO:34) and 2,000 bp (SEQ ID NO:33) PCR fragments were independently subcloned into pCR1 (Invitrogen Inc., San Diego, Calif.), using the TA Cloning Kit (Invitrogen Inc.) according to the manufacturer's instructions. The resulting plasmids (11.1.1, 11.1.2, and 11.1.3, respectfully) were used to transform E. coli XL-1 cells. Transformants were screened for presence of insert, followed by sequencing of the insert.

Example 6

Detection of Human Islet Cell Antigen Autoantibodies

An approximately 1.1 kb (SEQ ID NO:6) Eco RI-Hind III cytoplasmic fragment of human islet cell antigen 1851 cDNA was inserted into the vector pcDNAII (Invitrogen, San Diego, Calif.), and designated IL1851-3. The resultant polypeptide was transcribed and translated in vitro using a TNT Coupled Reticulocyte Lysate System (Promega), according the manufacturer's instructions.

The labeled, synthesized cytoplasmic portion of human islet cell antigen 1851 was used to screen diabetic sera from six patients, for the presence of autoantibodies. Protein A-Sepharose immunoprecipitation, as described above, showed that sera from all six reacted positively with the in vitro synthesized, human islet cell antigen, and indicated that the major autoepitope is likely present on this polypeptide.

Additional immunoprecipitation assays were performed with a spectrum of serum samples, including 91 healthy control sera (median age 22 years, range 1–49 years, 49% males and 51% females); 183 newly diagnosed IDDM patients sampled at onset (median age 11 years, 51% males and 49% females); and 60 first degree relatives of type I diabetic patients sampled a mean of 2.0 years before onset (median age 12 years, 58% males and 42% females). Parallel autoantibody assays used the intracellular domain of IA-2/ICA512. Immunoprecipitation assays were as described above. Briefly, 4 μl of serum from diabetic or control patients were separately incubated in duplicate with 400 μl $^{35}$S radiolabeled antigen (cytoplasmic portion of human islet cell antigen 1851, SEQ ID NO: 6, in immunoprecipitation buffer (10 mM Hepes, 0.05% BSA, 150 mM NaCl, 10 mM benzamidine, and 1% Triton X114)) at 4° C. overnight with mixing by gentle rotation (Hagopian et al., J. Clinc. Invest. 91:368–74, 1995). Antigen-antibody complexes were precipitated using 20 μl Protein A Sepharose, and the pellet was washed 3 times in ice-cold wash buffer (which consisted of 10 mM HEPES pH 7.4, 150 mM NaCl, 0.25% BSA, and 0.25% Triton X-114) and one cold water wash. Antigen was dissociated from the pellet by boiling in the presence of 2% SDS and 5% β-mercaptoethanol, counted by scintillation counting in scintillation fluid, and the results expressed as islet cell antigen 1851 index (Hagopian et al., Diabetes 42:631–36, 1993). Counts per minute reflect the level of autoantibodies present in the sera that can capture the antigen. Assay cutoff was an index of 0.04, determined as the mean +3 standard deviations of 91 control sera. Assay sensitivity, specificity, and positive predictive value were calculated (Hagopian et al., ibid., 1995).

Immunoprecipitation assays revealed autoantibodies in 56/183 (30.6%) newly diagnosed IDDM patients, 28/60 (46.7%) first degree relatives later progressing to clinical diabetes, but only 1/91 (1.1%) healthy control subject groups. For first degree relatives, this represents a positive predictive value of 58% and a sensitivity of 48%.

Of sera from 153 newly diagnosed patients, 83 (54%) recognized IC-2/ICA512 and 48 (31%) recognized islet cell antigen 1851. Only 1/48 (2%) from the sera recognizing islet cell antigen 1851 did not precipitate IA-2/ICA512, but 35/83 (42%) from the sera reactive with IA-2/ICA512 did not bind islet cell antigen 1851. Of those positive for both antigens, reactivity to IA-2/ICA512 was generally stronger than that to islet cell antigen 1851.

The intracellular domains of human islet cell antigen 1851 and IA-2/ICA512 were expressed and radiolabeled by in vitro transcription and translation using a TNT Coupled Reticulocyte Lysate System (Promega), according the manufacturer's instructions, as described above. SDS-polyacrylamide gel electrophoresis (SDS-PAGE) and autoradiography of the resulting radiolabeled polypeptide revealed, for human islet cell antigen 1851, a major band of 46 kD and a minor band at 33 kD, both immunoprecipitated by IDDM sera. Limited trypsin digest of the radiolabeled immunoprecipitated intracellular fragment of macaque and human islet cell antigen 1851 and IA-2/ICA512 was done using the method of Christie et al. (J. Exp. Med. 172:789–94, 1990), followed by SDS-PAGE and autoradiography, which revealed a 37 kD product from both macaque and human islet cell antigen 1851. This product was distinct from the 40 kD product produced by limited trypinization of the intracellular domain of IA-2/ICA512.

In order to test whether IA-2/ICA512 autoantibodies recognized only epitopes shared with islet cell antigen 1851, the intracellular domain of IA-2/ICA512 was expressed in baby hamster kidney cells (BHK cells). The 1.2 kb IA-2/ICA512 intracellular fragment (SEQ ID NO:30) from Example 3 was ligated into pZEM219b under the SV40 promoter (Busby et al., J. Biol. Chem. 266:15286–92, 1991) and cellular expression was determined by immunocytochemistry using rabbit polyclonal antiserum to IA-2/ICA512 (Rabin et al., J. Immunol. 152:3183–88, 1994). IA-2/ICA512-transfected BHK cells were homogenized in homogenization buffer (0.25% Triton X-114, 10 mM benzamidine). Using Western blotting, the concentration of recombinant intracellular IA-2/ICA512 was estimated at 7 μg/ml of cell extract.

Immunoprecipitation assays, as described above, were done using radiolabeled islet cell antigen 1851 in the presence of 0.5 μg of unlabeled IA-2/ICA512 per microliter of islet cell antigen 1851 positive sera, as a competitor. Islet cell antigen 1851 autoantibodies not fully blocked by this amount of IA-2/ICA512 were subjected to repeated immunoprecipitation assays using a 2.5 fold increase of unlabeled IA-2/ICA512 as a competitor. As a control, extracts from non-transfected BHK cells were used. Recombinant intracellular IA-2/ICA512 fully blocked islet cell antigen 1851 reactivity in 29/53 islet cell antigen 1851 positive sera, while a median of 21.4% (range 3%–55%) of original immunoreactivity was retained in 24/53 sera. Increasing the IA-2/ICA512 concentration did not reduce this residual immunoreactivity, suggesting that unique islet cell antigen 1851 epitopes are being recognized in certain sera.

Example 7

Cloning the Remaining 5' Sequence of Macaque and Human Islet Cell Antigen 1851 cDNA To obtain the remaining 5' macaque cDNA sequence one pool (#12) from the macaque library described in Example 1 was plated at 10,000 colonies/150 mm plate. Filter lifts were prepared (Maniatis et al. (*Molecular Cloning: A Laboratory Manual*, Cold Spring Harbor, N.Y., 1982) and denatured with 0.5 M NaOH for four minutes, neutralized with 1 M Tris pH 8.0 for 2 minutes followed by renaturation with 1 M Tris pH 8.0/1.5 M NaCl for 2 minutes. Filters were cross linked in a UV Stratalinker (1200 µJ) (Stratagene Cloning Systems, La Jolla, Calif.). The filters were prehybridized in 20 ml hybridization buffer (6×SSC, 0.5% SDS, 5×Denhardts and 0.2 mg/ml boiled salmon sperm DNA) overnight at 65° C. The filters were then hybridized in 20 ml hybridization buffer containing $1 \times 10^6$ cpm/ml $\gamma^{32}$P-ATP labeled hybridization probe (ZC10504 SEQ ID NO:18) overnight at 65° C. The labeled hybridization probe was prepared by adding to a 5 µl final volume 30 pmol oligo ZC10504 (SEQ ID NO:18), T4 polynucleotide kinase buffer, 37.5 pmol $\gamma^{32}$P-ATP and 10 U T4 polynucleotide kinase The reaction was incubated for 1 hour at room temperature and unincorporated ATP was removed using a Stratagene push column according the manufacturer's instructions (Stratagene Cloning Systems, La Jolla, Calif.). Following the hybridization, excess unbound label was removed from the filters with eight washes in 2×SSC/0.1% SDS (2 times with 20 ml, 5 times with 30 ml and a final wash in 100 ml) for 5 to 10 minutes at 65° C. The filters were exposed to film overnight at −80° C.

Several positive colonies were detected. One of these colonies was cultured from a replica plated colony and subjected to sequence analysis. The clone, 12.10504.1, contained 2,736 bp coding region (SEQ ID NO:23), containing the cytoplasmic and transmembrane domains and extending the 5' end of the macaque extracellular domain sequence (SEQ ID NO:1) by 609 bp.

5' RACE PCR was used to generate the remaining 5' cDNA fragments of macaque islet cell antigen 1851. To a 50 µl final volume was added 5 pmol of a vector-specific oligonucleotide primer (ZC11197, SEQ ID NO:29), 5 pmol of a macaque specific primer (ZC11654, SEQ ID NO:28), 1 ng macaque islet cell cDNA library from Example 1, 40 mM dNTPs, TAQ Polymerase buffer and 1.25 U TAQ Polymerase. A one minute denaturation at 94° C. was followed by 30 amplification cycles (30 seconds at 94° C., 1 minute at 60° C., 2 minutes at 72° C.) followed by a 6 minute extension at 72° C.).

Four independent 5'RACE PCR reactions were run, each using a different pool from the macaque library as template. Four fragments were obtained, a 738 bp fragment (SEQ. ID. No. 24) extending the 5' end by 246 bp; a 932 bp fragment (SEQ ID NO:25) extending the 5' end by 193 bp; a 999 bp fragment (SEQ ID NO:26) extending the 5' end by 68 bp and a 1011 bp fragment (SEQ ID NO:27) which contained the remaining 5' sequence with the exception of the start methionine. The fragments were isolated by agarose electrophoresis, excised and separated from the agarose using the Qiagen Qiaquick Gel Extraction System (Qiagen, Inc., Chatsworth, Calif.) according to manufacturer's instruction. The fragments were subcloned into pGEM-T (Promega Corp., Madison, Wis.), using the TA Cloning Kit (Promega Corp.) according to the manufacturer's instructions. The resulting plasmids pJML8, 7, 9 and 10 respectfully, were used to transform *E. coli* DH10B cells. Transformants were screened for presence of insert, followed by sequencing of the insert.

The 5' RACE fragments (SEQ ID Nos:23, 24, 25, 26 and 27) contain overlapping segments and were aligned with the macaque islet cell antigen 1851 sequence of SEQ ID NO:1 to give a full length macaque islet cell antigen 1851 DNA sequence as represented in SEQ ID NO:15. Comparison of the human protein tyrosine phosphatase IA-2/ICA512 cDNA and amino acid sequences with those of the macaque islet cell antigen 1851 cDNA and amino acid sequences (SEQ ID NOs: 15 and 16) suggests that the coding region is missing the start methionine.

A vector containing the full length macaque sequence can be created using PCR. The macaque 5' RACE fragments (SEQ ID NOs: 23, 24, 25, 26 and 27) can be joined using PCR. A clone shown to possess the complete coding sequence can then be digested with convenient restriction sites and subcloned into a vector of choice. Clones can be screened for correct insertion of the full length sequence and subjected to DNA sequence analysis.

PCR using macaque derived primers was done to identify remaining 5' cDNA sequence for the human islet cell antigen 1851 (SEQ ID NO:6). To a 50 µl final volume was added 5 pmol each of two gene-specific oligonucleotide primers ZC10504, SEQ ID NO:18 and ZC11653, SEQ ID NO:17, 1 ng Marathon-ready insulinoma cDNA, prepared according to manufacturer's instruction (Marathon~cDNA Amplification Kit, Clontech), 40 mM dNTPs, TAQ Polymerase buffer and 1.25 U TAQ Polymerase. The reaction was denatured at 94° C. for one minute, amplified for 30 cycles (30 seconds at 94° C., 1 minute at 63° C., 2 minutes at 72° C.), followed by a 6 minute extension at 72° C.).

A 1263 bp fragment (SEQ ID NO:31) was isolated by agarose electrophoresis. The isolated fragment was then excised and subcloned into pGEM-T using the TA Cloning Kit (Promega, Corp.), as described above. The clones were then analyzed for the presence of insert, and those containing insert were subjected to DNA sequence analysis. The human islet cell antigen 1851 fragments can be joined using PCR to give the human sequence as represented in SEQ ID NO:21. Clones can be screened for correct insertion of the fragments and subjected to DNA sequence analysis. Comparison of the human protein tyrosine phosphatase IA-2/ICA512 cDNA with that of the human islet cell antigen 1851 sequences (SEQ ID NO:21 and 22) suggests that the coding region is missing 5' sequence corresponding to approximately 600 bp. Including the 3' untranslated region, but not the 5' untranslated region, the estimated mRNA size for the human sequence is 5 kb, which is consistent with the 5.5 kb mRNA observed in Northern blots discussed below. To obtain the remaining 5' human islet cell antigen 1851 cDNA sequence, additional PCR or 5' RACE PCR reactions can be performed as described above.

Example 8

Tissue Distribution

Human Multiple Tissue Northern Blots (MTN I, MTN II, and MTN III; Clontech, Palo Alto, Calif.) were probed to determine the tissue distribution of human islet cell antigen 1851 expression. A 38 nucleotide oligonucleotide sequence just external to the transmembrane region of human islet cell antigen 1851, which is distinct from the corresponding sequence of IA-2/ICA512 (SEQ ID NO:18) was radioactively labeled with $\gamma^{32}$P using a T4 nucleotide kinase (GIBCO BRL, Gaithersburg, Md.) according to the manufacturer's specifications. ExpressHyb~(Clontech) solution was used for prehybridization and as a hybridizing solution for the Northern blots. Hybridization took place overnight at 37° C. using $5 \times 10^6$ cpm/ml of labeled probe. The blots were then washed three times at room temperature, once at 50° C. for 30 minutes, once at 60° C., in 6×SSC, 0.1% SDS. A final wash at 68° C. with 2×SSC, 0.05% SDS for 20 minutes was done prior to autoradiography. Two transcript sizes were detected. A strong 5.5 kb band and a weaker 3.3 kb band were detected in brain, pancreas and prostate, with lesser signals in spinal cord, thyroid, adrenal and GI tract. With the exception of prostate, this represents the expected neuroendocrine distribution.

In order to define tissue localization further, in situ hybridization was performed on macaque pancreas, adrenal gland and muscle. The 38 nucleotide islet cell antigen 1851 oligonucleotide (SEQ ID NO:18), a 38 bp IC-2/ICA512 oligonucleotide (SEQ ID NO:19) and a 30 bp insulin β-chain probe for pancreatic islets (Petersen et al., *Diabetes* 42:484–95, 1993) (SEQ ID NO:20) were end-labeled with $^{33}$P-DATP (New England Nuclear, Boston, Mass.) using terminal deoxytransferase (GIBCO BRL) according to manufacturer's instructions. Frozen sections (14 μm) from macaque pancreas, adrenal, pituitary and muscle were fixed in 4% paraformaldehyde, followed by acetylation with acetic anhydride and then delipidated in chloroform prior to use.

Labeled probes (2 pmol/ml) were incubated on the sections overnight and then washed in two changes of 1×SSC at 60° C. for 30 minutes, followed by dehydration in ethanol and apposition to autoradiography film (Hyperfilm Betamax, Amersham Corp., Arlington Heights, Ill.) for 2 to 6 days. The slides were then coated with NTB2 Track emulsion (Eastman Kodak, Rochester, N.Y.) and exposed for 12–18 days before development and counterstain with cresyl violet. Images were captured using a Dage 72 CCD camera and a MCID M2 imaging system (Imaging Research, Ontario, Canada). Strong hybridization was detected in pancreatic islets and adrenal medulla but not in muscle. The IA-2/ICA512 and the insulin β chain probes hybridized to islets.

From the foregoing, it will be appreciated that, although specific embodiments of the invention have been described herein for purposes of illustration, various modifications may be made without deviating from the spirit and scope of the invention. Accordingly, the invention is not limited except as by the appended claims.

---

We claim:

1. An isolated polypeptide, consisting of amino acid residues 1 to 417 of SEQ ID NO: 22.

2. The isolated polypeptide of claim 1, wherein the polypeptide further consists of amino acid residues 442 to 818 of SEQ ID NO:22.

3. The isolated polypeptide of claim 2, wherein the polypeptide consists of amino acid residues 1 to 818 of SEQ ID NO:22.

* * * * *

SEQUENCE LISTING (1) GENERAL INFORMATION:

(iii) NUMBER OF SEQUENCES: 34

(2) INFORMATION FOR SEQ ID NO: 1:

(i) SEQUENCE CHARACTERISTICS:
      (A) LENGTH: 2171 base pairs
      (B) TYPE: nucleic acid
      (C) STRANDEDNESS: double
      (D) TOPOLOGY: linear (ii) MOLECULE TYPE: cDNA (ix) FEATURE:
      (A) NAME/KEY: Coding Sequence
      (B) LOCATION: 1...1923
      (D) OTHER INFORMATION:

(xi) SEQUENCE DESCRIPTION: SEQ ID NO: 1:

```
GAA TTC GGC ACG AGC GGA GTT CAG GAC GAC GAT GAC AGA CTT TAC CAA         48
Glu Phe Gly Thr Ser Gly Val Gln Asp Asp Asp Asp Arg Leu Tyr Gln
 1               5                  10                  15

GAG GTC CAT CGT CTG AGT GCC ACA CTC GGG GGC CTC CTG CAG GAC CAC         96
Glu Val His Arg Leu Ser Ala Thr Leu Gly Gly Leu Leu Gln Asp His
                20                  25                  30

GGG TCT CGA CTC TCG CCT GGA GCC CTC CCC TTT GCA AAG CCC CTC AAA        144
Gly Ser Arg Leu Ser Pro Gly Ala Leu Pro Phe Ala Lys Pro Leu Lys
             35                  40                  45

ATG GAG AGG AAG AAA TCC GAG CGC CCT GAG GCT TCC CTG TCT TCA GAA        192
Met Glu Arg Lys Lys Ser Glu Arg Pro Glu Ala Ser Leu Ser Ser Glu
         50                  55                  60

GAG GAG ACT GCC GGA GTG GAG AAC GTC AAG AGC CAG ACG TAT TCC AAA        240
Glu Glu Thr Ala Gly Val Glu Asn Val Lys Ser Gln Thr Tyr Ser Lys
65                  70                  75                  80

GAC CTG CTG GGG CAG CAG CCG CAT TCG GAG CCC GGG GCA GGC GCG TTT        288
Asp Leu Leu Gly Gln Gln Pro His Ser Glu Pro Gly Ala Gly Ala Phe
                85                  90                  95

GGG GAG CTC CAA AAC CAG ATG CCT GGG CCC TCG GAG GAG GAG CAG AGC        336
Gly Glu Leu Gln Asn Gln Met Pro Gly Pro Ser Glu Glu Glu Gln Ser
                100                 105                 110
```

```
CTT CCA GCG GGT GCT CAG GAG GCC CTC GGC GAC GGC CTG CAA TTG GAA    384
Leu Pro Ala Gly Ala Gln Glu Ala Leu Gly Asp Gly Leu Gln Leu Glu
        115                 120                 125

GTC AAG CCT TCC GAG GAA GAG GCA CGG TGC TAC ATC GTG ACA GAC AGA    432
Val Lys Pro Ser Glu Glu Glu Ala Arg Cys Tyr Ile Val Thr Asp Arg
        130                 135                 140

GAC CCC CTG CGC CCC GAG GAA GGA AGG CAG CTG GTG GAG GAC GTC GCC    480
Asp Pro Leu Arg Pro Glu Glu Gly Arg Gln Leu Val Glu Asp Val Ala
145                 150                 155                 160

CGC CTC CTG CAG ATG CCC AGC AGC ACA TTC GCC GAC GTG GAG GTT CTC    528
Arg Leu Leu Gln Met Pro Ser Ser Thr Phe Ala Asp Val Glu Val Leu
                    165                 170                 175

GGA CCA GCA GTG ACC TTC AAA GTG GGC GCC AAT GTC CAG AAC GTG ACC    576
Gly Pro Ala Val Thr Phe Lys Val Gly Ala Asn Val Gln Asn Val Thr
            180                 185                 190

ACT GCG GAT GTG GAG AAG GCC ACA GTT GAC AAC AAA GAC AAA CTG GAG    624
Thr Ala Asp Val Glu Lys Ala Thr Val Asp Asn Lys Asp Lys Leu Glu
        195                 200                 205

GAA ACC TCT GGA CTG AAA ATT CTT CAA ACC GGA GTC GGG TCG AAA AGC    672
Glu Thr Ser Gly Leu Lys Ile Leu Gln Thr Gly Val Gly Ser Lys Ser
    210                 215                 220

AAA CTC AAG TTC CTG CCT CCT CAG GCG GAG CAA GAA GAC TCA ACC AAG    720
Lys Leu Lys Phe Leu Pro Pro Gln Ala Glu Gln Glu Asp Ser Thr Lys
225                 230                 235                 240

TTC ATC GCG CTC ACC CTG GTC TCC CTC GCC TGC ATC CTG GGC GTC CTC    768
Phe Ile Ala Leu Thr Leu Val Ser Leu Ala Cys Ile Leu Gly Val Leu
                245                 250                 255

CTG GCC TCT GGC CTC ATC TAC TGC CTA CGC CAT AGC TCT CAG CAC AGG    816
Leu Ala Ser Gly Leu Ile Tyr Cys Leu Arg His Ser Ser Gln His Arg
            260                 265                 270

CTG AAG GAG AAG CTC TCG GGA CTA GGG CGC GAC CCA GGT GCA GAT GCC    864
Leu Lys Glu Lys Leu Ser Gly Leu Gly Arg Asp Pro Gly Ala Asp Ala
        275                 280                 285

ACC GCC GCC TAC CAG GAG CTG TGC CGC CAG CGT ATG GCC ACG CGG CCA    912
Thr Ala Ala Tyr Gln Glu Leu Cys Arg Gln Arg Met Ala Thr Arg Pro
    290                 295                 300

CCA GAC CGG CCC GAG GGC CCG CAC ACA TCC CGC ATC AGC AGC GTC TCG    960
Pro Asp Arg Pro Glu Gly Pro His Thr Ser Arg Ile Ser Ser Val Ser
305                 310                 315                 320

TCC CAG TTC AGC GAC GGG CCG ATG CCC AGC CCC TCC GCA CGC AG        1008
Ser Gln Phe Ser Asp Gly Pro Met Pro Ser Pro Ser Ala Arg Ser Ser
                325                 330                 335

GCC TCG TCC TGG TCC GAG GAG CCC GTG CAG TCC AAC ATG GAC ATC TC    1056
Ala Ser Ser Trp Ser Glu Glu Pro Val Gln Ser Asn Met Asp Ile Ser
            340                 345                 350

ACC GGC CAC ATG ATC CTG TCC TAC ATG GAG GAC CAC CTG AAG AAC AA    1104
Thr Gly His Met Ile Leu Ser Tyr Met Glu Asp His Leu Lys Asn Lys
        355                 360                 365

AAC CGG CTG GAG AAG GAG TGG GAG GCG CTG TGT GCC TAC CAG GCG GA    1152
Asn Arg Leu Glu Lys Glu Trp Glu Ala Leu Cys Ala Tyr Gln Ala Glu
    370                 375                 380

CCC AAC AGC TCA CTT GTG GCC CAG AAG GAG GAG AAT GTG CCC AAG AA    1200
Pro Asn Ser Ser Leu Val Ala Gln Lys Glu Glu Asn Val Pro Lys Asn
385                 390                 395                 400

CGC TCC CTG GCC GTG CTG ACC TAT GAC CAC TCC CGG GTC CTA CTG AA    1248
Arg Ser Leu Ala Val Leu Thr Tyr Asp His Ser Arg Val Leu Leu Lys
                405                 410                 415

GCG GAG AAC AGC CAC AGC CAC TCG GAC TAC ATC AAC GCC AGC CCC AT    1296
Ala Glu Asn Ser His Ser His Ser Asp Tyr Ile Asn Ala Ser Pro Ile
```

-continued

```
            420                 425                 430
ATG GAT CAC GAC CCG AGG AAC CCC GCG TAC ATC GCC ACC CAG GGA CC      1344
Met Asp His Asp Pro Arg Asn Pro Ala Tyr Ile Ala Thr Gln Gly Pro
            435                 440                 445

CTG CCC GCC ACC GTG GCC GAC TTT TGG CAG ATG GTG TGG GAG AGC GG      1392
Leu Pro Ala Thr Val Ala Asp Phe Trp Gln Met Val Trp Glu Ser Gly
    450                 455                 460

TGC GTG GTG ATC GTC ATG CTG ACA CCC CTC ACA GAG AAC GGC GTC CG      1440
Cys Val Val Ile Val Met Leu Thr Pro Leu Thr Glu Asn Gly Val Arg
465                 470                 475                 480

CAG TGC TAC CAC TAC TGG CCA GAT GAA GGC TCC AAC CTC TAC CAC AT      1488
Gln Cys Tyr His Tyr Trp Pro Asp Glu Gly Ser Asn Leu Tyr His Ile
                485                 490                 495

TAT GAG GTG AAC CTG GTC TCC GAG CAC ATC TGG TGC GAG GAC TTT CT      1536
Tyr Glu Val Asn Leu Val Ser Glu His Ile Trp Cys Glu Asp Phe Leu
            500                 505                 510

GTG AGG AGC TTC TAT CTG AAG AAC CTG CAG ACC AAC GAG ACG CGC AC      1584
Val Arg Ser Phe Tyr Leu Lys Asn Leu Gln Thr Asn Glu Thr Arg Thr
        515                 520                 525

GTG ACC CAG TTC CAC TTC CTG AGT TGG TAT GAC CGA GGA GTC CCC TC      1632
Val Thr Gln Phe His Phe Leu Ser Trp Tyr Asp Arg Gly Val Pro Ser
    530                 535                 540

TCC TCA AGA TCC CTC CTG GAC TTC CGC AGA AAA GTA AAC AAG TGC TA      1680
Ser Ser Arg Ser Leu Leu Asp Phe Arg Arg Lys Val Asn Lys Cys Tyr
545                 550                 555                 560

AGG GGC CGT TCT TGT CCA ATA ATT GTT CAT TGC AGT GAC GGT GCA GG      1728
Arg Gly Arg Ser Cys Pro Ile Ile Val His Cys Ser Asp Gly Ala Gly
                565                 570                 575

CGG AGC GGC ACC TAC GTC CTG ATC GAC ATG GTT CTC AAC AAG ATG GC      1776
Arg Ser Gly Thr Tyr Val Leu Ile Asp Met Val Leu Asn Lys Met Ala
            580                 585                 590

AAA GGT GCT AAA GAG ATT GAT ATC GCA GCA ACC CTG GAG CAC TTG AG      1824
Lys Gly Ala Lys Glu Ile Asp Ile Ala Ala Thr Leu Glu His Leu Arg
        595                 600                 605

GAC CAG AGA CCC GGC ATG GTC CAG ACG AAG GAG CAG TTT GAG TTC GC      1872
Asp Gln Arg Pro Gly Met Val Gln Thr Lys Glu Gln Phe Glu Phe Ala
    610                 615                 620

CTG ACA GCC GTG GCT GAA GAG GTG AAT GCC ATC CTC AAG GCC CTT CC      1920
Leu Thr Ala Val Ala Glu Glu Val Asn Ala Ile Leu Lys Ala Leu Pro
625                 630                 635                 640

CAG TGAGCAGCGG CCTCGGGGCC TCGGGGAGC CCCCACCCCC CGGATGTCGT CAG        1979
Gln

TCGTGATCTG ACTTTAATTG TGTGTCTTCT ATTATAACTG CATAGTAATA GGGCCCT      2039
CTCTCCCGTA GTCAGCGCAG TTTAGCAGTT AAGCAGTTAA AATGTGTATT TTTGTTT     2099

CCAACAATAA TAAAGAGAGA TTTGTGGAAA AATCCCAAAA AAAAAAAAAA AAAAAA      2159
AAAAAACTCG AG                                                      2171
```

(2) INFORMATION FOR SEQ ID NO: 2:

(i) SEQUENCE CHARACTERISTICS:
        (A) LENGTH: 641 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 2:

Glu Phe Gly Thr Ser Gly Val Gln Asp Asp Asp Asp Arg Leu Tyr Gln

-continued

```
  1               5                 10                15
Glu Val His Arg Leu Ser Ala Thr Leu Gly Gly Leu Leu Gln Asp His
                 20              25              30
Gly Ser Arg Leu Ser Pro Gly Ala Leu Pro Phe Ala Lys Pro Leu Lys
             35              40              45
Met Glu Arg Lys Lys Ser Glu Arg Pro Glu Ala Ser Leu Ser Ser Glu
         50              55              60
Glu Glu Thr Ala Gly Val Glu Asn Val Lys Ser Gln Thr Tyr Ser Lys
 65              70              75              80
Asp Leu Leu Gly Gln Gln Pro His Ser Glu Pro Gly Ala Gly Ala Phe
             85              90              95
Gly Glu Leu Gln Asn Gln Met Pro Gly Pro Ser Glu Glu Gln Ser
            100             105             110
Leu Pro Ala Gly Ala Gln Glu Ala Leu Gly Asp Gly Leu Gln Leu Glu
            115             120             125
Val Lys Pro Ser Glu Glu Ala Arg Cys Tyr Ile Val Thr Asp Arg
            130             135             140
Asp Pro Leu Arg Pro Glu Glu Gly Arg Gln Leu Val Glu Asp Val Ala
145             150             155             160
Arg Leu Leu Gln Met Pro Ser Ser Thr Phe Ala Asp Val Glu Val Leu
                165             170             175
Gly Pro Ala Val Thr Phe Lys Val Gly Ala Asn Val Gln Asn Val Thr
            180             185             190
Thr Ala Asp Val Glu Lys Ala Thr Val Asp Asn Lys Asp Lys Leu Glu
            195             200             205
Glu Thr Ser Gly Leu Lys Ile Leu Gln Thr Gly Val Gly Ser Lys Ser
            210             215             220
Lys Leu Lys Phe Leu Pro Pro Gln Ala Glu Gln Glu Asp Ser Thr Lys
225             230             235             240
Phe Ile Ala Leu Thr Leu Val Ser Leu Ala Cys Ile Leu Gly Val Leu
                245             250             255
Leu Ala Ser Gly Leu Ile Tyr Cys Leu Arg His Ser Ser Gln His Arg
            260             265             270
Leu Lys Glu Lys Leu Ser Gly Leu Gly Arg Asp Pro Gly Ala Asp Ala
            275             280             285
Thr Ala Ala Tyr Gln Glu Leu Cys Arg Gln Arg Met Ala Thr Arg Pro
            290             295             300
Pro Asp Arg Pro Glu Gly Pro His Thr Ser Arg Ile Ser Ser Val Ser
305             310             315             320
Ser Gln Phe Ser Asp Gly Pro Met Pro Ser Pro Ser Ala Arg Ser Ser
            325             330             335
Ala Ser Ser Trp Ser Glu Glu Pro Val Gln Ser Asn Met Asp Ile Ser
            340             345             350
Thr Gly His Met Ile Leu Ser Tyr Met Glu Asp His Leu Lys Asn Lys
            355             360             365
Asn Arg Leu Glu Lys Glu Trp Glu Ala Leu Cys Ala Tyr Gln Ala Glu
            370             375             380
Pro Asn Ser Ser Leu Val Ala Gln Lys Glu Glu Asn Val Pro Lys Asn
385             390             395             400
Arg Ser Leu Ala Val Leu Thr Tyr Asp His Ser Arg Val Leu Leu Lys
            405             410             415
Ala Glu Asn Ser His Ser His Ser Asp Tyr Ile Asn Ala Ser Pro Ile
            420             425             430
```

```
Met Asp His Asp Pro Arg Asn Pro Ala Tyr Ile Ala Thr Gln Gly Pro
         435                 440                 445
Leu Pro Ala Thr Val Ala Asp Phe Trp Gln Met Val Trp Glu Ser Gly
    450                 455                 460
Cys Val Val Ile Val Met Leu Thr Pro Leu Thr Glu Asn Gly Val Arg
465                 470                 475                 480
Gln Cys Tyr His Tyr Trp Pro Asp Glu Gly Ser Asn Leu Tyr His Ile
                485                 490                 495
Tyr Glu Val Asn Leu Val Ser Glu His Ile Trp Cys Glu Asp Phe Leu
            500                 505                 510
Val Arg Ser Phe Tyr Leu Lys Asn Leu Gln Thr Asn Glu Thr Arg Thr
        515                 520                 525
Val Thr Gln Phe His Phe Leu Ser Trp Tyr Asp Arg Gly Val Pro Ser
    530                 535                 540
Ser Ser Arg Ser Leu Leu Asp Phe Arg Arg Lys Val Asn Lys Cys Tyr
545                 550                 555                 560
Arg Gly Arg Ser Cys Pro Ile Ile Val His Cys Ser Asp Gly Ala Gly
                565                 570                 575
Arg Ser Gly Thr Tyr Val Leu Ile Asp Met Val Leu Asn Lys Met Ala
            580                 585                 590
Lys Gly Ala Lys Glu Ile Asp Ile Ala Ala Thr Leu Glu His Leu Arg
        595                 600                 605
Asp Gln Arg Pro Gly Met Val Gln Thr Lys Glu Gln Phe Glu Phe Ala
    610                 615                 620
Leu Thr Ala Val Ala Glu Glu Val Asn Ala Ile Leu Lys Ala Leu Pro
625                 630                 635                 640
Gln (2) INFORMATION FOR SEQ ID NO: 3:

(i) SEQUENCE CHARACTERISTICS:
        (A) LENGTH: 894 base pairs
        (B) TYPE: nucleic acid
        (C) STRANDEDNESS: single
        (D) TOPOLOGY: linear (ii) MOLECULE TYPE: cDNA (ix) FEATURE:
        (A) NAME/KEY: Coding Sequence
        (B) LOCATION: 1...894
        (D) OTHER INFORMATION:

(xi) SEQUENCE DESCRIPTION: SEQ ID NO: 3:

CGC CAT AGC TCT CAG CAC AGG CTG AAG GAG AAG CTC TCG GGA CTA GGG  48
Arg His Ser Ser Gln His Arg Leu Lys Glu Lys Leu Ser Gly Leu Gly
 1               5                  10                  15

GGC GAC CCA GGT GCA GAT GCC ACT GCC GCC TAC CAG GAG CTG TGC CGC  96
Gly Asp Pro Gly Ala Asp Ala Thr Ala Ala Tyr Gln Glu Leu Cys Arg
             20                  25                  30

CAG CGT ATG GCC ACG CGG CCA CCA GAC CGA CCT GAG GGC CCG CAC ACG 144
Gln Arg Met Ala Thr Arg Pro Pro Asp Arg Pro Glu Gly Pro His Thr
         35                  40                  45

TCA CGC ATC AGC AGC GTC TCA TCC CAG TTC AGC GAC GGG CCG ATC CCC 192
Ser Arg Ile Ser Ser Val Ser Ser Gln Phe Ser Asp Gly Pro Ile Pro
     50                  55                  60

AGC CCC TCC GCA CGC AGC AGC GCC TCA TCC TGG TCC GAG GAG CCT GTG 240
Ser Pro Ser Ala Arg Ser Ser Ala Ser Ser Trp Ser Glu Glu Pro Val
 65                  70                  75                  80
```

-continued

```
CAG TCC AAC ATG GAC ATC TCC ACC GGC CAC ATG ATC CTG TCC TAC ATG  288
Gln Ser Asn Met Asp Ile Ser Thr Gly His Met Ile Leu Ser Tyr Met
             85                  90                  95

GAG GAC CAC CTG AAG AAC AAG AAC CGG CTG GAG AAG GAG TGG GAA GCG  336
Glu Asp His Leu Lys Asn Lys Asn Arg Leu Glu Lys Glu Trp Glu Ala
                100                 105                 110

CTG TGC GCC TAC CAG GCG GAG CCC AAC AGC TCG TTC GTG GCC CAG AGG  384
Leu Cys Ala Tyr Gln Ala Glu Pro Asn Ser Ser Phe Val Ala Gln Arg
            115                 120                 125

GAG GAG AAC GTG CCC AAG AAC CGC TCC CTG GCC GTG CTG ACC TAT GAC  432
Glu Glu Asn Val Pro Lys Asn Arg Ser Leu Ala Val Leu Thr Tyr Asp
        130                 135                 140

CAC TCC CGG GTC CTG CTG AAG GCG GAG AAC AGC CAC AGC CAC TCA GAC  480
His Ser Arg Val Leu Leu Lys Ala Glu Asn Ser His Ser His Ser Asp
145                 150                 155                 160

TAC ATC AAC GCT AGC CCC ATC ATG GAT CAC GAC CCG AGG AAC CCC GCG  528
Tyr Ile Asn Ala Ser Pro Ile Met Asp His Asp Pro Arg Asn Pro Ala
                165                 170                 175

TAC ATC GCC ACC CAG GGA CCG CTG CCC GCC ACC GTG GCT GAC TTT TGG  576
Tyr Ile Ala Thr Gln Gly Pro Leu Pro Ala Thr Val Ala Asp Phe Trp
            180                 185                 190

CAG ATG GTG TGG GAG AGC GGC TGC GTG GTG ATC GTC ATG CTG ACA CCC  624
Gln Met Val Trp Glu Ser Gly Cys Val Val Ile Val Met Leu Thr Pro
        195                 200                 205

CTC GCG GAG AAC GGC GTC CGG CAG TGC TAC CAC TAC TGG CCG GAT GAA  672
Leu Ala Glu Asn Gly Val Arg Gln Cys Tyr His Tyr Trp Pro Asp Glu
    210                 215                 220

GGC TCC AAT CTC TAC CAC ATC TAT GAG GTG AAC CTG GTC TCC GAG CAC  720
Gly Ser Asn Leu Tyr His Ile Tyr Glu Val Asn Leu Val Ser Glu His
225                 230                 235                 240

ATC TGG TGT GAG GAC TTC CTG GTG AGG AGC TTC TAT CTG AAG AAC CTG  768
Ile Trp Cys Glu Asp Phe Leu Val Arg Ser Phe Tyr Leu Lys Asn Leu
                245                 250                 255

CAG ACC AAC GAG ACG CGC ACC GTG ACG CAG TTC CAC TTC CTG AGT TGG  816
Gln Thr Asn Glu Thr Arg Thr Val Thr Gln Phe His Phe Leu Ser Trp
            260                 265                 270

TAT GAC CGA GGA GTC CCT TCC TCC TCA AGG TCC CTC CTG GAC TTC CGC  864
Tyr Asp Arg Gly Val Pro Ser Ser Ser Arg Ser Leu Leu Asp Phe Arg
        275                 280                 285

AGA AAA GTA AAC AAG TGC TAC AGG GGC CGT                          894
Arg Lys Val Asn Lys Cys Tyr Arg Gly Arg
    290                 295
```

(2) INFORMATION FOR SEQ ID NO: 4:

(i) SEQUENCE CHARACTERISTICS:
        (A) LENGTH: 298 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 4:

```
Arg His Ser Ser Gln His Arg Leu Lys Glu Lys Leu Ser Gly Leu Gly
1               5                   10                  15

Gly Asp Pro Gly Ala Asp Ala Thr Ala Ala Tyr Gln Glu Leu Cys Arg
            20                  25                  30

Gln Arg Met Ala Thr Arg Pro Pro Asp Arg Pro Glu Gly Pro His Thr
```

-continued

```
                35                   40                   45
Ser Arg Ile Ser Ser Val Ser Ser Gln Phe Ser Asp Gly Pro Ile Pro
 50                   55                   60
Ser Pro Ser Ala Arg Ser Ser Ala Ser Ser Trp Ser Glu Glu Pro Val
 65                   70                   75                   80
Gln Ser Asn Met Asp Ile Ser Thr Gly His Met Ile Leu Ser Tyr Met
                 85                   90                   95
Glu Asp His Leu Lys Asn Lys Asn Arg Leu Glu Lys Glu Trp Glu Ala
                100                  105                  110
Leu Cys Ala Tyr Gln Ala Glu Pro Asn Ser Ser Phe Val Ala Gln Arg
                115                  120                  125
Glu Glu Asn Val Pro Lys Asn Arg Ser Leu Ala Val Leu Thr Tyr Asp
130                  135                  140
His Ser Arg Val Leu Leu Lys Ala Glu Asn Ser His Ser His Ser Asp
145                  150                  155                  160
Tyr Ile Asn Ala Ser Pro Ile Met Asp His Asp Pro Arg Asn Pro Ala
                165                  170                  175
Tyr Ile Ala Thr Gln Gly Pro Leu Pro Ala Thr Val Ala Asp Phe Trp
                180                  185                  190
Gln Met Val Trp Glu Ser Gly Cys Val Val Ile Val Met Leu Thr Pro
                195                  200                  205
Leu Ala Glu Asn Gly Val Arg Gln Cys Tyr His Tyr Trp Pro Asp Glu
210                  215                  220
Gly Ser Asn Leu Tyr His Ile Tyr Glu Val Asn Leu Val Ser Glu His
225                  230                  235                  240
Ile Trp Cys Glu Asp Phe Leu Val Arg Ser Phe Tyr Leu Lys Asn Leu
                245                  250                  255
Gln Thr Asn Glu Thr Arg Thr Val Thr Gln Phe His Phe Leu Ser Trp
                260                  265                  270
Tyr Asp Arg Gly Val Pro Ser Ser Ser Arg Ser Leu Leu Asp Phe Arg
                275                  280                  285
Arg Lys Val Asn Lys Cys Tyr Arg Gly Arg
290                  295

(2) INFORMATION FOR SEQ ID NO: 5:

(i) SEQUENCE CHARACTERISTICS:
        (A) LENGTH: 127 amino acids
        (B) TYPE: amino acid
        (C) STRANDEDNESS: single
        (D) TOPOLOGY: linear (ii) MOLECULE TYPE: peptide (xi) SEQUENCE DESCRIPTION: SEQ ID NO: 5:

Ala Ser Pro Ile Met Asp His Asp Pro Arg Asn Pro Ala Tyr Ile Ala
 1                    5                   10                   15
Thr Gln Gly Pro Leu Pro Ala Thr Val Ala Asp Phe Trp Gln Met Val
                 20                   25                   30
Trp Glu Ser Gly Cys Val Val Ile Val Met Leu Thr Pro Leu Ala Glu
                 35                   40                   45
Asn Gly Val Arg Gln Cys Tyr His Tyr Trp Pro Asp Glu Gly Ser Asn
 50                   55                   60
Leu Tyr His Ile Tyr Glu Val Asn Leu Val Ser Glu His Ile Trp Cys
 65                   70                   75                   80
Glu Asp Phe Leu Val Arg Ser Phe Tyr Leu Lys Asn Leu Gln Thr Asn
```

```
                        85                  90                  95
Glu Thr Arg Thr Val Thr Gln Phe Pro Leu Ser Xaa Trp Tyr Asp Arg
            100                 105                 110

Xaa Val Pro Ser Phe Leu Lys Val Pro Xaa Trp Thr Ser Ala Glu
            115                 120                 125

(2) INFORMATION FOR SEQ ID NO: 6:

(i) SEQUENCE CHARACTERISTICS:
        (A) LENGTH: 1163 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 27...1154
        (D) OTHER INFORMATION:

(xi) SEQUENCE DESCRIPTION: SEQ ID NO: 6:

AAGCTATGCA TCAAGCTTCC ACCATG CGC CAT AGC TCT CAG CAC AGG CTG AAG       53
                              Arg His Ser Ser Gln His Arg Leu Lys
                               1               5

GAG AAG CTC TCG GGA CTA GGG GGC GAC CCA GGT GCA GAT GCC ACT GCC       101
Glu Lys Leu Ser Gly Leu Gly Gly Asp Pro Gly Ala Asp Ala Thr Ala
 10              15                  20                  25

GCC TAC CAG GAG CTG TGC CGC CAG CGT ATG GCC ACG CGG CCA CCA GAC       149
Ala Tyr Gln Glu Leu Cys Arg Gln Arg Met Ala Thr Arg Pro Pro Asp
                 30                  35                  40

CGA CCT GAG GGC CCG CAC ACG TCA CGC ATC AGC AGC GTC TCA TCC CAG       197
Arg Pro Glu Gly Pro His Thr Ser Arg Ile Ser Ser Val Ser Ser Gln
             45                  50                  55

TTC AGC GAC GGG CCG ATC CCC AGC CCC TCC GCA CGC AGC AGC GCC TCA       245
Phe Ser Asp Gly Pro Ile Pro Ser Pro Ser Ala Arg Ser Ser Ala Ser
         60                  65                  70

TCC TGG TCC GAG GAG CCT GTG CAG TCC AAC ATG GAC ATC TCC ACC GGC       293
Ser Trp Ser Glu Glu Pro Val Gln Ser Asn Met Asp Ile Ser Thr Gly
 75                  80                  85

CAC ATG ATC CTG TCC TAC ATG GAG GAC CAC CTG AAG AAC AAG AAC CGG       341
His Met Ile Leu Ser Tyr Met Glu Asp His Leu Lys Asn Lys Asn Arg
 90              95                 100                 105

CTG GAG AAG GAG TGG GAA GCG CTG TGC GCC TAC CAG GCG GAG CCC AAC       389
Leu Glu Lys Glu Trp Glu Ala Leu Cys Ala Tyr Gln Ala Glu Pro Asn
                110                 115                 120

AGC TCG TTC GTG GCC CAG AGG GAG GAG AAC GTG CCC AAG AAC CGC TCC       437
Ser Ser Phe Val Ala Gln Arg Glu Glu Asn Val Pro Lys Asn Arg Ser
            125                 130                 135

CTG GCC GTG CTG ACC TAT GAC CAC TCC CGG GTC CTG CTG AAG GCG GAG       485
Leu Ala Val Leu Thr Tyr Asp His Ser Arg Val Leu Leu Lys Ala Glu
        140                 145                 150

AAC AGC CAC AGC CAC TCA GAC TAC ATC AAC GCT AGC CCC ATC ATG GAT       533
Asn Ser His Ser His Ser Asp Tyr Ile Asn Ala Ser Pro Ile Met Asp
    155                 160                 165

CAC GAC CCG AGG AAC CCC GCG TAC ATC GCC ACC CAG GGA CCG CTG CCC       581
His Asp Pro Arg Asn Pro Ala Tyr Ile Ala Thr Gln Gly Pro Leu Pro
170                 175                 180                 185

GCC ACC GTG GCT GAC TTT TGG CAG ATG GTG TGG GAG AGC GGC TGC GTG       629
Ala Thr Val Ala Asp Phe Trp Gln Met Val Trp Glu Ser Gly Cys Val
                190                 195                 200

GTG ATC GTC ATG CTG ACA CCC CTC GCG GAG AAC GGC GTC CGG CAG TGC       677
```

-continued

```
                Val Ile Val Met Leu Thr Pro Leu Ala Glu Asn Gly Val Arg Gln Cys
                            205                 210                 215

TAC CAC TAC TGG CCG GAT GAA GGC TCC AAT CTC TAC CAC ATC TAT GAG                725
Tyr His Tyr Trp Pro Asp Glu Gly Ser Asn Leu Tyr His Ile Tyr Glu
        220                 225                 230

GTG AAC CTG GTC TCC GAG CAC ATC TGG TGT GAG GAC TTC CTG GTG AGG                773
Val Asn Leu Val Ser Glu His Ile Trp Cys Glu Asp Phe Leu Val Arg
235                 240                 245

AGC TTC TAT CTG AAG AAC CTG CAG ACC AAC GAG ACG CGC ACC GTG ACG                821
Ser Phe Tyr Leu Lys Asn Leu Gln Thr Asn Glu Thr Arg Thr Val Thr
250                 255                 260                 265

CAG TTC CAC TTC CTG AGT TGG TAT GAC CGA GGA GTC CCT TCC TCC TCA                869
Gln Phe His Phe Leu Ser Trp Tyr Asp Arg Gly Val Pro Ser Ser Ser
                270                 275                 280

AGG TCC CTC CTG GAC TTC CGC AGA AAA GTA AAC AAG TGC TAC AGG GGC                917
Arg Ser Leu Leu Asp Phe Arg Arg Lys Val Asn Lys Cys Tyr Arg Gly
            285                 290                 295

CGT TCT TGT CCA ATA ATT GTT CAT TGC AGT GAC GGT GCA GGC CGG AGC                965
Arg Ser Cys Pro Ile Ile Val His Cys Ser Asp Gly Ala Gly Arg Ser
                300                 305                 310

GGC ACC TAC GTC CTG ATC GAC ATG GTT CTC AAC AAG ATG GCC AAA GG                1013
Gly Thr Tyr Val Leu Ile Asp Met Val Leu Asn Lys Met Ala Lys Gly
            315                 320                 325

GCT AAA GAG ATT GAT ATC GCA GCG ACC CTG GAG CAC TTG AGG GAC CA                1061
Ala Lys Glu Ile Asp Ile Ala Ala Thr Leu Glu His Leu Arg Asp Gln
330                 335                 340                 345

AGA CCC GGC ATG GTC CAG ACG AAG GAG CAG TTT GAG TTC GCG CTG AC                1109
Arg Pro Gly Met Val Gln Thr Lys Glu Gln Phe Glu Phe Ala Leu Thr
                350                 355                 360

GCC GTG GCT GAG GAG GTG AAC GCC ATC CTC AAG GCC CTG CCC CAG TG                1159
Ala Val Ala Glu Glu Val Asn Ala Ile Leu Lys Ala Leu Pro Gln
            365                 370                 375

ATTC                                                                          1163
```

(2) INFORMATION FOR SEQ ID NO: 7:

(i) SEQUENCE CHARACTERISTICS:
 (A) LENGTH: 376 amino acids
 (B) TYPE: amino acid
 (C) STRANDEDNESS: single
 (D) TOPOLOGY: linear (ii) MOLECULE TYPE: protein (v) FRAGMENT TYPE: internal (xi) SEQUENCE DESCRIPTION: SEQ ID NO: 7:

```
Arg His Ser Ser Gln His Arg Leu Lys Glu Lys Leu Ser Gly Leu Gly
1               5                   10                  15

Gly Asp Pro Gly Ala Asp Ala Thr Ala Ala Tyr Gln Glu Leu Cys Arg
            20                  25                  30

Gln Arg Met Ala Thr Arg Pro Pro Asp Arg Pro Glu Gly Pro His Thr
        35                  40                  45

Ser Arg Ile Ser Ser Val Ser Ser Gln Phe Ser Asp Gly Pro Ile Pro
    50                  55                  60

Ser Pro Ser Ala Arg Ser Ser Ala Ser Ser Trp Ser Glu Glu Pro Val
65                  70                  75                  80

Gln Ser Asn Met Asp Ile Ser Thr Gly His Met Ile Leu Ser Tyr Met
                85                  90                  95

Glu Asp His Leu Lys Asn Lys Asn Arg Leu Glu Lys Glu Trp Glu Ala
```

```
                    100                 105                 110
Leu Cys Ala Tyr Gln Ala Glu Pro Asn Ser Ser Phe Val Ala Gln Arg
            115                 120                 125
Glu Glu Asn Val Pro Lys Asn Arg Ser Leu Ala Val Leu Thr Tyr Asp
130                 135                 140
His Ser Arg Val Leu Leu Lys Ala Glu Asn Ser His Ser His Ser Asp
145                 150                 155                 160
Tyr Ile Asn Ala Ser Pro Ile Met Asp His Asp Pro Arg Asn Pro Ala
                165                 170                 175
Tyr Ile Ala Thr Gln Gly Pro Leu Pro Ala Thr Val Ala Asp Phe Trp
                180                 185                 190
Gln Met Val Trp Glu Ser Gly Cys Val Val Ile Val Met Leu Thr Pro
            195                 200                 205
Leu Ala Glu Asn Gly Val Arg Gln Cys Tyr His Tyr Trp Pro Asp Glu
210                 215                 220
Gly Ser Asn Leu Tyr His Ile Tyr Glu Val Asn Leu Val Ser Glu His
225                 230                 235                 240
Ile Trp Cys Glu Asp Phe Leu Val Arg Ser Phe Tyr Leu Lys Asn Leu
                245                 250                 255
Gln Thr Asn Glu Thr Arg Thr Val Thr Gln Phe His Phe Leu Ser Trp
                260                 265                 270
Tyr Asp Arg Gly Val Pro Ser Ser Arg Ser Leu Leu Asp Phe Arg
275                 280                 285
Arg Lys Val Asn Lys Cys Tyr Arg Gly Arg Ser Cys Pro Ile Ile Val
            290                 295                 300
His Cys Ser Asp Gly Ala Gly Arg Ser Gly Thr Tyr Val Leu Ile Asp
305                 310                 315                 320
Met Val Leu Asn Lys Met Ala Lys Gly Ala Lys Glu Ile Asp Ile Ala
                325                 330                 335
Ala Thr Leu Glu His Leu Arg Asp Gln Arg Pro Gly Met Val Gln Thr
                340                 345                 350
Lys Glu Gln Phe Glu Phe Ala Leu Thr Ala Val Ala Glu Glu Val Asn
            355                 360                 365
Ala Ile Leu Lys Ala Leu Pro Gln
            370                 375

(2) INFORMATION FOR SEQ ID NO: 8:

(i) SEQUENCE CHARACTERISTICS:
        (A) LENGTH: 49 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC3747

(xi) SEQUENCE DESCRIPTION: SEQ ID NO: 8:

GGGAATAACA TGTGAATGAC AAAATAAAAT GATAGCTTGC GCTTTTGCG         49

(2) INFORMATION FOR SEQ ID NO: 9:

(i) SEQUENCE CHARACTERISTICS:
        (A) LENGTH: 39 base pairs
        (B) TYPE: nucleic acid
        (C) STRANDEDNESS: single
        (D) TOPOLOGY: linear
```

```
        (ii) MOLECULE TYPE: Other (vii) IMMEDIATE SOURCE:
             (B) CLONE: ZC8802

(xi) SEQUENCE DESCRIPTION: SEQ ID NO: 9:

GCGCCTCGAG CCACCATGCA GCATGCGCGG CAGCAAGAC                                  39

(2) INFORMATION FOR SEQ ID NO: 10:

(i) SEQUENCE CHARACTERISTICS:
             (A) LENGTH: 31 base pairs
             (B) TYPE: nucleic acid
             (C) STRANDEDNESS: single
             (D) TOPOLOGY: linear (ii) MOLECULE TYPE: Other (vii) IMMEDIATE SOURCE:
             (B) CLONE: ZC8803

(xi) SEQUENCE DESCRIPTION: SEQ ID NO: 10:

GCGCGAATTC TCACTGGGGC AGGGCCTTGA G                                          31

(2) INFORMATION FOR SEQ ID NO: 11:

(i) SEQUENCE CHARACTERISTICS:
             (A) LENGTH: 17 base pairs
             (B) TYPE: nucleic acid
             (C) STRANDEDNESS: single
             (D) TOPOLOGY: linear (ii) MOLECULE TYPE: Other (vii) IMMEDIATE SOURCE:
             (B) CLONE: ZC10011

(xi) SEQUENCE DESCRIPTION: SEQ ID NO: 11:

TGTACGCGGG GTTCCTC                                                          17

(2) INFORMATION FOR SEQ ID NO: 12:

(i) SEQUENCE CHARACTERISTICS:
             (A) LENGTH: 25 base pairs
             (B) TYPE: nucleic acid
             (C) STRANDEDNESS: single
             (D) TOPOLOGY: linear (ii) MOLECULE TYPE: Other (vii) IMMEDIATE SOURCE:
             (B) CLONE: ZC10177

(xi) SEQUENCE DESCRIPTION: SEQ ID NO: 12:

GAGGAACCCC GCGTACATCG CCACC                                                 25

(2) INFORMATION FOR SEQ ID NO: 13:

(i) SEQUENCE CHARACTERISTICS:
             (A) LENGTH: 11 amino acids
             (B) TYPE: amino acid
             (C) STRANDEDNESS: single
             (D) TOPOLOGY: linear (ii) MOLECULE TYPE: peptide (ix) FEATURE:

(xi) SEQUENCE DESCRIPTION: SEQ ID NO: 13:
```

```
Val His Cys Xaa Ala Gly Xaa Xaa Arg Xaa Gly
 1               5                  10
```

(2) INFORMATION FOR SEQ ID NO: 14:

(i) SEQUENCE CHARACTERISTICS:
        (A) LENGTH: 18 base pairs
        (B) TYPE: nucleic acid
        (C) STRANDEDNESS: single
        (D) TOPOLOGY: linear (xi) SEQUENCE DESCRIPTION: SEQ ID NO: 14:

```
AARGCNACNG TNGAYAAY                                                18
```

(2) INFORMATION FOR SEQ ID NO: 15:

(i) SEQUENCE CHARACTERISTICS:
        (A) LENGTH: 3287 base pairs
        (B) TYPE: nucleic acid
        (C) STRANDEDNESS: double
        (D) TOPOLOGY: linear (ii) MOLECULE TYPE: cDNA (ix) FEATURE:
        (A) NAME/KEY: Coding Sequence
        (B) LOCATION: 4...3039
        (D) OTHER INFORMATION:

(xi) SEQUENCE DESCRIPTION: SEQ ID NO: 15:

```
AGG GCG CTC CCG CTG CTG TTG CTG CTA CTG CTG CTG CTG CCG CCA CGC     48
    Ala Leu Pro Leu Leu Leu Leu Leu Leu Leu Leu Pro Pro Arg
     1               5                  10                  15

GTC CTG CCT GCC GCC CCC TCG TCC GTC CCC CAC GGC CGG CAG CTC CCG     96
Val Leu Pro Ala Ala Pro Ser Ser Val Pro His Gly Arg Gln Leu Pro
                 20                  25                  30

GGG CGC CTG GGC TGC CTA CTC GAG GAG GGC CTC TGC GGA GCG TCC GAG    144
Gly Arg Leu Gly Cys Leu Leu Glu Glu Gly Leu Cys Gly Ala Ser Glu
             35                  40                  45

GCC TGT GTG AAC GAT GGA GTG TTT GGA AGG TGC CAG AAG GTT CCG GCA    192
Ala Cys Val Asn Asp Gly Val Phe Gly Arg Cys Gln Lys Val Pro Ala
         50                  55                  60

ATG GAC TTT TAC CGC TAC GAG GTG TCG CCC GTG GCC CTG CAG CGC CTG    240
Met Asp Phe Tyr Arg Tyr Glu Val Ser Pro Val Ala Leu Gln Arg Leu
 65                  70                  75

CGC GTG GCT TTG CAG AAA CTC TCC GGC ACA GGT TTC ACG TGG CAG GAT    288
Arg Val Ala Leu Gln Lys Leu Ser Gly Thr Gly Phe Thr Trp Gln Asp
 80                  85                  90                  95

GAC TAT ACT CAG TAT GTG ATG GAC CAG GAA CTT GCA GAC CTC CCC AAA    336
Asp Tyr Thr Gln Tyr Val Met Asp Gln Glu Leu Ala Asp Leu Pro Lys
                100                 105                 110

ACC TAC CTG AGG CAT CCT GAA GCG TCC GGC CCA GCC AGG CCC TCA AAA    384
Thr Tyr Leu Arg His Pro Glu Ala Ser Gly Pro Ala Arg Pro Ser Lys
            115                 120                 125

CAC AGC ATT GGC AGT GAG AGG AGG TAC AGT CGG GAG GGC GGC GCT GCC    432
His Ser Ile Gly Ser Glu Arg Arg Tyr Ser Arg Glu Gly Gly Ala Ala
        130                 135                 140

CTG GCC AAG GCC TTC CGA CGC CAC CTG CCC TTC CTG GAG GCC CTG TCC    480
Leu Ala Lys Ala Phe Arg Arg His Leu Pro Phe Leu Glu Ala Leu Ser
    145                 150                 155

CAG GCC CCA GCT TCA GAC GCG CTC GCC AGG ACC CGG ATG GCG CAG GAC    528
Gln Ala Pro Ala Ser Asp Ala Leu Ala Arg Thr Arg Met Ala Gln Asp
160                 165                 170                 175

AGA CCC CGT GCT GAG GGT GAC GAC CGC TTC TCC AAG AGC ATC CTG ACC    576
```

```
                                                                -continued

Arg Pro Arg Ala Glu Gly Asp Asp Arg Phe Ser Lys Ser Ile Leu Thr
                180                 185                 190

TAT GTG GCC CAC ACG TCT GTG CTG ACC TAC CCT CCC GGG CCC CAG GCC      624
Tyr Val Ala His Thr Ser Val Leu Thr Tyr Pro Pro Gly Pro Gln Ala
            195                 200                 205

CAG CTC CCC GAG GAC CTC CTG CCA CGG ACC CTC AGC CAG CTC CAG CCA      672
Gln Leu Pro Glu Asp Leu Leu Pro Arg Thr Leu Ser Gln Leu Gln Pro
        210                 215                 220

GAC GAG CTC AGC CCT AAG GTG GAC AGC AGT GTG GAG AGA CAC CAT CTG      720
Asp Glu Leu Ser Pro Lys Val Asp Ser Ser Val Glu Arg His His Leu
    225                 230                 235

ATG GCA GCC CTC AGT GCC TAT GCT GCC CAG AGG CCC CCA GCT CCC CCT      768
Met Ala Ala Leu Ser Ala Tyr Ala Ala Gln Arg Pro Pro Ala Pro Pro
240                 245                 250                 255

GGG AAG GGC AGC CTG GAG CCG CAG TAC CTT CTG CGC GCC CCG TCC AGA      816
Gly Lys Gly Ser Leu Glu Pro Gln Tyr Leu Leu Arg Ala Pro Ser Arg
                260                 265                 270

ATG CCC AGG CCC TTG TTG TCG CCA GCC GTC CCC CAG AAG TGG CCT TCA      864
Met Pro Arg Pro Leu Leu Ser Pro Ala Val Pro Gln Lys Trp Pro Ser
            275                 280                 285

CCT CTG GGA GAT CCT GAA GAC CCC CCC AGC ACA GGG GAA GGA GCA CGG      912
Pro Leu Gly Asp Pro Glu Asp Pro Pro Ser Thr Gly Glu Gly Ala Arg
        290                 295                 300

ATT CAC ACT CTC CTG AAG GAC CTG CAG AGG CAG CCG GCT GAG GCG AGG      960
Ile His Thr Leu Leu Lys Asp Leu Gln Arg Gln Pro Ala Glu Ala Arg
    305                 310                 315

GGC CTG AGT GAC CTG GAG CTG GAC AGC ATG GCC GAG CTG ATG GCT GGC     1008
Gly Leu Ser Asp Leu Glu Leu Asp Ser Met Ala Glu Leu Met Ala Gly
320                 325                 330                 335

CTG ATG CAA GGC ATG GAC CAC AGA GGA GCT CTA GGC GGC CCT GGG AAA     1056
Leu Met Gln Gly Met Asp His Arg Gly Ala Leu Gly Gly Pro Gly Lys
                340                 345                 350

GCG GCC CTG GGA GAG TCT GGA GAA CAG GCG GAT GGC CCC AAG GCC GCC     1104
Ala Ala Leu Gly Glu Ser Gly Glu Gln Ala Asp Gly Pro Lys Ala Ala
            355                 360                 365

CTC CGT GGG GAA AGC TTT CCA GAT GAC GGA GTT CAG GAC GAC GAT GAC     1152
Leu Arg Gly Glu Ser Phe Pro Asp Asp Gly Val Gln Asp Asp Asp Asp
        370                 375                 380

AGA CTT TAC CAA GAG GTC CAT CGT CTG AGT GCC ACA CTC GGG GGC CTC     1200
Arg Leu Tyr Gln Glu Val His Arg Leu Ser Ala Thr Leu Gly Gly Leu
    385                 390                 395

CTG CAG GAC CAC GGG TCT CGA CTC TCG CCT GGA GCC CTC CCC TTT GCA     1248
Leu Gln Asp His Gly Ser Arg Leu Ser Pro Gly Ala Leu Pro Phe Ala
400                 405                 410                 415

AAG CCC CTC AAA ATG GAG AGG AAG AAA TCC GAG CGC CCT GAG GCT TCC     1296
Lys Pro Leu Lys Met Glu Arg Lys Lys Ser Glu Arg Pro Glu Ala Ser
                420                 425                 430

CTG TCT TCA GAA GAG GAG ACT GCC GGA GTG GAG AAC GTC AAG AGC CAG     1344
Leu Ser Ser Glu Glu Glu Thr Ala Gly Val Glu Asn Val Lys Ser Gln
            435                 440                 445

ACG TAT TCC AAA GAC CTG CTG GGG CAG CAG CCG CAT TCG GAG CCC GGG     1392
Thr Tyr Ser Lys Asp Leu Leu Gly Gln Gln Pro His Ser Glu Pro Gly
        450                 455                 460

GCA GGC GCG TTT GGG GAG CTC CAA AAC CAG ATG CCT GGG CCC TCG GAG     1440
Ala Gly Ala Phe Gly Glu Leu Gln Asn Gln Met Pro Gly Pro Ser Glu
    465                 470                 475

GAG GAG CAG AGC CTT CCA GCG GGT GCT CAG GAG GCC CTC GGC GAC GGC     1488
Glu Glu Gln Ser Leu Pro Ala Gly Ala Gln Glu Ala Leu Gly Asp Gly
480                 485                 490                 495
```

-continued

```
CTG CAA TTG GAA GTC AAG CCT TCC GAG GAA GAG GCA CGG TGC TAC ATC         1536
Leu Gln Leu Glu Val Lys Pro Ser Glu Glu Glu Ala Arg Cys Tyr Ile
            500                 505                 510

GTG ACA GAC AGA GAC CCC CTG CGC CCC GAG GAA GGA AGG CAG CTG GTG         1584
Val Thr Asp Arg Asp Pro Leu Arg Pro Glu Glu Gly Arg Gln Leu Val
            515                 520                 525

GAG GAC GTC GCC CGC CTC CTG CAG ATG CCC AGC AGC ACA TTC GCC GAC         1632
Glu Asp Val Ala Arg Leu Leu Gln Met Pro Ser Ser Thr Phe Ala Asp
            530                 535                 540

GTG GAG GTT CTC GGA CCA GCA GTG ACC TTC AAA GTG GGC GCC AAT GTC         1680
Val Glu Val Leu Gly Pro Ala Val Thr Phe Lys Val Gly Ala Asn Val
            545                 550                 555

CAG AAC GTG ACC ACT GCG GAT GTG GAG AAG GCC ACA GTT GAC AAC AAA         1728
Gln Asn Val Thr Thr Ala Asp Val Glu Lys Ala Thr Val Asp Asn Lys
560                 565                 570                 575

GAC AAA CTG GAG GAA ACC TCT GGA CTA AAA ATT CTT CAA ACC GGA GTC         1776
Asp Lys Leu Glu Glu Thr Ser Gly Leu Lys Ile Leu Gln Thr Gly Val
            580                 585                 590

GGG TCG AAA AGC AAA CTC AAG TTC CTG CCT CCT CAG GCG GAG CAA GAA         1824
Gly Ser Lys Ser Lys Leu Lys Phe Leu Pro Pro Gln Ala Glu Gln Glu
            595                 600                 605

GAC TCA ACC AAG TTC ATC GCG CTC ACC CTG GTC TCC CTC GCC TGC ATC         1872
Asp Ser Thr Lys Phe Ile Ala Leu Thr Leu Val Ser Leu Ala Cys Ile
            610                 615                 620

CTG GGC GTC CTC CTG GCC TCT GGC CTC ATC TAC TGC CTA CGC CAT AGC         1920
Leu Gly Val Leu Leu Ala Ser Gly Leu Ile Tyr Cys Leu Arg His Ser
625                 630                 635

TCT CAG CAC AGG CTG AAG GAG AAG CTC TCG GGA CTA GGG CGC GAC CCA         1968
Ser Gln His Arg Leu Lys Glu Lys Leu Ser Gly Leu Gly Arg Asp Pro
640                 645                 650                 655

GGT GCA GAT GCC ACC GCC GCC TAC CAG GAG CTG TGC CGC CAG CGT ATG         2016
Gly Ala Asp Ala Thr Ala Ala Tyr Gln Glu Leu Cys Arg Gln Arg Met
            660                 665                 670

GCC ACG CGG CCA CCA GAC CGG CCC GAG GGC CCG CAC ACA TCC CGC ATC         2064
Ala Thr Arg Pro Pro Asp Arg Pro Glu Gly Pro His Thr Ser Arg Ile
            675                 680                 685

AGC AGC GTC TCG TCC CAG TTC AGC GAC GGG CCG ATG CCC AGC CCC TCC         2112
Ser Ser Val Ser Ser Gln Phe Ser Asp Gly Pro Met Pro Ser Pro Ser
            690                 695                 700

GCA CGC AGC AGC GCC TCG TCC TGG TCC GAG GAG CCC GTG CAG TCC AAC         2160
Ala Arg Ser Ser Ala Ser Ser Trp Ser Glu Glu Pro Val Gln Ser Asn
705                 710                 715

ATG GAC ATC TCC ACC GGC CAC ATG ATC CTG TCC TAC ATG GAG GAC CAC         2208
Met Asp Ile Ser Thr Gly His Met Ile Leu Ser Tyr Met Glu Asp His
720                 725                 730                 735

CTG AAG AAC AAG AAC CGG CTG GAG AAG GAG TGG GAG GCG CTG TGT GCC         2256
Leu Lys Asn Lys Asn Arg Leu Glu Lys Glu Trp Glu Ala Leu Cys Ala
            740                 745                 750

TAC CAG GCG GAG CCC AAC AGC TCA CTT GTG GCC CAG AAG GAG GAG AAT         2304
Tyr Gln Ala Glu Pro Asn Ser Ser Leu Val Ala Gln Lys Glu Glu Asn
            755                 760                 765

GTG CCC AAG AAC CGC TCC CTG GCC GTG CTG ACC TAT GAC CAC TCC CGG         2352
Val Pro Lys Asn Arg Ser Leu Ala Val Leu Thr Tyr Asp His Ser Arg
            770                 775                 780

GTC CTA CTG AAG GCG GAG AAC AGC CAC AGC CAC TCG GAC TAC ATC AAC         2400
Val Leu Leu Lys Ala Glu Asn Ser His Ser His Ser Asp Tyr Ile Asn
785                 790                 795

GCC AGC CCC ATC ATG GAT CAC GAC CCG AGG AAC CCC GCG TAC ATC GCC         2448
Ala Ser Pro Ile Met Asp His Asp Pro Arg Asn Pro Ala Tyr Ile Ala
800                 805                 810                 815
```

-continued

```
ACC CAG GGA CCG CTG CCC GCC ACC GTG GCC GAC TTT TGG CAG ATG GTG     2496
Thr Gln Gly Pro Leu Pro Ala Thr Val Ala Asp Phe Trp Gln Met Val
            820                 825                 830

TGG GAG AGC GGC TGC GTG GTG ATC GTC ATG CTG ACA CCC CTC ACA GAG     2544
Trp Glu Ser Gly Cys Val Val Ile Val Met Leu Thr Pro Leu Thr Glu
        835                 840                 845

AAC GGC GTC CGG CAG TGC TAC CAC TAC TGG CCA GAT GAA GGC TCC AAC     2592
Asn Gly Val Arg Gln Cys Tyr His Tyr Trp Pro Asp Glu Gly Ser Asn
    850                 855                 860

CTC TAC CAC ATC TAT GAG GTG AAC CTG GTC TCC GAG CAC ATC TGG TGC     2640
Leu Tyr His Ile Tyr Glu Val Asn Leu Val Ser Glu His Ile Trp Cys
865                 870                 875

GAG GAC TTT CTG GTG AGG AGC TTC TAT CTG AAG AAC CTG CAG ACC AAC     2688
Glu Asp Phe Leu Val Arg Ser Phe Tyr Leu Lys Asn Leu Gln Thr Asn
880                 885                 890                 895

GAG ACG CGC ACC GTG ACC CAG TTC CAC TTC CTG AGT TGG TAT GAC CGA     2736
Glu Thr Arg Thr Val Thr Gln Phe His Phe Leu Ser Trp Tyr Asp Arg
            900                 905                 910

GGA GTC CCC TCC TCC TCA AGA TCC CTC CTG GAC TTC CGC AGA AAA GTA     2784
Gly Val Pro Ser Ser Ser Arg Ser Leu Leu Asp Phe Arg Arg Lys Val
        915                 920                 925

AAC AAG TGC TAC AGG GGC CGT TCT TGT CCA ATA ATT GTT CAT TGC AGT     2832
Asn Lys Cys Tyr Arg Gly Arg Ser Cys Pro Ile Ile Val His Cys Ser
    930                 935                 940

GAC GGT GCA GGC CGG AGC GGC ACC TAC GTC CTG ATC GAC ATG GTT CTC     2880
Asp Gly Ala Gly Arg Ser Gly Thr Tyr Val Leu Ile Asp Met Val Leu
945                 950                 955

AAC AAG ATG GCC AAA GGT GCT AAA GAG ATT GAT ATC GCA GCA ACC CTG     2928
Asn Lys Met Ala Lys Gly Ala Lys Glu Ile Asp Ile Ala Ala Thr Leu
960                 965                 970                 975

GAG CAC TTG AGG GAC CAG AGA CCC GGC ATG GTC CAG ACG AAG GAG CAG     2976
Glu His Leu Arg Asp Gln Arg Pro Gly Met Val Gln Thr Lys Glu Gln
            980                 985                 990

TTT GAG TTC GCG CTG ACA GCC GTG GCT GAA GAG GTG AAT GCC ATC CTC     3024
Phe Glu Phe Ala Leu Thr Ala Val Ala Glu Glu Val Asn Ala Ile Leu
        995                 1000                1005

AAG GCC CTT CCC CAG TGAGCAGCGG CCTCGGGGCC TCGGGGAGC CCCCACCCC  C    3080
Lys Ala Leu Pro Gln
                1010

GGATGTCGTC AGGAATCGTG ATCTGACTTT AATTGTGTGT CTTCTATTAT AACTGCATAG   3140

TAATAGGGCC CTTAGCTCTC CCGTAGTCAG CGCAGTTTAG CAGTTAAGCA GTTAAAATGT   3200

GTATTTTTGT TTAATCCAAC AATAATAAAG AGAGATTTGT GGAAAAATCC CAAAAAAAAA   3260

AAAAAAAAAA AAAAAAAAAA ACTCGAG                                      3287

(2) INFORMATION FOR SEQ ID NO: 16:

(i) SEQUENCE CHARACTERISTICS:
        (A) LENGTH: 1012 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 16:

Ala Leu Pro Leu Leu Leu Leu Leu Leu Leu Leu Pro Pro Arg Val
1               5                   10                  15
```

-continued

```
Leu Pro Ala Ala Pro Ser Ser Val Pro His Gly Arg Gln Leu Pro Gly
             20                  25                  30

Arg Leu Gly Cys Leu Leu Glu Glu Gly Leu Cys Gly Ala Ser Glu Ala
         35                  40                  45

Cys Val Asn Asp Gly Val Phe Gly Arg Cys Gln Lys Val Pro Ala Met
 50                  55                  60

Asp Phe Tyr Arg Tyr Glu Val Ser Pro Val Ala Leu Gln Arg Leu Arg
 65                  70                  75                  80

Val Ala Leu Gln Lys Leu Ser Gly Thr Gly Phe Thr Trp Gln Asp Asp
                 85                  90                  95

Tyr Thr Gln Tyr Val Met Asp Gln Glu Leu Ala Asp Leu Pro Lys Thr
            100                 105                 110

Tyr Leu Arg His Pro Glu Ala Ser Gly Pro Ala Arg Pro Ser Lys His
            115                 120                 125

Ser Ile Gly Ser Glu Arg Arg Tyr Ser Arg Glu Gly Gly Ala Ala Leu
            130                 135                 140

Ala Lys Ala Phe Arg Arg His Leu Pro Phe Leu Glu Ala Leu Ser Gln
145                 150                 155                 160

Ala Pro Ala Ser Asp Ala Leu Ala Arg Thr Arg Met Ala Gln Asp Arg
                165                 170                 175

Pro Arg Ala Glu Gly Asp Asp Arg Phe Ser Lys Ser Ile Leu Thr Tyr
            180                 185                 190

Val Ala His Thr Ser Val Leu Thr Tyr Pro Gly Pro Gln Ala Gln
            195                 200                 205

Leu Pro Glu Asp Leu Leu Pro Arg Thr Leu Ser Gln Leu Gln Pro Asp
            210                 215                 220

Glu Leu Ser Pro Lys Val Asp Ser Ser Val Glu Arg His His Leu Met
225                 230                 235                 240

Ala Ala Leu Ser Ala Tyr Ala Ala Gln Arg Pro Pro Ala Pro Pro Gly
                245                 250                 255

Lys Gly Ser Leu Glu Pro Gln Tyr Leu Leu Arg Ala Pro Ser Arg Met
            260                 265                 270

Pro Arg Pro Leu Leu Ser Pro Ala Val Pro Gln Lys Trp Pro Ser Pro
        275                 280                 285

Leu Gly Asp Pro Glu Asp Pro Ser Thr Gly Glu Gly Ala Arg Ile
        290                 295                 300

His Thr Leu Leu Lys Asp Leu Gln Arg Gln Pro Ala Glu Ala Arg Gly
305                 310                 315                 320

Leu Ser Asp Leu Glu Leu Asp Ser Met Ala Glu Leu Met Ala Gly Leu
                325                 330                 335

Met Gln Gly Met Asp His Arg Gly Ala Leu Gly Gly Pro Gly Lys Ala
            340                 345                 350

Ala Leu Gly Glu Ser Gly Glu Gln Ala Asp Gly Pro Lys Ala Ala Leu
        355                 360                 365

Arg Gly Glu Ser Phe Pro Asp Asp Gly Val Gln Asp Asp Asp Arg
        370                 375                 380

Leu Tyr Gln Glu Val His Arg Leu Ser Ala Thr Leu Gly Gly Leu Leu
385                 390                 395                 400

Gln Asp His Gly Ser Arg Leu Ser Pro Gly Ala Leu Pro Phe Ala Lys
                405                 410                 415

Pro Leu Lys Met Glu Arg Lys Lys Ser Glu Arg Pro Glu Ala Ser Leu
            420                 425                 430

Ser Ser Glu Glu Glu Thr Ala Gly Val Glu Asn Val Lys Ser Gln Thr
```

-continued

```
              435                 440                 445
Tyr Ser Lys Asp Leu Leu Gly Gln Gln Pro His Ser Glu Pro Gly Ala
            450                 455                 460
Gly Ala Phe Gly Glu Leu Gln Asn Gln Met Pro Gly Pro Ser Glu Glu
465                 470                 475                 480
Glu Gln Ser Leu Pro Ala Gly Ala Gln Glu Ala Leu Gly Asp Gly Leu
                485                 490                 495
Gln Leu Glu Val Lys Pro Ser Glu Glu Ala Arg Cys Tyr Ile Val
            500                 505                 510
Thr Asp Arg Asp Pro Leu Arg Pro Glu Glu Gly Arg Gln Leu Val Glu
            515                 520                 525
Asp Val Ala Arg Leu Leu Gln Met Pro Ser Ser Thr Phe Ala Asp Val
            530                 535                 540
Glu Val Leu Gly Pro Ala Val Thr Phe Lys Val Gly Ala Asn Val Gln
545                 550                 555                 560
Asn Val Thr Thr Ala Asp Val Glu Lys Ala Thr Val Asp Asn Lys Asp
                565                 570                 575
Lys Leu Glu Glu Thr Ser Gly Leu Lys Ile Leu Gln Thr Gly Val Gly
            580                 585                 590
Ser Lys Ser Lys Leu Lys Phe Leu Pro Pro Gln Ala Glu Gln Glu Asp
            595                 600                 605
Ser Thr Lys Phe Ile Ala Leu Thr Leu Val Ser Leu Ala Cys Ile Leu
            610                 615                 620
Gly Val Leu Leu Ala Ser Gly Leu Ile Tyr Cys Leu Arg His Ser Ser
625                 630                 635                 640
Gln His Arg Leu Lys Glu Lys Leu Ser Gly Leu Gly Arg Asp Pro Gly
                645                 650                 655
Ala Asp Ala Thr Ala Ala Tyr Gln Glu Leu Cys Arg Gln Arg Met Ala
            660                 665                 670
Thr Arg Pro Pro Asp Arg Pro Glu Gly Pro His Thr Ser Arg Ile Ser
            675                 680                 685
Ser Val Ser Ser Gln Phe Ser Asp Gly Pro Met Pro Ser Pro Ser Ala
            690                 695                 700
Arg Ser Ser Ala Ser Ser Trp Ser Glu Glu Pro Val Gln Ser Asn Met
705                 710                 715                 720
Asp Ile Ser Thr Gly His Met Ile Leu Ser Tyr Met Glu Asp His Leu
                725                 730                 735
Lys Asn Lys Asn Arg Leu Glu Lys Glu Trp Glu Ala Leu Cys Ala Tyr
                740                 745                 750
Gln Ala Glu Pro Asn Ser Ser Leu Val Ala Gln Lys Glu Glu Asn Val
            755                 760                 765
Pro Lys Asn Arg Ser Leu Ala Val Leu Thr Tyr Asp His Ser Arg Val
            770                 775                 780
Leu Leu Lys Ala Glu Asn Ser His Ser His Ser Asp Tyr Ile Asn Ala
785                 790                 795                 800
Ser Pro Ile Met Asp His Asp Pro Arg Asn Pro Ala Tyr Ile Ala Thr
                805                 810                 815
Gln Gly Pro Leu Pro Ala Thr Val Ala Asp Phe Trp Gln Met Val Trp
            820                 825                 830
Glu Ser Gly Cys Val Val Ile Val Met Leu Thr Pro Leu Thr Glu Asn
            835                 840                 845
Gly Val Arg Gln Cys Tyr His Tyr Trp Pro Asp Glu Gly Ser Asn Leu
            850                 855                 860
```

```
Tyr His Ile Tyr Glu Val Asn Leu Val Ser Glu His Ile Trp Cys Glu
865                 870                 875                 880

Asp Phe Leu Val Arg Ser Phe Tyr Leu Lys Asn Leu Gln Thr Asn Glu
            885                 890                 895

Thr Arg Thr Val Thr Gln Phe His Phe Leu Ser Trp Tyr Asp Arg Gly
            900                 905                 910

Val Pro Ser Ser Ser Arg Ser Leu Leu Asp Phe Arg Arg Lys Val Asn
            915                 920                 925

Lys Cys Tyr Arg Gly Arg Ser Cys Pro Ile Ile Val His Cys Ser Asp
930                 935                 940

Gly Ala Gly Arg Ser Gly Thr Tyr Val Leu Ile Asp Met Val Leu Asn
945                 950                 955                 960

Lys Met Ala Lys Gly Ala Lys Glu Ile Asp Ile Ala Ala Thr Leu Glu
                965                 970                 975

His Leu Arg Asp Gln Arg Pro Gly Met Val Gln Thr Lys Glu Gln Phe
            980                 985                 990

Glu Phe Ala Leu Thr Ala Val Ala Glu Glu Val Asn Ala Ile Leu Lys
            995                 1000                1005

Ala Leu Pro Gln
   1010
```

(2) INFORMATION FOR SEQ ID NO: 17:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: Other (vii) IMMEDIATE SOURCE:
        (B) CLONE: ZC11653

(xi) SEQUENCE DESCRIPTION: SEQ ID NO: 17:

CGGAATTCCT CTGTGGTCCA TGCCTTGC                                    28

(2) INFORMATION FOR SEQ ID NO: 18:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 18:

GCGCCATGAA CTTGGTGGAG TCTTCTTGCT CCGCCTGA                          38

(2) INFORMATION FOR SEQ ID NO: 19:

(i) SEQUENCE CHARACTERISTICS:
        (A) LENGTH: 38 base pairs
        (B) TYPE: nucleic acid
        (C) STRANDEDNESS: single
        (D) TOPOLOGY: linear (ii) MOLECULE TYPE: cDNA (xi) SEQUENCE DESCRIPTION: SEQ ID NO: 19:

AGCTGCCTCC TCCCTCTGTC CCACTCCTGT CTGCAAGA                          38

(2) INFORMATION FOR SEQ ID NO: 20:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA

PTION: SEQ ID NO: 20:

30

(2) INFORMATION FOR SEQ ID NO: 21:

(i) SEQUENCE CHARACTERISTICS:
        (A) LENGTH: 2464 base pairs
        (B) TYPE: nucleic acid
        (C) STRANDEDNESS: double
        (D) TOPOLOGY: linear (ii) MOLECULE TYPE: cDNA (A) NAME/KEY: Coding Sequence
                      55
        (D) OTHER INFORMATION:

(xi) SEQUENCE DESCRIPTION: SEQ ID NO: 21:

```
T CAC ACG TCT GTG CTG ACC TAC CCT CCC GGG CCC CGG ACC CAG CTC CAC      49
  His Thr Ser Val Leu Thr Tyr Pro Pro Gly Pro Arg Thr Gln Leu His
  1               5                  10                  15

GAG GAC CTC CTG CCA CGG ACC CTC GGC CAG CTC CAG CCA GAT GAG CTC        97
Glu Asp Leu Leu Pro Arg Thr Leu Gly Gln Leu Gln Pro Asp Glu Leu
                20                  25                  30

AGC CCT AAG GTG GAC AGT GGT GTG GAC AGA CAC CAT CTG ATG GCG GCC       145
Ser Pro Lys Val Asp Ser Gly Val Asp Arg His His Leu Met Ala Ala
            35                  40                  45

CTC AGT GCC TAT GCT GCC CAG AGG CCC CCA GCT CCC CCC GGG GAG GGC       193
Leu Ser Ala Tyr Ala Ala Gln Arg Pro Pro Ala Pro Pro Gly Glu Gly
        50                  55                  60

AGC CTG GAG CCA CAG TAC CTT CTG CGT GCA CCC TCA AGA ATG CCC AGG       241
Ser Leu Glu Pro Gln Tyr Leu Leu Arg Ala Pro Ser Arg Met Pro Arg
65                  70                  75                  80

CCT TTG CTG GCA CCA GCC GCC CCC CAG AAG TGG CCT TCA CCT CTG GGA       289
Pro Leu Leu Ala Pro Ala Ala Pro Gln Lys Trp Pro Ser Pro Leu Gly
                85                  90                  95

GAT TCC GAA GAC CCC TCT AGC ACA GGC GAT GGA GCA CGG ATT CAT ACC       337
Asp Ser Glu Asp Pro Ser Ser Thr Gly Asp Gly Ala Arg Ile His Thr
            100                 105                 110

CTC CTG AAG GAC CTG CAG AGG CAG CCG GCT GAG GTG AGG GGC CTG AGT       385
Leu Leu Lys Asp Leu Gln Arg Gln Pro Ala Glu Val Arg Gly Leu Ser
        115                 120                 125

GGC CTG GAG CTG GAC GGC ATG GCT GAG CTG ATG GCT GGC CTG ATG CAA       433
Gly Leu Glu Leu Asp Gly Met Ala Glu Leu Met Ala Gly Leu Met Gln
    130                 135                 140

GGC GTG GAC CAT GGA GTA GCT CGA GGC AGC CCT GGG AGA GCG GCC CTG       481
Gly Val Asp His Gly Val Ala Arg Gly Ser Pro Gly Arg Ala Ala Leu
145                 150                 155                 160

GGA GAG TCT GGA GAA CAG GCG GAT GGC CCC AAG GCC ACC CTC CGT GGA       529
Gly Glu Ser Gly Glu Gln Ala Asp Gly Pro Lys Ala Thr Leu Arg Gly
                165                 170                 175

GAC AGC TTT CCA GAT GAC GGA GTG CAG GAC GAC GAT GAT AGA CTT TAC       577
Asp Ser Phe Pro Asp Asp Gly Val Gln Asp Asp Asp Asp Arg Leu Tyr
```

|     |     |     |     |     |     |     |     |     |     |     |     |     |     |     |      |
| --- | --- | --- | --- | --- | --- | --- | --- | --- | --- | --- | --- | --- | --- | --- | ---- |
|     |     |     | 180 |     |     |     | 185 |     |     |     | 190 |     |     |     |      |
| CAA | GAG | GTC | CAT | CGT | CTG | AGT | GCC | ACA | CTC | GGG | GGC | CTC | CTG | CAG | GAC  | 625
| Gln | Glu | Val | His | Arg | Leu | Ser | Ala | Thr | Leu | Gly | Gly | Leu | Leu | Gln | Asp  |
|     |     | 195 |     |     |     | 200 |     |     |     | 205 |     |     |     |     |      |
| CAC | GGG | TCT | CGA | CTC | TTA | CCT | GGA | GCC | CTC | CCC | TTT | GCA | AGG | CCC | CTC  | 673
| His | Gly | Ser | Arg | Leu | Leu | Pro | Gly | Ala | Leu | Pro | Phe | Ala | Arg | Pro | Leu  |
|     |     | 210 |     |     |     | 215 |     |     |     | 220 |     |     |     |     |      |
| GAC | ATG | GAG | AGG | AAG | AAG | TCC | GAG | CAC | CCT | GAG | TCT | TCC | CTG | TCT | TCA  | 721
| Asp | Met | Glu | Arg | Lys | Lys | Ser | Glu | His | Pro | Glu | Ser | Ser | Leu | Ser | Ser  |
| 225 |     |     |     | 230 |     |     |     | 235 |     |     |     | 240 |     |     |      |
| GAA | GAG | GAG | ACT | GCC | GGA | GTG | GAG | AAC | GTC | AAG | AGC | CAG | ACG | TAT | TCC  | 769
| Glu | Glu | Glu | Thr | Ala | Gly | Val | Glu | Asn | Val | Lys | Ser | Gln | Thr | Tyr | Ser  |
|     |     |     | 245 |     |     |     | 250 |     |     |     | 255 |     |     |     |      |
| AAA | GAT | CTG | CTG | GGG | CGG | CAG | CCG | CAT | TCG | GAG | CCC | GGG | GCC | GCT | GCG  | 817
| Lys | Asp | Leu | Leu | Gly | Arg | Gln | Pro | His | Ser | Glu | Pro | Gly | Ala | Ala | Ala  |
|     |     |     | 260 |     |     |     | 265 |     |     |     | 270 |     |     |     |      |
| TTT | GGG | GAG | CTC | CAA | AAC | CAG | ATG | CCT | GGG | CCC | TCG | AAG | GAG | GAG | CAG  | 865
| Phe | Gly | Glu | Leu | Gln | Asn | Gln | Met | Pro | Gly | Pro | Ser | Lys | Glu | Glu | Gln  |
|     |     | 275 |     |     |     | 280 |     |     |     | 285 |     |     |     |     |      |
| AGC | CTT | CCA | GCG | GGT | GCT | CAG | GAG | GCC | CTC | AGC | GAC | GGC | CTG | CAA | TTG  | 913
| Ser | Leu | Pro | Ala | Gly | Ala | Gln | Glu | Ala | Leu | Ser | Asp | Gly | Leu | Gln | Leu  |
|     | 290 |     |     |     | 295 |     |     |     | 300 |     |     |     |     |     |      |
| GAG | GTC | CAG | CCT | TCC | GAG | GAA | GAG | GCG | CGG | GGC | TAC | ATC | GTG | ACA | GAC  | 961
| Glu | Val | Gln | Pro | Ser | Glu | Glu | Glu | Ala | Arg | Gly | Tyr | Ile | Val | Thr | Asp  |
| 305 |     |     |     | 310 |     |     |     | 315 |     |     |     | 320 |     |     |      |
| GGA | GAC | CCC | CTG | CGC | CCC | GAG | GAA | GGA | AGG | CGG | CTG | GTG | GAG | GAC | GTC  | 1009
| Gly | Asp | Pro | Leu | Arg | Pro | Glu | Glu | Gly | Arg | Arg | Leu | Val | Glu | Asp | Val  |
|     |     |     | 325 |     |     |     | 330 |     |     |     | 335 |     |     |     |      |
| GCC | CGC | CTC | CTG | CAG | GTG | CCC | AGC | AGC | GCG | TTC | GCT | GAC | GTG | GAG | GTT  | 1057
| Ala | Arg | Leu | Leu | Gln | Val | Pro | Ser | Ser | Ala | Phe | Ala | Asp | Val | Glu | Val  |
|     |     |     | 340 |     |     |     | 345 |     |     |     | 350 |     |     |     |      |
| CTC | GGA | CCA | GCA | GTG | ACC | TTC | AAA | GTG | AGC | GCC | AAT | GTC | CAA | AAC | GTG  | 1105
| Leu | Gly | Pro | Ala | Val | Thr | Phe | Lys | Val | Ser | Ala | Asn | Val | Gln | Asn | Val  |
|     |     |     | 355 |     |     |     | 360 |     |     |     | 365 |     |     |     |      |
| ACC | ACT | GAG | GAT | GTG | GAG | AAG | GCC | ACA | GTT | GAC | AAC | AAA | GAC | AAA | CTG  | 1153
| Thr | Thr | Glu | Asp | Val | Glu | Lys | Ala | Thr | Val | Asp | Asn | Lys | Asp | Lys | Leu  |
|     | 370 |     |     |     | 375 |     |     |     | 380 |     |     |     |     |     |      |
| GAG | GAA | ACC | TCT | GGA | CTG | AAA | ATT | CTT | CAA | ACC | GGA | GTC | GGG | TCG | AAA  | 1201
| Glu | Glu | Thr | Ser | Gly | Leu | Lys | Ile | Leu | Gln | Thr | Gly | Val | Gly | Ser | Lys  |
| 385 |     |     |     | 390 |     |     |     | 395 |     |     |     | 400 |     |     |      |
| AGC | AAA | CTC | AAG | TTC | CTG | CCT | CCT | CAG | GCG | GAG | CAA | GAA | GAC | TCC | ACC  | 1249
| Ser | Lys | Leu | Lys | Phe | Leu | Pro | Pro | Gln | Ala | Glu | Gln | Glu | Asp | Ser | Thr  |
|     |     |     | 405 |     |     |     | 410 |     |     |     | 415 |     |     |     |      |
| AAG | TTC | ATC | GCG | CTC | ACC | CTG | GTC | TCC | CTC | GCC | TGC | ATC | CTG | GGC | GTC  | 1297
| Lys | Phe | Ile | Ala | Leu | Thr | Leu | Val | Ser | Leu | Ala | Cys | Ile | Leu | Gly | Val  |
|     |     |     | 420 |     |     |     | 425 |     |     |     | 430 |     |     |     |      |
| CTC | CTG | GCC | TCT | GGC | CTC | ATC | TAC | TGC | CTC | CGC | CAT | AGC | TCT | CAG | CAC  | 1345
| Leu | Leu | Ala | Ser | Gly | Leu | Ile | Tyr | Cys | Leu | Arg | His | Ser | Ser | Gln | His  |
|     |     |     | 435 |     |     |     | 440 |     |     |     | 445 |     |     |     |      |
| AGG | CTG | AAG | GAG | AAG | CTC | TCG | GGA | CTA | GGG | GGC | GAC | CCA | GGT | GCA | GAT  | 1393
| Arg | Leu | Lys | Glu | Lys | Leu | Ser | Gly | Leu | Gly | Gly | Asp | Pro | Gly | Ala | Asp  |
|     |     | 450 |     |     |     | 455 |     |     |     | 460 |     |     |     |     |      |
| GCC | ACT | GCC | GCC | TAC | CAG | GAG | CTG | TGC | CGC | CAG | CGT | ATG | GCC | ACG | CGG  | 1441
| Ala | Thr | Ala | Ala | Tyr | Gln | Glu | Leu | Cys | Arg | Gln | Arg | Met | Ala | Thr | Arg  |
| 465 |     |     |     | 470 |     |     |     | 475 |     |     |     | 480 |     |     |      |
| CCA | CCA | GAC | CGA | CCT | GAG | GGC | CCG | CAC | ACG | TCA | CGC | ATC | AGC | AGC | GTC  | 1489
| Pro | Pro | Asp | Arg | Pro | Glu | Gly | Pro | His | Thr | Ser | Arg | Ile | Ser | Ser | Val  |
|     |     |     | 485 |     |     |     | 490 |     |     |     | 495 |     |     |     |      |
| TCA | TCC | CAG | TTC | AGC | GAC | GGG | CCG | ATC | CCC | AGC | CCC | TCC | GCA | CGC | AGC  | 1537

```
                Ser Ser Gln Phe Ser Asp Gly Pro Ile Pro Ser Pro Ser Ala Arg Ser
                            500                 505                 510

AGC GCC TCA TCC TGG TCC GAG GAG CCT GTG CAG TCC AAC ATG GAC ATC              1585
Ser Ala Ser Ser Trp Ser Glu Glu Pro Val Gln Ser Asn Met Asp Ile
            515                 520                 525

TCC ACC GGC CAC ATG ATC CTG TCC TAC ATG GAG GAC CAC CTG AAG AAC              1633
Ser Thr Gly His Met Ile Leu Ser Tyr Met Glu Asp His Leu Lys Asn
        530                 535                 540

AAG AAC CGG CTG GAG AAG GAG TGG GAA GCG CTG TGC GCC TAC CAG GCG              1681
Lys Asn Arg Leu Glu Lys Glu Trp Glu Ala Leu Cys Ala Tyr Gln Ala
545                 550                 555                 560

GAG CCC AAC AGC TCG TTC GTG GCC CAG AGG GAG GAG AAC GTG CCC AAG              1729
Glu Pro Asn Ser Ser Phe Val Ala Gln Arg Glu Glu Asn Val Pro Lys
                565                 570                 575

AAC CGC TCC CTG GCC GTG CTG ACC TAT GAC CAC TCC CGG GTC CTG CTG              1777
Asn Arg Ser Leu Ala Val Leu Thr Tyr Asp His Ser Arg Val Leu Leu
            580                 585                 590

AAG GCG GAG AAC AGC CAC AGC CAC TCA GAC TAC ATC AAC GCT AGC CCC              1825
Lys Ala Glu Asn Ser His Ser His Ser Asp Tyr Ile Asn Ala Ser Pro
        595                 600                 605

ATC ATG GAT CAC GAC CCG AGG AAC CCC GCG TAC ATC GCC ACC CAG GGA              1873
Ile Met Asp His Asp Pro Arg Asn Pro Ala Tyr Ile Ala Thr Gln Gly
610                 615                 620

CCG CTG CCC GCC ACC GTG GCT GAC TTT TGG CAG ATG GTG TGG GAG AGC              1921
Pro Leu Pro Ala Thr Val Ala Asp Phe Trp Gln Met Val Trp Glu Ser
625                 630                 635                 640

GGC TGC GTG GTG ATC GTC ATG CTG ACA CCC CTC GCG GAG AAC GGC GTC              1969
Gly Cys Val Val Ile Val Met Leu Thr Pro Leu Ala Glu Asn Gly Val
                645                 650                 655

CGG CAG TGC TAC CAC TAC TGG CCG GAT GAA GGC TCC AAT CTC TAC CAC              2017
Arg Gln Cys Tyr His Tyr Trp Pro Asp Glu Gly Ser Asn Leu Tyr His
            660                 665                 670

ATC TAT GAG GTG AAC CTG GTC TCC GAG CAC ATC TGG TGT GAG GAC TTC              2065
Ile Tyr Glu Val Asn Leu Val Ser Glu His Ile Trp Cys Glu Asp Phe
        675                 680                 685

CTG GTG AGG AGC TTC TAT CTG AAG AAC CTG CAG ACC AAC GAG ACG CGC              2113
Leu Val Arg Ser Phe Tyr Leu Lys Asn Leu Gln Thr Asn Glu Thr Arg
690                 695                 700

ACC GTG ACG CAG TTC CAC TTC CTG AGT TGG TAT GAC CGA GGA GTC CCT              2161
Thr Val Thr Gln Phe His Phe Leu Ser Trp Tyr Asp Arg Gly Val Pro
705                 710                 715                 720

TCC TCC TCA AGG TCC CTC CTG GAC TTC CGC AGA AAA GTA AAC AAG TGC              2209
Ser Ser Ser Arg Ser Leu Leu Asp Phe Arg Arg Lys Val Asn Lys Cys
                725                 730                 735

TAC AGG GGC CGT TCT TGT CCA ATA ATT GTT CAT TGC AGT GAC GGT GCA              2257
Tyr Arg Gly Arg Ser Cys Pro Ile Ile Val His Cys Ser Asp Gly Ala
            740                 745                 750

GGC CGG AGC GGC ACC TAC GTC CTG ATC GAC ATG GTT CTC AAC AAG ATC              2305
Gly Arg Ser Gly Thr Tyr Val Leu Ile Asp Met Val Leu Asn Lys Met
        755                 760                 765

GCC AAA GGT GCT AAA GAG ATT GAT ATC GCA GCG ACC CTG GAG CAC TTG              2353
Ala Lys Gly Ala Lys Glu Ile Asp Ile Ala Ala Thr Leu Glu His Leu
770                 775                 780

AGG GAC CAG AGA CCC GGC ATG GTC CAG ACG AAG GAG CAG TTT GAG TTC              2401
Arg Asp Gln Arg Pro Gly Met Val Gln Thr Lys Glu Gln Phe Glu Phe
785                 790                 795                 800

GCG CTG ACA GCC GTG GCT GAG GAG GTG AAC GCC ATC CTC AAG GCC CTG              2449
Ala Leu Thr Ala Val Ala Glu Glu Val Asn Ala Ile Leu Lys Ala Leu
                805                 810                 815
```

```
CCC CAG TGAGAATTC                                              2464
Pro Gln
```

(2) INFORMATION FOR SEQ ID NO: 22:

(i) SEQUENCE CHARACTERISTICS:
        (A) LENGTH: 818 amino acids
        (B) TYPE: amino acid
        (C) STRANDEDNESS: single
        (D) TOPOLOGY: linear (ii) MOLECULE TYPE: protein (v) FRAGMENT TYPE: internal (xi) SEQUENCE DESCRIPTION: SEQ ID NO: 22:

```
His Thr Ser Val Leu Thr Tyr Pro Pro Gly Pro Arg Thr Gln Leu His
 1               5                  10                  15

Glu Asp Leu Leu Pro Arg Thr Leu Gly Gln Leu Gln Pro Asp Glu Leu
                20                  25                  30

Ser Pro Lys Val Asp Ser Gly Val Asp Arg His His Leu Met Ala Ala
            35                  40                  45

Leu Ser Ala Tyr Ala Ala Gln Arg Pro Pro Ala Pro Pro Gly Glu Gly
        50                  55                  60

Ser Leu Glu Pro Gln Tyr Leu Leu Arg Ala Pro Ser Arg Met Pro Arg
65                  70                  75                  80

Pro Leu Leu Ala Pro Ala Ala Pro Gln Lys Trp Pro Ser Pro Leu Gly
                85                  90                  95

Asp Ser Glu Asp Pro Ser Ser Thr Gly Asp Gly Ala Arg Ile His Thr
               100                 105                 110

Leu Leu Lys Asp Leu Gln Arg Gln Pro Ala Glu Val Arg Gly Leu Ser
           115                 120                 125

Gly Leu Glu Leu Asp Gly Met Ala Glu Leu Met Ala Gly Leu Met Gln
       130                 135                 140

Gly Val Asp His Gly Val Ala Arg Gly Ser Pro Gly Arg Ala Ala Leu
145                 150                 155                 160

Gly Glu Ser Gly Glu Gln Ala Asp Gly Pro Lys Ala Thr Leu Arg Gly
               165                 170                 175

Asp Ser Phe Pro Asp Asp Gly Val Gln Asp Asp Asp Arg Leu Tyr
           180                 185                 190

Gln Glu Val His Arg Leu Ser Ala Thr Leu Gly Gly Leu Leu Gln Asp
       195                 200                 205

His Gly Ser Arg Leu Leu Pro Gly Ala Leu Pro Phe Ala Arg Pro Leu
   210                 215                 220

Asp Met Glu Arg Lys Lys Ser Glu His Pro Glu Ser Ser Leu Ser Ser
225                 230                 235                 240

Glu Glu Glu Thr Ala Gly Val Glu Asn Val Lys Ser Gln Thr Tyr Ser
               245                 250                 255

Lys Asp Leu Leu Gly Arg Gln Pro His Ser Glu Pro Gly Ala Ala Ala
           260                 265                 270

Phe Gly Glu Leu Gln Asn Gln Met Pro Gly Pro Ser Lys Glu Glu Gln
       275                 280                 285

Ser Leu Pro Ala Gly Ala Gln Glu Ala Leu Ser Asp Gly Leu Gln Leu
   290                 295                 300

Glu Val Gln Pro Ser Glu Glu Ala Arg Gly Tyr Ile Val Thr Asp
305                 310                 315                 320

Gly Asp Pro Leu Arg Pro Glu Glu Gly Arg Arg Leu Val Glu Asp Val
```

-continued

```
                325                 330                 335
Ala Arg Leu Leu Gln Val Pro Ser Ser Ala Phe Ala Asp Val Glu Val
                340                 345                 350
Leu Gly Pro Ala Val Thr Phe Lys Val Ser Ala Asn Val Gln Asn Val
                355                 360                 365
Thr Thr Glu Asp Val Glu Lys Ala Thr Val Asp Asn Lys Asp Lys Leu
            370                 375                 380
Glu Glu Thr Ser Gly Leu Lys Ile Leu Gln Thr Gly Val Gly Ser Lys
385                 390                 395                 400
Ser Lys Leu Lys Phe Leu Pro Pro Gln Ala Glu Gln Glu Asp Ser Thr
                    405                 410                 415
Lys Phe Ile Ala Leu Thr Leu Val Ser Leu Ala Cys Ile Leu Gly Val
                420                 425                 430
Leu Leu Ala Ser Gly Leu Ile Tyr Cys Leu Arg His Ser Ser Gln His
                435                 440                 445
Arg Leu Lys Glu Lys Leu Ser Gly Leu Gly Gly Asp Pro Gly Ala Asp
                450                 455                 460
Ala Thr Ala Ala Tyr Gln Glu Leu Cys Arg Gln Arg Met Ala Thr Arg
465                 470                 475                 480
Pro Pro Asp Arg Pro Glu Gly Pro His Thr Ser Arg Ile Ser Ser Val
                    485                 490                 495
Ser Ser Gln Phe Ser Asp Gly Pro Ile Pro Ser Pro Ser Ala Arg Ser
                500                 505                 510
Ser Ala Ser Ser Trp Ser Glu Glu Pro Val Gln Ser Asn Met Asp Ile
                515                 520                 525
Ser Thr Gly His Met Ile Leu Ser Tyr Met Glu Asp His Leu Lys Asn
                530                 535                 540
Lys Asn Arg Leu Glu Lys Glu Trp Glu Ala Leu Cys Ala Tyr Gln Ala
545                 550                 555                 560
Glu Pro Asn Ser Ser Phe Val Ala Gln Arg Glu Glu Asn Val Pro Lys
                    565                 570                 575
Asn Arg Ser Leu Ala Val Leu Thr Tyr Asp His Ser Arg Val Leu Leu
                580                 585                 590
Lys Ala Glu Asn Ser His Ser His Ser Asp Tyr Ile Asn Ala Ser Pro
                595                 600                 605
Ile Met Asp His Asp Pro Arg Asn Pro Ala Tyr Ile Ala Thr Gln Gly
                610                 615                 620
Pro Leu Pro Ala Thr Val Ala Asp Phe Trp Gln Met Val Trp Glu Ser
625                 630                 635                 640
Gly Cys Val Val Ile Val Met Leu Thr Pro Leu Ala Glu Asn Gly Val
                    645                 650                 655
Arg Gln Cys Tyr His Tyr Trp Pro Asp Glu Gly Ser Asn Leu Tyr His
                660                 665                 670
Ile Tyr Glu Val Asn Leu Val Ser Glu His Ile Trp Cys Glu Asp Phe
                675                 680                 685
Leu Val Arg Ser Phe Tyr Leu Lys Asn Leu Gln Thr Asn Glu Thr Arg
                690                 695                 700
Thr Val Thr Gln Phe His Phe Leu Ser Trp Tyr Asp Arg Gly Val Pro
705                 710                 715                 720
Ser Ser Ser Arg Ser Leu Leu Asp Phe Arg Arg Lys Val Asn Lys Cys
                    725                 730                 735
Tyr Arg Gly Arg Ser Cys Pro Ile Ile Val His Cys Ser Asp Gly Ala
                740                 745                 750
```

```
Gly Arg Ser Gly Thr Tyr Val Leu Ile Asp Met Val Leu Asn Lys Met
            755                 760                 765
Ala Lys Gly Ala Lys Glu Ile Asp Ile Ala Ala Thr Leu Glu His Leu
    770                 775                 780
Arg Asp Gln Arg Pro Gly Met Val Gln Thr Lys Glu Gln Phe Glu Phe
785                 790                 795                 800
Ala Leu Thr Ala Val Ala Glu Glu Val Asn Ala Ile Leu Lys Ala Leu
                805                 810                 815
Pro Gln
```

(2) INFORMATION FOR SEQ ID NO: 23:

(i) SEQUENCE CHARACTERISTICS:
        (A) LENGTH: 2736 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 23:

```
CAGGACAGAC CCCGTGCTGA GGGTGACGAC CGCTTCTCCA AGAGCATCCT GACCTATGTG      60
GCCCACACGT CTGTGCTGAC CTACCCTCCC GGGCCCCAGG CCCAGCTCCC CGAGGACCTC     120
CTGCCACGGA CCCTCAGCCA GCTCCAGCCA GACGAGCTCA GCCCTAAGGT GGACAGCAGT     180
GTGGAGAGAC ACCATCTGAT GGCAGCCCTC AGTGCCTATG CTGCCCAGAG GCCCCCAGCT     240
CCCCCTGGGA AGGGCAGCCT GGAGCCGCAG TACCTTCTGC GCGCCCCGTC CAGAATGCCC     300
AGGCCCTTGT TGTCGCCAGC CGTCCCCCAG AAGTGGCCTT CACCTCTGGG AGATCCTGAA     360
GACCCCCCCA GCACAGGGGA AGGAGCACGG ATTCACACTC TCCTGAAGGA CCTGCAGAGG     420
CAGCCGGCTG AGGCGAGGGG CCTGAGTGAC CTGGAGCTGG ACAGCATGGC CGAGCTGATG     480
GCTGGCCTGA TGCAAGGCAT GGACCACAGA GGAGCTCTAG GCGGCCCTGG GAAAGCGGCC     540
CTGGGAGAGT CTGGAGAACA GCGGATGGC CCCAAGGCCG CCCTCCGTGG GGAAAGCTTT     600
CCAGATGACG GAGTTCAGGA CGACGATGAC AGACTTTACC AAGAGGTCCA TCGTCTGAGT     660
GCCACACTCG GGGCCTCCT GCAGGACCAC GGGTCTCGAC TCTCGCCTGG AGCCCTCCCC     720
TTTGCAAAGC CCCTCAAAAT GGAGAGGAAG AAATCCGAGC GCCCTGAGGC TTCCCTGTCT     780
TCAGAAGAGG AGACTGCCGG AGTGGAGAAC GTCAAGAGCC AGACGTATTC CAAAACCTGC     840
TGGGGCAGCA GCCGCATTCG GAGCCCGGGG CAGGCGCGTT TGGGGAGCTC CAAACCAGAT     900
GCCTGGGCCC TCGAGGAGG AGCAGAGCCT TCCAGCGGGT GCTCAGGAGG CCCTCGGCGA     960
CGGCTGCAAT TGGAAGTCAA GCCTTCCGAG GAAGAGGCAC GGTGCTACAT CGTGACAGAC    1020
AGAGACCCCC TGCGCCCCGA GGAAGGAAGG CAGCTGGTGG AGGACGTCGC CGCCTCCTG    1080
CAGATGCCCA GCAGCACATT CGCCGACGTG GAGGTTCTCG ACCAGCAGT GACCTTCAAA    1140
GTGGGCGCCA ATGTCCAGAA CGTGACCACT GCGGATGTGG AGAAGGCCAC AGTTGACAAC    1200
AAAGACAAAC TGGAGGAAAC CTCTGGACTG AAAATTCTTC AAACCGGAGT CGGGTCGAAA    1260
AGCAAACTCA AGTTCCTGCC TCCTCAGGCG GAGCAAGAAG ACTCAACCAA GTTCATCGCG    1320
CTCACCCTGG TCTCCCTCGC CTGCATCCTG GGCGTCCTCC TGGCCTCTGG CCTCATCTAC    1380
TGCCTACGCC ATAGCTCTCA GCACAGGCTG AAGGAGAAGC TCTCGGGACT AGGGCGCGAC    1440
CCAGGTGCAG ATGCCACCGC CGCCTACCAG GAGCTGTGCC GCCAGCGTAT GGCCACGCGG    1500
CCACCAGACC GGCCCGAGGG CCCGCACACA TCCCGCATCA GCAGCGTCTC GTCCCAGTTC    1560
```

```
AGCGACGGGC CGATGCCCAG CCCCTCCGCA CGCAGCAGCG CCTCGTCCTG GTCCGAGGAG    1620

CCCGTGCAGT CCAACATGGA CATCTCCACC GGCCACATGA TCCTGTCCTA CATGGAGGAC    1680

CACCTGAAGA ACAAGAACCG GCTGGAGAAG GAGTGGGAGG CGCTGTGTGC CTACCAGGCG    1740

GAGCCCAACA GCTCACTTGT GGCCCAGAAG GAGGAGAATG TGCCCAAGAA CCGCTCCCTG    1800

GCCGTGCTGA CCTATGACCA CTCCCGGGTC CTACTGAAGG CGGAGAACAG CCACAGCCAC    1860

TCGGACTACA TCAACGCCAG CCCCATCATG GATCACGACC CGAGGAACCC CGCGTACATC    1920

GCCACCCAGG GACCGCTGCC CGCCACCGTG GCCGACTTTT GGCAGATGGT GTGGGAGAGC    1980

GGCTGCGTGG TGATCGTCAT GCTGACACCC CTCACAGAGA ACGGCGTCCG GCAGTGCTAC    2040

CACTACTGGC CAGATGAAGG CTCCAACCTC TACCACATCT ATGAGGTGAA CCTGGTCTCC    2100

GAGCACATCT GGTGCGAGGA CTTTCTGGTG AGGAGCTTCT ATCTGAAGAA CCTGCAGACC    2160

AACGAGACGC GCACCGTGAC CCAGTTCCAC TTCCTGAGTT GGTATGACCG AGGAGTCCCC    2220

TCCTCCTCAA GATCCCTCCT GGACTTCCGC AGAAAAGTAA ACAAGTGCTA CAGGGGCCGT    2280

TCTTGTCCAA TAATTGTTCA TTGCAGTGAC GGTGCAGGCC GGAGCGGCAC CTACGTCCTG    2340

ATCGACATGG TTCTCAACAA GATGGCCAAA GGTGCTAAAG AGATTGATAT CGCAGCAACC    2400

CTGGAGCACT TGAGGGACCA GAGACCCGGC ATGGTCCAGA CGAAGGAGCA GTTTGAGTTC    2460

GCGCTGACAG CCGTGGCTGA AGAGGTGAAT GCCATCCTCA AGGCCCTTCC CCAGTGAGCA    2520

GCGGCCTCGG GGCCTCGGGG GAGCCCCCAC CCCCCGGATG TCGTCAGGAA TCGTGATCTG    2580

ACTTTAATTG TGTGTCTTCT ATTATAACTG CATAGTAATA GGGCCCTTAG CTCTCCAGTA    2640

GTCAGCGCAG TTTAGCAGTT AAGCAGTTAA AATGTGTATT TTTGTTTAAT CCAACAATAA    2700

TAAAGAGAGA TTTGTGGAAA AATCCCAAAA AAAAAA                              2736

(2) INFORMATION FOR SEQ ID NO: 24:

(i) SEQUENCE CHARACTERISTICS:
           (A) LENGTH: 738 base pairs
           (B) TYPE: nucleic acid
           (C) STRANDEDNESS: double
           (D) TOPOLOGY: linear (ii) MOLECULE TYPE: cDNA (xi) SEQUENCE DESCRIPTION: SEQ ID NO: 24:

ACGTGGCAGG ATGACTATAC TCAGTATGTG ATGGACCAGG AACTTGCAGA CCTCCCCAAA      60

ACCTACCTGA GGCATCCTGA AGCGTCCGGC CCAGCCAGGC CCTCAAAACA CAGCATTGGC     120

AGTGAGAGGA GGTACAGTCG GGAGGGCGGC GCTGCCCTGG CCAAGGCCTT CCGACGCCAC     180

CTGCCCTTCC TGGAGGCCCT GTCCCAGGCC CCAGCTTCAG ACGCGCTCGC CAGGACCCGG     240

ATGGCGCAGG ACAGACCCCG TGCTGAGGGT GACGACCGCT TCTCCAAGAG CATCCTGACC     300

TATGTGGCCC ACACGTCTGT GCTGACCTAC CCTCCCGGGC CCAGGCCCA GCTCCCCGAG      360

GACCTCCTGC CACGGACCCT CAGCCAGCTC CAGCCAGACG AGCTCAGCCC TAAGGTGGAC     420

AGCAGTGTGG AGAGACACCA TCTGATGGCA GCCCTCAGTG CCTATGCTGC CCAGAGGCCC     480

CCAGCTCCCC CTGGGAAGGG CAGCCTGGAG CCGCAGTACC TTCTGCGCGC CCCGTCCAGA     540

ATGCCCAGGC CCTTGTTGTC GCCAGCCGTC CCCCAGAAGT GGCCTTCACC TCTGGGAGAT     600

CCTGAAGACC CCCCCAGCAC AGGGGAAGGA GCACGGATTC ACACTCTCCT GAAGGACCTG     660

CAGAGGCAGC CGGCTGAGGC GAGGGGCCTG AGTGACCTGG AGCTGGACAG CATGGCCGAG     720

CTGATGGCTG GCCTGATG                                                   738
```

(2) INFORMATION FOR SEQ ID NO: 25:

(i) SEQUENCE CHARACTERISTICS:
        (A) LENGTH: 932 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 25:

```
GCCGGCAGCT CCCGGGGCGC CTGGGCTGCC TACTCGAGGA GGGCCTCTGC GGAGCGTCCG      60
AGGCCTGTGT GAACGATGGA GTGTTTGGAA GGTGCCAGAA GGTTCCGGCA ATGGACTTTT     120
ACCGCTACGA GGTGTCGCCC GTGGCCCTGC AGCGCCTGCG CGTGGCTTTG CAGAAACTTT     180
CCGGCACAGG TTTCACGTGG CAGGATGACT ATACTCAGTA TGTGATGGAC CAGGAACTTG     240
CAGACCTCCC CAAAACCTAC CTGAGGCATC CTGAAGCGTC CGGCCCAGCC AGGCCCTCAA     300
AACACAGCAT TGGCAGTGAG AGGAGGTACA GTCGGGAGGG CGGCGCTGCC CTGGCCAAGG     360
CCTTCCGACG CCACCTGCCC TTCCTGGAGG CCCTGTCCCA GGCCCCAGCT TCAGACGCGC     420
TCGCCAGGAC CCGGATGGCG CAGGACAGAC CCCGTGCTGA GGGTGACGAC CGCTTCTCCA     480
AGAGCATCCT GACCTATGTG GCCCACACGT CTGTGCTGAC CTACCCTCCC GGGCCCCAGG     540
CCCAGCTCCC CGAGGACCTC CTGCCACGGA CCCTCAGCCA GCTCCAGCCA GACGAGCTCA     600
GCCCTAAGGT GGACAGCAGT GTGGAGAGAC ACCATCTGAT GGCAGCCCTC AGTGCCTATG     660
CTGCCCAGAG GCCCCCAGCT CCCCCTGGGA AGGGCAGCCT GGAGCCGCAG TACCTTCTGC     720
GCGCCCCGTC CAGAATGCCC AGGCCCTTGT TGTCGCCAGC CGTCCCCCAG AAGTGGCCTT     780
CACCTCTGGG AGATCCTGAA GACCCCCCCA GCACAGGGGA AGGAGCACGG ATTCACACTC     840
TCCTGAAGGA CCTGCAGAGG CAGCCGGCTG AGGCGAGGGG CCTGAGTGAC CTGGAGCTGG     900
ACAGCATGGC CGAGCTGATG GCTGGCCTGA TG                                   932
```

(2) INFORMATION FOR SEQ ID NO: 26:

(i) SEQUENCE CHARACTERISTICS:
        (A) LENGTH: 999 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 26:

```
CTGTTGCTGC TACTGCTGCT GCTGCCGCCA CGCGTCCTGC CTGCCGCCCC CTCGTCCGTC      60
CCCCACGGCC GGCAGCTCCC GGGGCGCCTG GGCTGCCTAC TCGAGGAGGG CCTCTGCGGA     120
GCGTCCGAGG CCTGTGTGAA CGATGGAGTG TTTGGAAGGT GCCAGAAGGT TCCGGCAATG     180
GACTTTTACC GCTACGAGGT GTCGCCCGTG GCCCTGCAGC GCCTGCGCGT GGCTTTGCAG     240
AAACTCTCCG GCACAGGTTT CACGTGGCAG GATGACTATA CTCAGTATGT GATGGACCAG     300
GAACTTGCAG ACCTCCCCAA AACCTACCTG AGGCATCCTG AAGCGTCCGG CCCAGCCAGG     360
CCCTCAAAAC ACAGCATTGG CAGTGAGAGG AGGTACAGTC GGGAGGGCGG CGCTGCCCTG     420
GCCAAGGCCT TCCGACGCCA CCTGCCCTTC CTGGAGGCCC TGTCCCAGGC CCCAGCTTCA     480
GACGCGCTCG CCAGGACCCG GATGGCGCAG GACAGACCCC GTGCTGAGGG TGACGACCGC     540
TTCTCCAAGA GCATCCTGAC CTATGTGGCC CACACGTCTG TGCTGACCTA CCCTCCCGGG     600
```

```
CCCCAGGCCC AGCTCCCCGA GGACCTCCTG CCACGGACCC TCAGCCAGCT CCAGCCAGAC        660

GAGCTCAGCC CTAAGGTGGA CAGCAGTGTG GAGAGACACC ATCTGATGGC AGCCCTCAGT        720

GCCTATGCTG CCCAGAGGCC CCCAGCTCCC CCTGGGAAGG GCAGCCTGGA GCCGCAGTAC        780

CTTCTGCGCG CCCCGTCCAG AATGCCCAGG CCCTTGTTGT CGCCAGCCGT CCCCCAGAAG        840

TGGCCTTCAC CTCTGGGAGA TCCTGAAGAC CCCCCAGCA CAGGGGAAGG AGCACGGATT        900

CACACTCTCC TGAAGGACCT GCAGAGGCAG CCGGCTGAGG CGAGGGCCT GAGTGACCTG        960

GAGCTGGACA GCATGGCCGA GCTGATGGCT GGCCTGATG                              999
```

(2) INFORMATION FOR SEQ ID NO: 27:

(i) SEQUENCE CHARACTERISTICS:
        (A) LENGTH: 1011 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 27:

```
GCGCTCCCGC TGCTGTTGCT GCTACTGCTG CTGCTGCCGC CACGCGTCCT GCCTGCCGCC         60

CCCTCGTCCG TCCCCCACGG CCGGCAGCTC CCGGGGCGCC TGGGCTGCCT ACTCGAGGAG        120

GGCCTCTGCG GAGCGTCCGA GGCCTGTGTG AACGATGGAG TGTTTGGAAG GTGCCAGAAG        180

GTTCCGGCAA TGGACTTTTA CCGCTACGAG GTGTCGCCCG TGGCCCTGCA GCGCCTGCGC        240

GTGGCTTTGC AGAAACTCTC CGGCACAGGT TTCACGTGGC AGGATGACTA TACTCAGTAT        300

GTGATGGACC AGGAACTTGC AGACCTCCCC AAAACCTACC TGAGGCATCC TGAAGCGTCC        360

GGCCCAGCCA GGCCCTCAAA ACACAGCATT GGCAGTGAGA GGAGGTACAG TCGGGAGGGC        420

GGCGCTGCCC TGGCCAAGGC CTTCCGACGC CACCTGCCCT TCCTGGAGGC CCTGTCCCAG        480

GCCCCAGCTT CAGACGCGCT CGCCAGGACC CGGATGGCGC AGGACAGACC CCGTGCTGAG        540

GGTGACGACC GCTTCTCCAA GAGCATCCTG ACCTATGTGG CCCACACGTC TGTGCTGACC        600

TACCCTCCCG GGCCCCAGGC CCAGCTCCCC GAGGACCTCC TGCCACGGAC CCTCAGCCAG        660

CTCCAGCCAG ACGAGCTCAG CCCTAAGGTG GACAGCAGTG TGGAGAGACA CCATCTGATG        720

GCAGCCCTCA GTGCCTATGC TGCCCAGAGG CCCCCAGCTC CCCCTGGGAA GGGCAGCCTG        780

GAGCCGCAGT ACCTTCTGCG CGCCCCGTCC AGAATGCCCA GGCCCTTGTT GTCGCCAGCC        840

GTCCCCCAGA AGTGGCCTTC ACCTCTGGGA GATCCTGAAG ACCCCCCCAG CACAGGGGAA        900

GGAGCACGGA TTCACACTCT CCTGAAGGAC CTGCAGAGGC AGCCGGCTGA GGCGAGGGGC        960

CTGAGTGACC TGGAGCTGGA CAGCATGGCC GAGCTGATGG CTGGCCTGAT G               1011
```

(2) INFORMATION FOR SEQ ID NO: 28:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC11654

(xi) SEQUENCE DESCRIPTION: SEQ ID NO: 28:

```
CGGAATTCCT CTGTGGTCCA TGCCTTGC                                           28
```

(2) INFORMATION FOR SEQ ID NO: 29:

(i) SEQUENCE CHARACTERISTICS:
        (A) LENGTH: 30 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (B) CLONE: ZC11197

(xi) SEQUENCE DESCRIPTION: SEQ ID NO: 29:

```
AAATTAATAC GACTCACTAT AGGGAGACCG                                  30
```

(2) INFORMATION FOR SEQ ID NO: 30:

(i) SEQUENCE CHARACTERISTICS:
        (A) LENGTH: 1210 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 30:

```
AGTGCTGCTC ACTCTGGTGG CCCTGGCAGG TGTGGCTGGG CTGCTGGTGG CTCTGGCTGT    60
GGCTCTGTGT GTGCGGCAGC ATGCGCGGCA GCAAGACAAG GAGCGCCTGG CAGCCCTGGG   120
GCCTGAGGGG GCCCATGGTG ACACTACCTT TGAGTACCAG GACCTGTGCC GCCAGCACAT   180
GGCCACGAAG TCCTTGTTCA ACCGGGCAGA GGGTCCACCG GAGCCTTCAC GGGTGAGCAG   240
TGTGTCCTCC CAGTTCAGCG ACGCAGCCCA GGCCAGCCCC AGCTCCCACA GCAGCACCCC   300
GTCCTGGTGC GAGGAGCCGG CCCAAGCCAA CATGGACATC TCCACGGGAC ACATGATTCT   360
GGCATACATG GAGGATCACC TGCGGAACCG GGACCGCCTT GCCAAGGAGT GGCAGGCCCT   420
CTGTGCCTAC CAAGCAGAGC CAAACACCTG TGCCACCGCG CAGGGGGAGG GCAACATCAA   480
AAAGAACCGG CATCCTGACT TCCTGCCCTA TGACCATGCC CGCATAAAAC TGAAGGTGGA   540
GAGCAGCCCT TCTCGGAGCG ATTACATCAA CGCCAGCCCC ATTATTGAGC ATGACCCTCG   600
GATGCCAGCC TACATAGCCA CGCAGGGCCC GCTGTCCCAT ACCATCGCAG ACTTCTGGCA   660
GATGGTGTGG GAGAGCGGCT GCACCGTCAT CGTCATGCTG ACCCCGCTGG TGGAGGATGG   720
TGTCAAGCAG TGTGACCGCT ACTGGCCAGA TGAGGGTGCC TCCCTCTACC ACGTATATGA   780
GGTGAACCTG GTGTCGGAGC ACATCTGGTG CGAGGACTTT CTGGTGCGGA GCTTCTACCT   840
GAAGAACGTG CAGACCCAGG AGACGCGCAC GCTCACGCAG TTCCACTTCC TCAGCTGGCC   900
GGCAGAGGGC ACACCGGCCT CCACGCGGCC CCTGCTGGAC TTCCGCAGGA AGGTGAACAA   960
GTGCTACCGG GGCCGCTCCT GCCCCATCAT CGTGCACTGC AGTGATGGTG CGGGGAGGAC  1020
CGGCACCTAC ATCCTCATCG ACATGGTCCT GAACCGCATG GCAAAAGGAG TGAAGGAGAT  1080
TGACATCGCT GCCACCCTGG AGCATGTCCG TGACCAGCGG CCTGGCCTTG TCCGCTCTAA  1140
GGACCAGTTT GAATTTGCCC TGACAGCCGT GGCGGAGGAA GTGAATGCCA TCCTCAAGGC  1200
CCTGCCCCAG                                                        1210
```

(2) INFORMATION FOR SEQ ID NO: 31:

(i) SEQUENCE CHARACTERISTICS:
        (A) LENGTH: 1263 base pairs
        (B) TYPE: nucleic acid (C) STRANDEDNESS: double
        (D) TOPOLOGY: linear (ii) MOLECULE TYPE: cDNA (xi) SEQUENCE DESCRIPTION: SEQ ID NO: 31:

```
TCACACGTCT GTGCTGACCT ACCCTCCCGG GCCCCGGACC CAGCTCCACG AGGACCTCCT    60

GCCACGGACC CTCGGCCAGC TCCAGCCAGA TGAGCTCAGC CCTAAGGTGG ACAGTGGTGT   120

GGACAGACAC CATCTGATGG CGGCCCTCAG TGCCTATGCT GCCCAGAGGC CCCCAGCTCC   180

CCCCGGGGAG GGCAGCCTGG AGCCACAGTA CCTTCTGCGT GCACCCTCAA GAATGCCCAG   240

GCCTTTGCTG CACCAGCCG CCCCCCAGAA GTGGCCTTCA CCTCTGGGAG ATTCCGAAGA    300

CCCCTCTAGC ACAGGCGATG GAGCACGGAT TCATACCCTC CTGAAGGACC TGCAGAGGCA   360

GCCGGCTGAG GTGAGGGGCC TGAGTGGCCT GGAGCTGGAC GGCATGGCTG AGCTGATGGC   420

TGGCCTGATG CAAGGCGTGG ACCATGGAGT AGCTCGAGGC AGCCCTGGGA GAGCGGCCCT   480

GGGAGAGTCT GGAGAACAGG CGGATGGCCC CAAGGCCACC CTCCGTGGAG ACAGCTTTCC   540

AGATGACGGA GTGCAGGACG ACGATGATAG ACTTTACCAA GAGGTCCATC GTCTGAGTGC   600

CACACTCGGG GGCCTCCTGC AGGACCACGG GTCTCGACTC TTACCTGGAG CCCTCCCCTT   660

TGCAAGGCCC CTCGACATGG AGAGGAAGAA GTCCGAGCAC CCTGAGTCTT CCCTGTCTTC   720

AGAAGAGGAG ACTGCCGGAG TGGAGAACGT CAAGAGCCAG ACGTATTCCA AGATCTGCT    780

GGGGCGGCAG CCGCATTCGG AGCCCGGGGC CGCTGCGTTT GGGGAGCTCC AAAACCAGAT   840

GCCTGGGCCC TCGAAGGAGG AGCAGAGCCT TCCAGCGGGT GCTCAGGAGG CCCTCAGCGA   900

CGGCCTGCAA TTGGAGGTCC AGCCTTCCGA GGAAGAGGCG CGGGGCTACA TCGTGACAGA   960

CGGAGACCCC CTGCGCCCCG AGGAAGGAAG GCGGCTGGTG GAGGACGTCG CCCGCCTCCT  1020

GCAGGTGCCC AGCAGCGCGT TCGCTGACGT GGAGGTTCTC GGACCAGCAG TGACCTTCAA  1080

AGTGAGCGCC AATGTCCAAA ACGTGACCAC TGAGGATGTG GAGAAGGCCA CAGTTGACAA  1140

CAAAGACAAA CTGGAGGAAA CCTCTGGACT GAAAATTCTT CAAACCGGAG TCGGGTCGAA  1200

AAGCAAACTC AAGTTCCTGC CTCCTCAGGC GGAGCAAGAA GACTCCACCA AGTTCATCGC  1260

GCA                                                                1263
```

(2) INFORMATION FOR SEQ ID NO: 32:

(i) SEQUENCE CHARACTERISTICS:
        (A) LENGTH: 758 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 32:

```
GAATTCGGCT TAAGGCGACG GTGGACAACA AAGACAAACT GGAGGAAACC TCTGGACTGA    60

AAATTCTTCA AACCGGAGTC GGGTCGAAAA GCAAACTCAA GTTCCTGCCT CCTCAGGCCG   120

AGCAAGAAGA CTCCACCAAG TTCATCGCGC TCACCCTGGT CTCCCTCGCC TGCATCCTGG   180

GCGTCCTCCT GGCCTCTGGC CTCATCTACT GCCTCCGCCA TAGCTCTCAG CACAGGCTGA   240

AGGAGAAGCT CTCGGGACTA GGGGGCGACC CAGGTGCAGA TGCCACTGCC GCCTACCAGG   300

AGCTGTGCCG CCAGCGTATG GCCACGCGGC CACCAGACCG ACCTGAGGGC CGCACACGT    360

CACGCATCAG CAGCGTCTCA TCCCAGTTCA GCGACGGGCC GATCCCCAGC CCCTCCGCAC   420

GCAGCAGCGC CTCATCCTGG TCCGAGGAGC CTGTGCAGTC CAACATGGAC ATCTCCACCG   480
```

```
GCCACATGAT CCTGTCCTAC ATGGAGGACC ACCTGAAGAA CAAGAACCGG CTGGAGAAAG      540

AGTGGGAAGC GCTGTGCGCC TACCAGGCGG AGCCCAACAG CTCGTTCGTG GCCCAGAGGG      600

AGGAGAACGT GCCCAAGAAC CGCTCCCTGG CCGTGCTGAC CTATGACCAC TCCCGGGTCC      660

TGCTGAAGGC GGAGAACAGC CACAGCCACT CAGACTACAT CAACGCTAGC CCCATCATGG      720

ATCACGACCC GAGGAACCCC GCGTACAAAG CCGAATTC                              758
```

(2) INFORMATION FOR SEQ ID NO: 33:

(i) SEQUENCE CHARACTERISTICS:
        (A) LENGTH: 1150 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 33:

```
AAGCTTCCAC CATGCGCCAT AGCTCTCAGC ACAGGCTGAA AGAGAAGCTC TCGGGACTAG       60

GGGGCGACCC AGGTGCAGAT GCCACTGCCG CCTACCAGGA GCTGCGCCGC CAGCGTATGG      120

CCACGCGGCC ACCAGACCGA CCTGAGGGCC CGCACACGTC ACGCATCAGC AGCGTCTCAT      180

CCCAGTTCAG CGACGGGCCG ATCCCCAGCC CCTCCGCACG CAGCAGCGCC TCATCCTGGT      240

CCGAGGAGCC TGTGCAGTCC AACATGGACA TCTCCACCGG CCACATGATC CTGTCCTACA      300

TGGAGGACCA CCTGAAGAAC AAGAACCGGC TGGAGAAGGA GTGGGAAGCG CTGTGCGCCT      360

ACCAGGCGGA GCCCAACAGC TCGTTCGTGG CCCAGAGGGA GGAGAACGTG CCCAAGAACC      420

GCTCCCTGGC CGTGCTGACC TATGACCACT CCCGGGTCCT GCTGAAGGCG GAGAACAGCC      480

ACAGCCACTC AGACTACATC AACGCTAGCC CCATCATGGA TCACGACCCG AGGAACCCCG      540

CGTACATCGC CACCCAGGGA CCGCTGCCCG CCACCGTGGC TGACCTTTGG CAGATGGTGT      600

GGGAGAGCGG CTGCGTGGTG ATCGTCATGC TGACACCCCT CGCGGAGAAC GGCGTCCGGC      660

AGTGCTACCA CTACTGGCCG GATGAAGGCT CCAATCTCTA CCACATCTAT GAGGTGAACC      720

TGGTCTCCGA GCACATCTGG TGTGAGGACT TCCTGGTGAG GAGCTTCTAT CTGAAGAACC      780

TGCAGACCAA CGAGACGCGC ACCGTGACGC AGTTCCACTT CCTGAGTTGG TATGACCGAG      840

GAGTCCCTTC CTCCTCAAGG TCCCTCCTGG ACTTCCGCAG AAAAGTAAAC AAGTGCTACA      900

GGGGCCGTTC TTGTCCAATA ATTGTTCATT GCAGTGACGG TGCAGGCCGG AGCGGCACCT      960

ACGTCCTGAT CGACATGGTT CTCAACAAGA CGGCCAAAGG TGCTAAAGAG ATTGATATCG     1020

CAGCGACCCT GGAGCACTTG AGGGACCAGA GACCCGGCAT GTCCAGACGA AGGAGCAGTT     1080

TGAGTTCGCG CTGACAGCCG TGGCTGAGGA GGTGAACGCC ATCCTCAAGG CCCTGCCCCA     1140

GTGAGAATTC                                                            1150
```

(2) INFORMATION FOR SEQ ID NO: 34:

(i) SEQUENCE CHARACTERISTICS:
        (A) LENGTH: 2328 base pairs
        (B) TYPE: nucleic acid
        (C) STRANDEDNESS: double
        (D) TOPOLOGY: linear (ii) MOLECULE TYPE: cDNA (xi) SEQUENCE DESCRIPTION: SEQ ID NO: 34:

```
GAATTCGGCT TGAGGAACCC CGCGTACATC GCCACCCAGG GACCGCTGCC CGCCACCGTG       60
```

-continued

```
GCTGACTTTT GGCAGATGGT GTGGGAGAGC GGCTGCGTGG TGATCGTCAT GCAGACACCC      120
CTCGCGGAGA ACGGCGTCCG GCAGTGCTAC CACTACTGGC CGGATGAAGG CTCCAATCTC      180
TACCACATCT ATGAGGTGAA CCTGGTCTCC GAGCACATCT GGTGTGAGGA CTTCCTGGTG      240
AGGAGCTTCT ATCTGAAGAA CCTGCAGACC AACGAGACGC GCACCGTGAC GCAGTTCCAC      300
TTCCTGAGTT GGTTTGACCG AGGAGTCCCT TCCTCCTCAA GGTCCCTCCT GGACTTCCGC      360
AGAAAAGTAA ACAAGTGCTA CAGGGGCCGT TCTTGTCCAA TAATTGTTCA TTGCAGTGAC      420
GGTGCAGGCC GGAGCGGCAC CTACGTCCTG ATCGACATGG TTCTCAACAA GATGGCCAAA      480
GGTGCTAAAG AGATTGATAT CGCAGCGACC CTGGAGCACT TGAGGGACCA GAGACCCGGC      540
ATGGTCCAGA CGAAGGAGTA GTTTGAGTTC GCGCTGACAG CCGTGGCTGA GGAGGTGAAC      600
GCCATCCTCA AGGCCCTTCC CCAGTGAGCG GCAGCCTCAG GGGCCTCAGG GGAGCCCCCA      660
CCCCACGGAT GTTGTCAGGA ATCATGATCT GACTTTAATT GTGTGTCTTC TATTATAACT      720
GCATAGTAAT AGGGCCCTTA GCTCTCCCGT AGTCAGCGCA GTTTAGCAGT TAAAAGTGTA      780
TTTTTGTTTA ATCAAACAAT AATAAAGAGA GATTTGTGGA AAAATCCAGT TACGGGTGGA      840
GGGGAATCGG TTCATCAATT TTCACTTGCT TAAAAAAAAT ACTTTTTCTT AAAGCACCCG      900
TTCACCTTCT TGGTTGAAGT TGTGTTAACA ATGCAGTAGC CAGCACGTTC GAGGCGGTTT      960
CCAGGAAGAG TGTGCTTGTC ATCTGCCACT TTCGGGAGGG TGGATCCACT GTGCAGGAGT     1020
GGCCGGGGAA GCTGGCAGCA CTCAGTGAGG CCGCCCGGCA CACAAGGCAC GTTTGGCATT     1080
TCTCTTTGAG AGAGTTTATC ATTGGGAGAA GCCGCGGGGA CAGAACTGAA CGTCCTGCAG     1140
CTTCGGGGCA AGTGAGACAA TCACAGCTCC TCGCTGCGTC TCCATCAACA CTGCGCCGGG     1200
TACCATGGAC GGCCCCGTCA GCCACACCTG TCAGCCCAAG CAGAGTGATT CAGGGGCTCC     1260
CCGGGGGCAG GCACCTGTGC ACCCCATGAG TAGTGCCCAC TTGAGGCTGG CACTCCCCTG     1320
ACCTCACCTT TGCAAAGTTA CAGATGCACC CCAACATTGA GATGTGTTTT TAATGTTAAA     1380
ATATTGATTT CTACGTTATG AAAACAGATG CCCCCGTGAA TGCTTACCTG TGAGATAACC     1440
ACAACCAGGA AGAACAAATC TGGGCATTGA GCAAGCTATG AGGGTCCCCG GGAGCACACG     1500
AACCCTGCCA GGCCCCCGCT GGCTCCTCCA GGCACGTCCC GGACCTGTGG GGCCCCAGAG     1560
AGGGGACATT TCCCTCCTGG GAGAGAAGGA GATCAGGGCA ACTCGGAGAG GGCTGCGAGC     1620
ATTTCCCTCC CGGAGAGGA GATCAGGGCG ACCTGCACGC ACTGCGTAGA GCCTGGAAGG     1680
GAAGTGAGAA ACCAGCCGAC CGGCCCTGCC CCTCTTCCCG GGATCACTTA ATGAACCACG     1740
TGTTTTGACA TCATGTAAAC CTAAGCACGT AGAGATGATT CGGATTTGAC AAAATAACAT     1800
TTGAGTATCC GATTCGCCAT CACCCCCTAC CCCAGAAATA GGACAATTCA CTTCATTGAC     1860
CAGGATGATC ACATGGAAGG CGGCGCAGAG GCAGCTGCGT GGGCTGCAGA TTTCCTGTGT     1920
GGGGTTCAGC GTAGAAAACG CACCTCCATC CCGCCCTTCC CACAGCATTC CTCCATCTTA     1980
GATAGATGGT ACTCTCCAAA GGCCCTACCA GAGGGAACAC GGCCTACTGA GCGGACAGAA     2040
TGATGCCAAA ATATTGCTTA TGTCTCTACA TGGTATTGTA ATGAATATCT GCTTTAATAT     2100
AGCTATCATT TCTTTTCCAA AATTACTTCT CTCTATCTGG AATTTAATTA ATCGAAATGA     2160
ATTTATCTGA ATATAGGAAG CATATGCCTA CTTGTAATTT CTAACTCCTT ATGTTTGAAG     2220
AGAAACCTCC GGTGTGAGAT ATACAAATAT ATTTAATTGT GTCATATTAA ACTTCTGATT     2280
TCACCAAAAA AAAAAAAAAA AAAAAAAAAA AAAGCGGCCG CTGAATTC                  2328
```